US007078438B2

(12) United States Patent
Rewcastle et al.

(10) Patent No.: US 7,078,438 B2
(45) Date of Patent: Jul. 18, 2006

(54) N-(4 SUBSTITUTED PHENYL)-ANTHRANILIC ACID HYDROXAMATE ESTERS

(75) Inventors: Gordon William Rewcastle, Glendowie (NZ); Julie Ann Spicer, Pakuranga Heights (NZ); Stephen Douglas Barrett, Hartland, MI (US); Michael David Kaufman, Ypsilanti, MI (US); Jared Bruce John Milbank, Dexter, MI (US); Haile Tecle, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 46 days.

(21) Appl. No.: 11/051,142

(22) Filed: Feb. 4, 2005

(65) Prior Publication Data
US 2005/0137263 A1    Jun. 23, 2005

Related U.S. Application Data

(63) Continuation of application No. 10/349,801, filed on Jan. 23, 2003, now Pat. No. 6,891,066.

(60) Provisional application No. 60/351,201, filed on Jan. 23, 2002.

(51) Int. Cl.
    *A61K 31/165*    (2006.01)
(52) U.S. Cl. .................... 514/619; 514/507; 514/825
(58) Field of Classification Search ................ 514/619, 514/507, 825
    See application file for complete search history.

(56) References Cited

U.S. PATENT DOCUMENTS

| 2,082,171 | A | 6/1937 | Mietzsch et al. |
| 2,502,451 | A | 4/1950 | Goldberg et al. |
| 2,553,914 | A | 5/1951 | Goldberg et al. |
| 3,781,358 | A | 12/1973 | Anderson et al. |
| 4,510,139 | A | 4/1985 | Bailey |
| 4,921,875 | A | 5/1990 | Englert et al. |
| 5,068,250 | A | 11/1991 | Penning et al. |
| 5,525,625 | A | 6/1996 | Bridges et al. |
| 6,310,060 | B1 | 10/2001 | Barrett et al. |

FOREIGN PATENT DOCUMENTS

| EP | 0242559 | 3/1987 |
| EP | 0316630 | 5/1989 |
| GB | 1371378 | 10/1974 |
| WO | WO 93/24442 | 12/1993 |
| WO | WO 97/07790 | 3/1997 |
| WO | WO 97/47270 | 12/1997 |
| WO | WO 98/37881 | 9/1998 |
| WO | WO 99/01421 | 1/1999 |
| WO | WO 99/01426 | 1/1999 |
| WO | WO 99/21840 | 5/1999 |
| WO | WO 00/41505 | 7/2000 |
| WO | WO 02/06213 | 1/2002 |

OTHER PUBLICATIONS

PCT International Search Report PCT/US99/30491, 2000.
Fujimura, H., "Hydroxamic Acid Derivatives," *Chemical Abstracts*, 1969, Abstract No. 11330, vol. 70, No. 3.
Hunziker, F., "Chemistry and Pharmacology of Dibenzo[b,e][1,4]Diazepine Derivatives iwth Basic Substituents in Position 10," *Chemical Abrstracts*, 1963, Abstract No. 8753f, vol. 59, No. 8.
Yu, V. O., "Acridine Derivatives as a Source of Antimalarials," *Chemical Abstracts*, 1941, Abstract No. 7965h, vol. 35, No. 22.
Cook, A. H., "pYRIDYLACRIDINES," *Chemical Abstracts*, 1944, Abstract No. 105, vol. 38, No. 1.
Fujimura, H., et al., "Hydroxamic Acid Derivatives," *Database Chemabs Online*, Accession No. 1969:11330.
Mokhort, N. A., "Dependence Between Structure, Antiinflammatory, Analgesic, and Antipyretic Actions in N-aromatic Deriviatives of Anthranilic Acid," *Database Chemabs Online*, Accession No. 1972:121461.
Hirano, H., et al., "Novel N-phenylanthranilic acid derivatives," *Database Chemabs Online*, Accession No. 1968:418858.
Endelman, E. S., et al., "Synthesis and physiological properties of N-phenylanthranilic acids with fluorine-containing substituents," *Database Chemabs Online*, Accession No. 1974:70488.
Hunziker, F., et al., "Pharmacology of Dibenzo[b,e][1,4]Diazepine Derivatives with Basic Substituents in Position 10," *Database Chemabs Online*, Accession No. 8753f, 1963.
Takeda, M., et al., "Synthesis of Dibenzo[b,e][1,4]Diazepine Derivatives as Anti-Depressants," *Database Chemabs Online*, Accession No. 1969:403368.
Magidson, O. U., et al., "Acridine Compounds as a Source of Medicinal Products (V)," *Database Chemabs Online*, Acession No. 35:7965h, 1941.
PCT International Search Report PCT/IB03/00211, 2003.

*Primary Examiner*—Shailendra Kumar
(74) *Attorney, Agent, or Firm*—Bryan C. Zielinski; Galina M. Yakovleva

(57) ABSTRACT

The present invention relates to oxygenated esters of 4-substituted-phenylamino benzhydroxamic acid derivatives, pharmaceutical compositions and methods of use thereof.

10 Claims, No Drawings

N-(4 SUBSTITUTED PHENYL)-ANTHRANILIC ACID HYDROXAMATE ESTERS

This application is a continuation of application Ser. No. 10/349,801, filed Jan. 23, 2003 now U.S. Pat. No. 6,891,066, which claims the benefit of U.S. Provisional Application No. 60/351,201 filed Jan. 23, 2002, the contents of which are hereby incorporated by reference in their entireties.

FIELD OF THE INVENTION

The present invention relates to oxygenated esters of 4-substituted-phenylamino benzhydroxamic acid derivatives, pharmaceutical compositions and methods of use thereof.

BACKGROUND OF THE INVENTION

MAPK/ERK Kinase ("MEK") enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates the MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinaes. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

It has been found that the compounds of the present invention are inhibitors of MEK and are useful in the treatment of a variety of proliferative disease states, such as conditions related to the hyperactivity of MEK, as well as diseases modulated by the MEK cascade.

SUMMARY OF THE INVENTION

The compounds of Formula I are a sub-genus of the genus disclosed in WO 00/41505, which is PCT Application No. PCT/US99/30491. Surprisingly, the compounds of the present invention have unexpectedly superior properties as MEK inhibitors.

The present invention provides a compound of formula

I

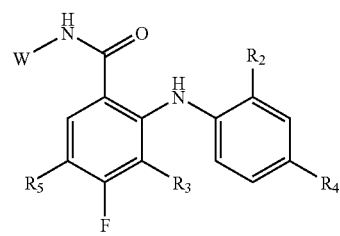

wherein
W is

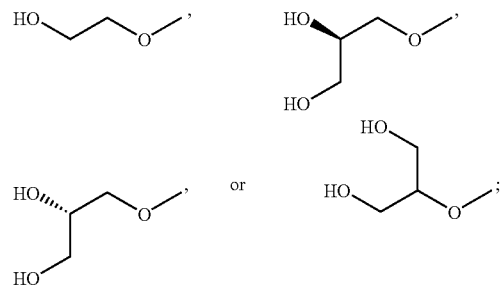

$R_2$ is hydrogen, methyl, fluorine, or chlorine;
$R_3$ is hydrogen or fluorine;
$R_4$ is $C_{1-6}$ alkyl, $C_{2-4}$ alkenyl, $C_{2-6}$ alkynyl, $C_{3-6}$ cycloalkyl, —($CH_2$)—$C_{3-6}$ cycloalkyl, —O—($C_{1-4}$ alkyl), —S—($C_{1-2}$ alkyl), —SO$_2$CH$_3$, —SO$_2$NR$_6$R$_7$, —C≡C—(CH$_2$)$_n$NH$_2$, —C═C(CH$_2$)$_n$OH, —C═C—(CH$_2$)$_n$NH$_2$, —(CH$_2$)$_m$NH$_2$, —(CH$_2$)$_m$NHCH$_3$, —(CH$_2$)$_m$N(CH$_3$)$_2$, —(CH$_2$)$_m$OR$_8$, —(CH$_2$)$_q$CF$_3$, —C≡CCF$_3$, —CH═CHCF$_3$, —CH$_2$CHCF$_2$, or —CH═CF$_2$, wherein the C$_{1-6}$ alkyl and C$_{2-6}$ alkynyl are optionally substituted with between 1 and 3 substituents selected from hydroxy and alkyl;

m is 1 to 4;

n is 1 to 2;

q is 0 to 2;

R$_5$ is hydrogen or chlorine;

R$_6$ and R$_7$ are each independently hydrogen, methyl, or ethyl;

and pharmaceutically acceptable salts, (C$_{1-6}$) amides and (C$_{1-6}$) esters thereof.

Also provided by the present invention are compounds of Formula I, wherein
W is

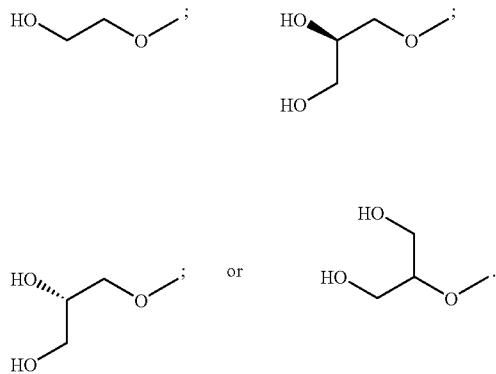

The present invention also provides compounds of Formula I, wherein R$_2$ is hydrogen, fluorine, or chlorine.

Additionally, the present invention provides compounds of Formula I, wherein R$_4$ is C$_{1-6}$ alkyl, C$_{2-4}$ alkenyl, C$_{2-3}$ alkynyl, —(CH$_2$)$_m$OR$_6$, —S—(C$_{1-2}$ alkyl) or —SO$_2$CH$_3$; R$_4$ is C$_{1-6}$ alkyl; R$_4$ is ethyl; R$_4$ is C$_{2-4}$ alkenyl or C$_{2-3}$ alkynyl; R$_4$ is vinyl; R$_4$ is —(CH$_2$)$_m$OR$_6$; or R$_4$ is —(CH$_2$)$_q$CF$_3$, —CH$_2$CHCF$_2$, or —CH═CF$_2$.

Also provided by the present invention are compounds of Formula I, wherein R$_5$ is hydrogen.

The invention also provides a pharmaceutical composition comprising a compound of Formula I and a pharmaceutically acceptable carrier.

Additionally, the invention provides a method of treating a proliferative disease in a patient in need thereof comprising administering a therapeutically effective amount of a compound of Formula I.

The invention also provides the use of a compound of Formula I for the manufacture of a medicament for the treatment of a proliferative disease.

Furthermore, the invention provides methods of treating cancer, restenosis, psoriasis, autoimmune disease, atherosclerosis, osteoarthritis, rheumatoid arthritis, heart failure, chronic pain, and neuropathic pain in a patient in need thereof comprising administering a therapeutically effective amount of a compound of Formula I.

The invention also provides the use of a compound of Formula I for the manufacture of a medicament for the treatment of cancer, restenosis, psoriasis, autoimmune disease, atherosclerosis, osteoarthritis, rheumatoid arthritis, heart failure, chronic pain, and neuropathic pain.

In addition, the invention provides a method for treating cancer in a patient in need thereof comprising administering a therapeutically effective amount of a compound of Formula I in combination with radiation therapy or at least one chemotherapeutic agent.

DETAILED DESCRIPTION OF THE INVENTION

Certain terms are defined below and by their usage throughout this disclosure.

The terms "halogen" or "halo" in the present invention refer to a fluorine, bromine, chlorine, and iodine atom or fluoro, bromo, chloro, and iodo. The terms fluorine and fluoro, for example, are understood to be equivalent herein.

Alkyl groups, such as "C$_{1-6}$ alkyl", include aliphatic chains (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, isobutyl, sec-butyl, t-butyl, pentyl, 2-pentyl, 3-pentyl, isopentyl, neopentyl, (R)-2-methylbutyl, (S)-2-methylbutyl, 3-methylbutyl, 2,3-dimethylpropyl, hexyl, and the like. The term "C$_{1-6}$ alkyl" includes within its definition the terms "C$_{1-4}$ alkyl" and "C$_{1-2}$ alkyl".

Alkenyl groups are analogous to alkyl groups, but have at least one double bond (two adjacent sp$^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof. Like alkyl groups, unsaturated groups may be straight chain or branched. Examples of alkenyls and alkynyls include vinyl, allyl, 2-methyl-2-propenyl, cis-2-butenyl, trans-2-butenyl, and acetyl.

Cycloalkyl groups, such as C$_{3-6}$ cycloalkyl, refer to a saturated hydrocarbon ring structure containing from 3 to 6 atoms. Typical C$_{3-6}$ cycloalkyl groups include cyclopropyl, cyclobutyl, cyclopentyl, cyclohexyl, and the like.

The present invention includes the hydrates and the pharmaceutically acceptable salts and solvates of the compounds defined by Formula I. The compounds of this invention can possess a sufficiently basic functional group, and accordingly react with any of a number of inorganic and organic acids, to form a pharmaceutically acceptable salt.

The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science,* 1977; 66:2–19, which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Example of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymateate, mandelate, mesylate, nicotinate, isonicotinate, cinnamate, hippurate, nitrate, stearate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydrozybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, hemi-tartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartarate, and the like. A preferred pharmaceutically acceptable salt is hydrochloride.

It should be recognized that the particular counterion forming a part of any salt of this inventions is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to each of two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of enantiomers.

The enantiomers of compounds of the present invention can be resolved by one of ordinary skill in the art using standard techniques well-known in the art, such as those described by J. Jacques, et al., "Enantiomers, Racemates, and Resolutions", John Wiley and Sons, Inc 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The compounds of Formula I can be prepared by techniques and procedures readily available to one of ordinary skill in the art, for example by following the procedures as set forth in the following Schemes, or analogous variants thereof. These synthetic strategies are further exemplified in examples below. These schemes are not intended to limit the scope of the invention in any way.

As used herein, the following terms have the meanings indicated: "BOC" refers to tert-butoxycarbonyl; Celite® refers to a filter agent which is acid washed and approximately 95% $SiO_2$; "DMA" refers to N,N-dimethylacetamide; "DMT-MM" refers to 4-(4,6-dimethoxy-1,3,5-triazin-2-yl)-4-methylmorpholinium chloride; "EtOAc" refers to ethyl acetate; "$Et_2O$" refers to diethyl ether; "EtOH" refers to ethanol; "h" refers to hours; "LiHMDS" refers to lithium 1,1,1,3,3,3-hexamethyldisilazane or lithium bis(trimethylsilylamide); "Lindlar catalyst" refers to a Pd/$CaCO_3$ catalyst washed with Pb(OAc)$_2$; "Me" refers to methyl; "MeOH" refers to methanol; "MsCl" refers to methane sulfonyl chloride; "Pd/C" refers to palladium on carbon; "PE" refers to petroleum ether which can be substituted with "hexanes"; "$(Ph_3P)_2PdCl_2$" refers to dichlorobis(triphenylphosphine) palladium(II); "$(Ph_3P)_4Pd$" refers to tetrakis(triphenylphosphine)palladium(0); "PyBop" refers to benzotriazole-1-yl-oxy-tris-pyrrolidino-phosphonium hexafluorophosphate; "RT" refers to room temperature; "TEA" refers to triethylamine; "TFA" refers to trifluoroacetic acid; "THF" refers to "tetrahydrofuran; "TLC" refers to thin layer chromatography; and "TMS" refers to trimethylsilyl. All other terms and substituents, unless otherwise indicated, are previously defined. The reagents and starting materials are readily available to one of ordinary skill in the art. Schemes 1 and 2 provide syntheses of the compounds of Formula I.

Scheme 1

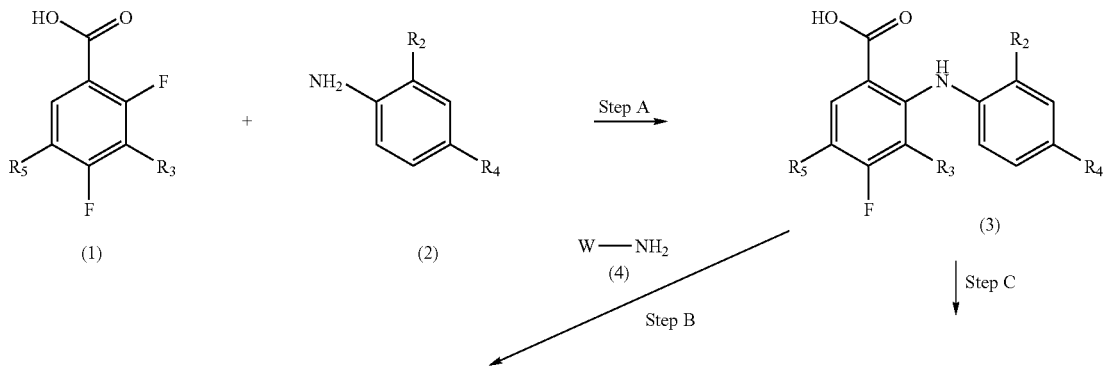

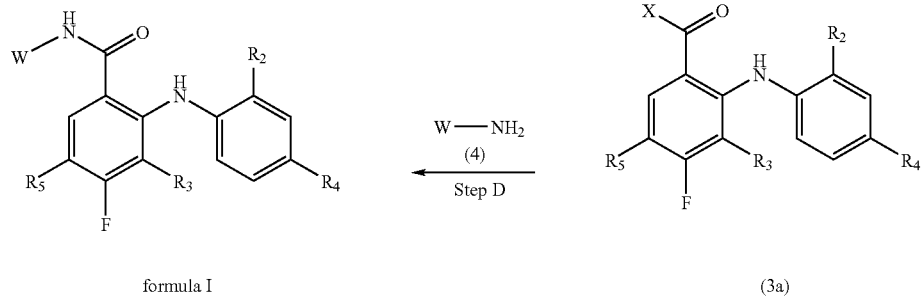

formula I                (3a)

In Scheme 1, Step A, a 2-(arylamino)-benzoic acid or diphenylamine (3) is prepared from the coupling of a suitable benzoic acid (1) and a suitable aniline (2) in the presence of a strong base, for example, lithium 1,1,1,3,3,3-hexamethyldisilazane (LiHMDS) or lithium diisopropylamide, in a polar aprotic solvent such as tetrahydrofuran, acetonitrile or dimethylformamide. For example, the aniline (2) and the benzoic acid (1) are dissolved in a suitable organic solvent and cooled to about −78° C. under nitrogen. The suspension is treated with an excess of a suitable base, such as LiHMDS, and allowed to warm to room temperature. The reaction is typically complete within about 2 hours to about 5 days. The resulting benzoic acid (3) can be isolated by removing the solvent, for example by evaporation under reduced pressure or by filtering the precipitated solid through Celite® and washing with a suitable solvent. The benzoic acid (3) can be further purified, if desired, by standard methods such as chromatography, crystallization, or distillation.

In Scheme 1, Step B, the compounds of Formula I are generally obtained by the union of 2-(arylamino)-benzoic acid (3) with an alkoxylamine (4) by the action of a peptide coupling agent in the presence of a base, if necessary. It is understood that the alkoxylamine (4) may be suitably protected. In such instances, Scheme 1 may be modified to include a removal of the protecting group by a procedure known in the art. Preferred coupling agents include 1,1'-carbonyldiimidazole (CDI), lithium bis (trimethylsilylamide) (LiHMDS), diphenylphosphinic chloride (DPP-Cl), benzotriazol-yl-oxy-tripyrolidinophosphonium hexafluorophosphate (PyBOP), benzotriazol-1-yloxy-tris(dimethylamino)phosphonium hexafluorophosphate (BOP), N,N'-dicyclohexylcarbodiimide (DCC), or 1-ethyl-3-(3-dimethylaminopropyl)carbodiimide hydrochloride (EDCI). Preferred bases include diisopropylethylamine, triethylamine, 4-methylmorpholine, or pyridine or a substituted pyridine, for example, 4-dimethyaminopyridine or 2,6-dimethylpyridine. Preferred solvents are polar aprotic solvents such as dichloromethane, tetrahydrofuran, or dimethylformamide. The reactions are generally carried out at a temperature between about −78° C. to about 25° C., and are normally complete within about 1 hour to about 5 days. The product amide can be isolated by removing the solvent, for example by evaporation under reduced pressure, and further purified, if desired, by standard methods such as chromatography, crystallization, or distillation.

It would be understood by one of skill in the art that the substituent at $R_4$ on the diphenylamine (3) can be reduced before the coupling reaction. The reduction is performed on alkene or alkyne derivatives under conditions known in the art, such as through hydrogenation, for example with Pd/C under an atmosphere of hydrogen.

Alternately, the compounds of formula I are generally prepared as shown in Scheme 1, steps C and D by the contact of alkoxyamine (4) with "activated" benzoic acid derivatives (3a), wherein the activating group "X" completes an acid halide, anhydride, mixed anhydride, or an activated ester, such as a pentafluorophenyl ester, nitrophenyl ester or thioester. Preferred bases include diisopropylethylamine, triethylamine, 4-methylmorpholine, imidazole, pyridine or a substituted pyridine, for example, 4-dimethyaminopyridine or 2,6-dimethylpyridine. Preferred solvents are polar aprotic solvents such as dichloromethane, tetrahydrofuran, dimethylformamide, or N,N-dimethylacetamide.

Scheme 2

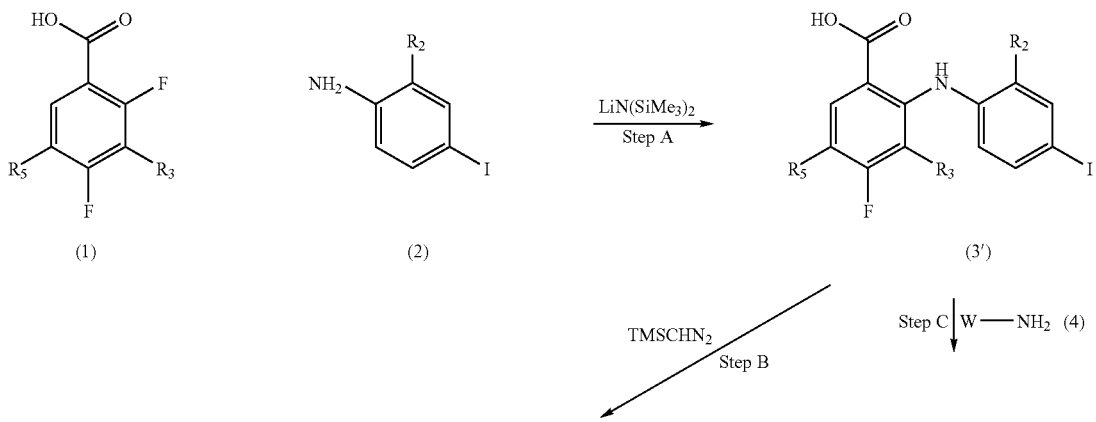

-continued

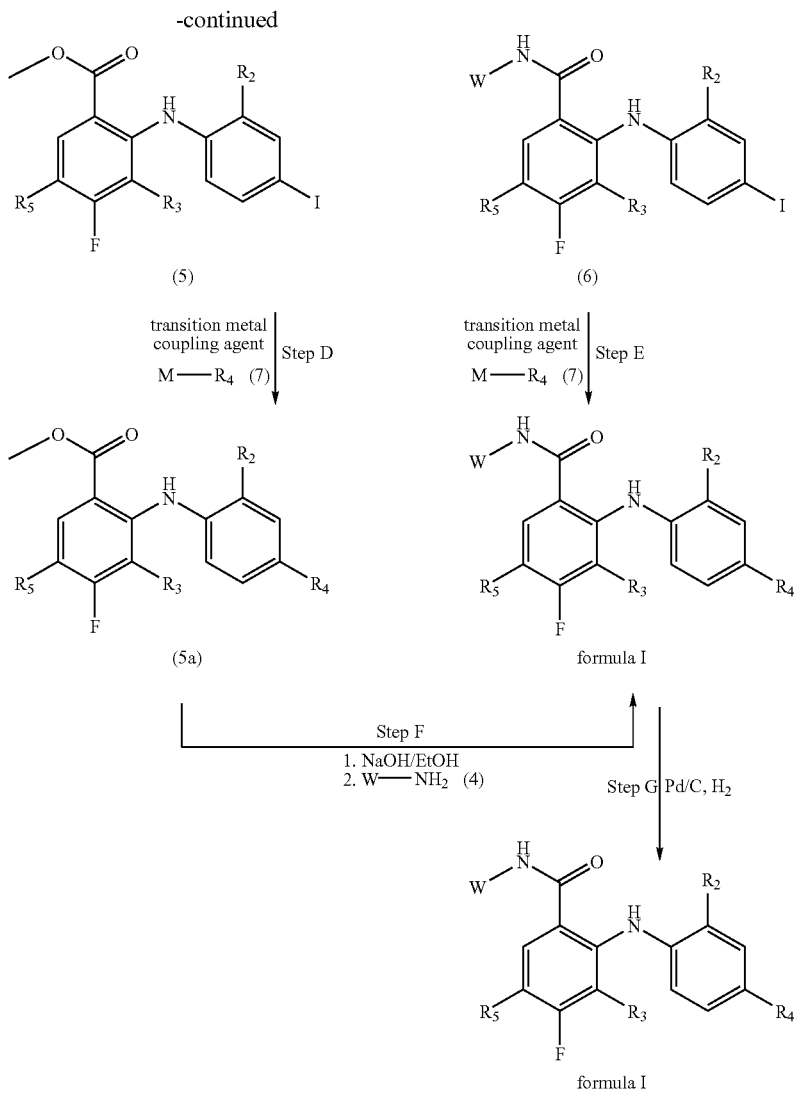

In Scheme 2, Step A, a 4-iodo phenylamino benzoic acid (3') is prepared from the union of a suitable benzoic acid (1) and a suitable 4-iodoaniline (2'), in the presence of a strong base, for example, lithium bis(trimethylsilylamide) or lithium diisopropylamide, in a polar aprotic solvent such as tetrahydrofuran or acetonitrile. For example, lithum bis (trimethylsilylamide) is added to a solution of the benzoic acid (1) in tetrahydrofuran and added to a separate solution of the 4-iodoaniline (2'). Each reaction is carried out at about −78° under nitrogen. The benzoic acid (1) solution is transferred to the 4-iodoaniline (2') solution using positive nitrogen pressure and stirred for 6–12 hours at ambient. The resulting 4-iodophenylamino benzoic acid (3') is isolated by removing the solvent, for example by filtering the precipitated solid through Celite® and washing with a suitable solvent, and further purified, if desired, by standard methods such as chromatography, crystallization, or distillation.

In Scheme 2, Step B, the 4-iodo phenylamino benzoic acid (3') is protected as the methyl 4-iodo-phenylamino benzoate (5) using a suitable reagent, such as TMS-diazomethane. For example, a suitable reagent, such as TMS-diazomethane is added dropwise to a solution of the benzoic acid (3') in a suitable solvent, such as a mixture of diethyl ether and and methanol. This mixture is stirred at room temperature for about 6 hours to 2 days, followed by quenching of the excess reagent with a suitable weak acid, such as acetic acid, to provide the methyl ester (5).

In Scheme 2, Step C, the 4-iodo phenylamino benzoic acid (3') is coupled with an alkoxylamine (4) according to the general procedure of Scheme 1, Step B or Scheme 1, Steps C and D to provide the 4-iodo-phenylamino benzamide (6).

In Scheme 2, Step D, the methyl 4-substituted-phenylamino benzoate (5a) are prepared from the methyl 4-iodophenylamino benzoate (5), by transition metal-promoted coupling with reagent M-$R_4$ (7) in a suitable solvent such as triethylamine, tetrahydrofuran or dimethylformamide. The entire mixture is stirred from about 2 to 24 hours at room temperature. The transition metal-promoted coupling may be carried out with a palladium(0) or palladium (II) coupling agent, such as $(Ph_3P)_4Pd$ or $(Ph_3P)_2PdCl_2$. M is defined as a functional group known to transfer a carbon radical fragment in transition metal-promoted coupling processes. Examples of a suitable M group include trialkylstannyl, trialkylsilyl, trimethylsilyl, zinc, copper, boron, magnesium and lithium. It would be understood by one of skill in the art that the substituent $R_4$ may be further transformed, such as by oxidation, reduction, deprotection, or hydrogenation. The substituent $R_4$ may also be transformed into a different $R_4$ through standard synthetic procedures known to one of skill in the art. The resulting compound of formula I, as well as the protected Formula I compound, can be isolated by removing the solvent, for example by evaporation under reduced pressure, and further purified, if desired, by standard methods such as chromatography, crystallization, or distillation.

In Scheme 2, Step E, the compounds of Formula I are prepared from the 4-iodo-phenylamino benzamide (6), by transition metal-promoted coupling with reagent $M-R_4$ (7) according to the general procedure of Scheme 2, Step D.

In Scheme 2, Step F, the methyl 4-substituted-phenylamino benzoate (5a) is deprotected in a manner known to one of skill in the art, for example, aqueous NaOH in EtOH, then coupled with an alkoxylamine (4) according to the general procedure of Scheme 1, Step B.

In Scheme 2, Step G, $R_4$, if saturated, can be converted to a fully saturated substituent through hydrogenation, for example with Pd/C under an atmosphere of hydrogen.

In Scheme 3, Step A, the methyl 4-iodo-phenylamino benzoate (5) is prepared according to the procedure of Scheme 2, Step B.

In Scheme 3, Step B. the methyl 4-alkene substituted benzoate (5b) is prepared according to the procedure of Scheme 2, steps D and E, where the transition metal-promoted coupling of the methyl 4-iodo-phenylamino benzoate (5) is carried out using a suitable reagent such as allyltributyltin or tetravinyltin.

In Scheme 3, Step C the methyl 4-alkene substituted benzoate (5b) is deprotected according to the procedure of Scheme 2, Step F. then coupled with an alkoxylamine (4) according to the general procedure of Scheme 1, Step B to provide a compound of formula I wherein $R_4$ is $C_{2-3}$ alkene (formula Ia).

In Scheme 3, Step D, compounds of formula (5c) were prepared from the methyl 4-alkene substituted benzoate (5b) by reaction of the double bond at the 4' position of the phenylamine with ozone and $NaBH_4$, to give the alcohol (5c).

In Scheme 3, step E, the double bond at the 4' position of the phenylamine of formula Ia may be treated with $OsO_4$ for example, in order to give the corresponding diol, which is a

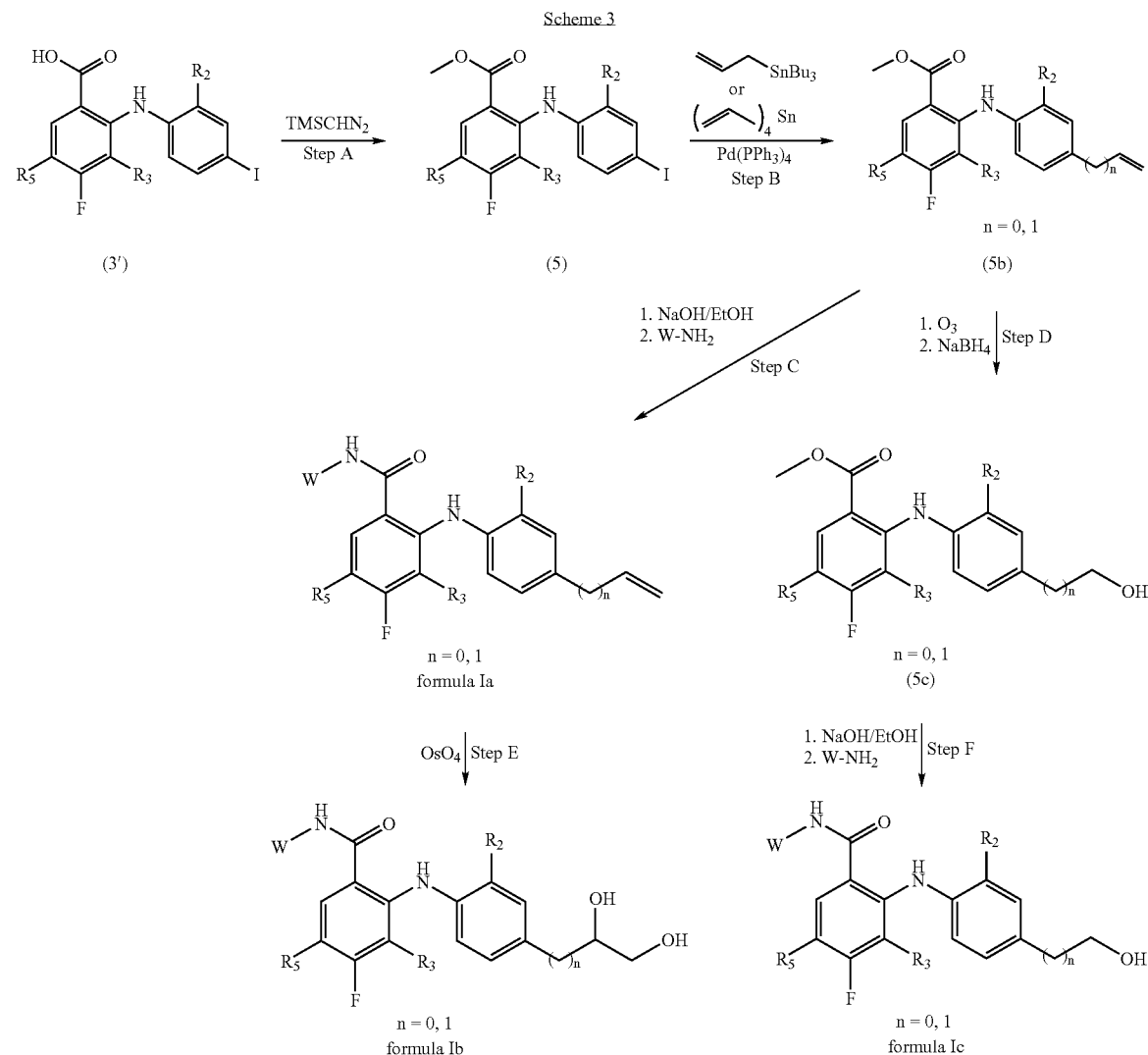

compound of formula I wherein $R_4$ is alkyl substituted with 2 hydroxy substituents (formula Ib).

In Scheme 3, Step F, the methyl ester group of the alcohol compound (5c) is deprotected according to the procedure of Scheme 2, Step F, then coupled with an alkoxylamine (4) according to the general procedure of Scheme 1, Step B to provide a compound of formula I wherein $R_4$ is alkyl substituted with a hydroxy substituent (formula Ic).

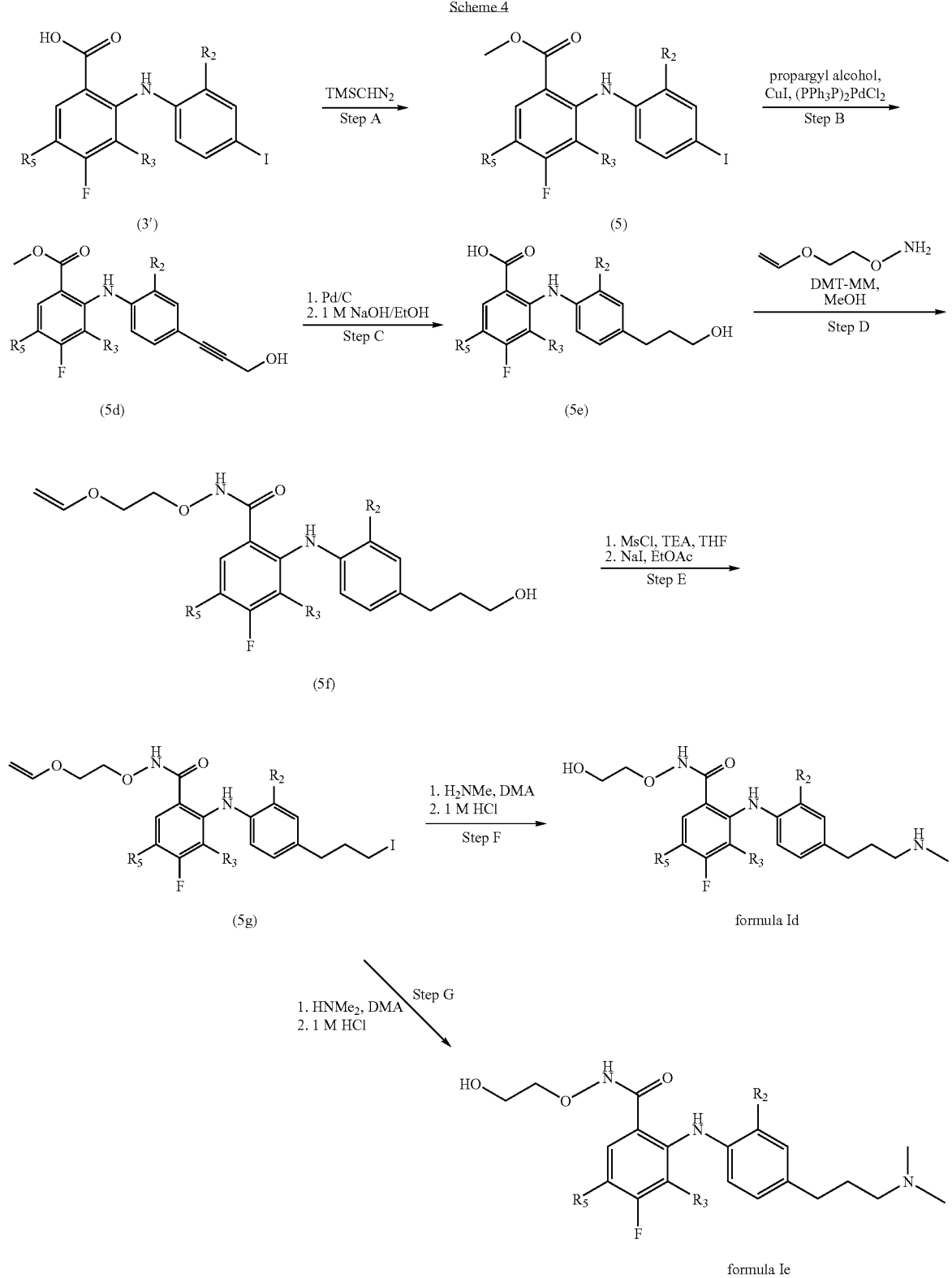

In Scheme 4, Step A, the methyl 4-iodo-phenylamino benzoate (5) is prepared from the 4-iodo phenylamino benzoic acid (3') according to the general procedure of Scheme 2, Step B.

In Scheme 4, Step B, the compounds (5d) are prepared according to the procedure of Scheme 2, Steps D and E, where the transition metal-promoting coupling of the methyl 4-iodo-phenylamino benzoate (5) is carried out using a suitable reagent, such as propargyl alcohol.

In Scheme 4, Step C, the compound (5d) is converted to the fully saturated carboxylic acid through hydrogenation, for example with Pd/C under an atmosphere of hydrogen. The methyl ester of the compound (5d) is then deprotected according to the procedure of Scheme 2, Step F.

In Scheme 4, step D, the alcohol (5e) is coupled with an alkoxylamine (4) according to the general procedure of Scheme 1, Step B.

In Scheme 4, step E, the compound (5f) is dissolved in a suitable solvent such as tetrahydrofuran and reacted with methanesulfonyl chloride to give the intermediate mesylate, then NaI in EtOAc to give the iodide compound (5g).

In Scheme 4, steps F and G, the iodide compound (5g) is reacted with methylamine and dimethylamine respectively to give compounds of formula 1 wherein m is 3 and $R_4$ is —$(CH_2)_m NHCH_3$ (formula Id) and —$(CH_2)_m N(CH_3)_2$ (formula Ie).

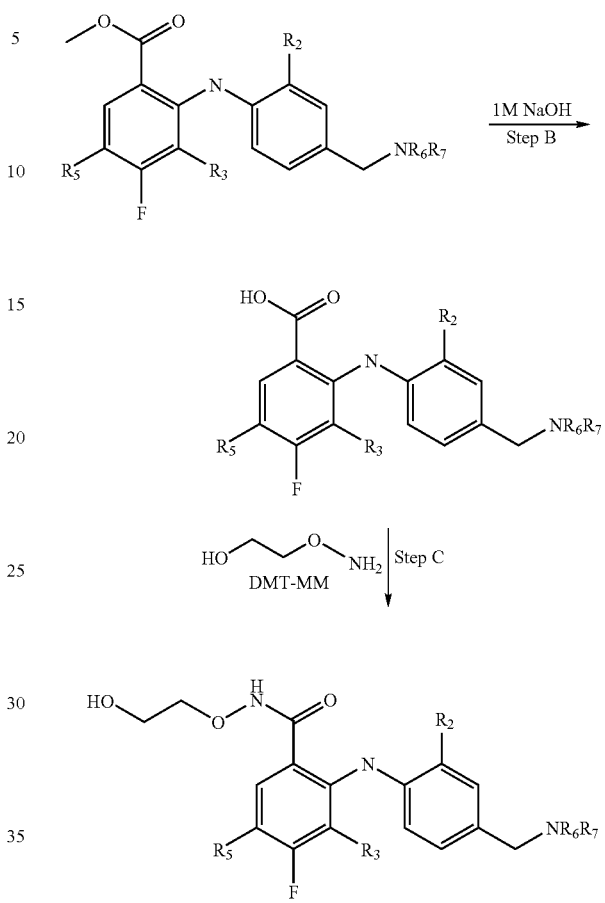

In Scheme 4A, Step A, the iodide compound is reacted with a suitable amine to provide the amide substituted methyl ester compound.

In Scheme 4A, Step B, the methyl ester compound is deprotected according to the general procedure of Scheme 4, Step C.

In Scheme 4A, Step C, the alcohol (5e) is coupled with an alkoxylamine (4) according to the general procedure of Scheme 1, Step B to provide the compound of formula I where $R_4$ is —$(CH_2)NR_6R_7$.

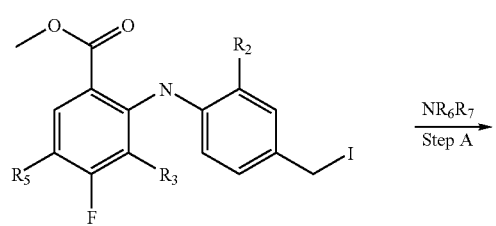

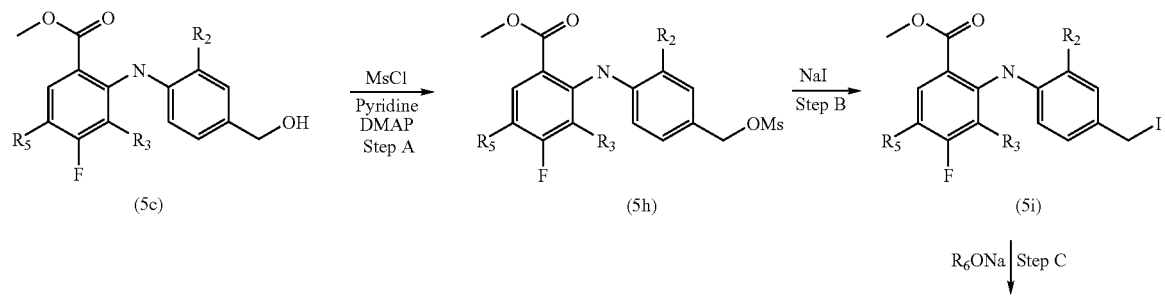

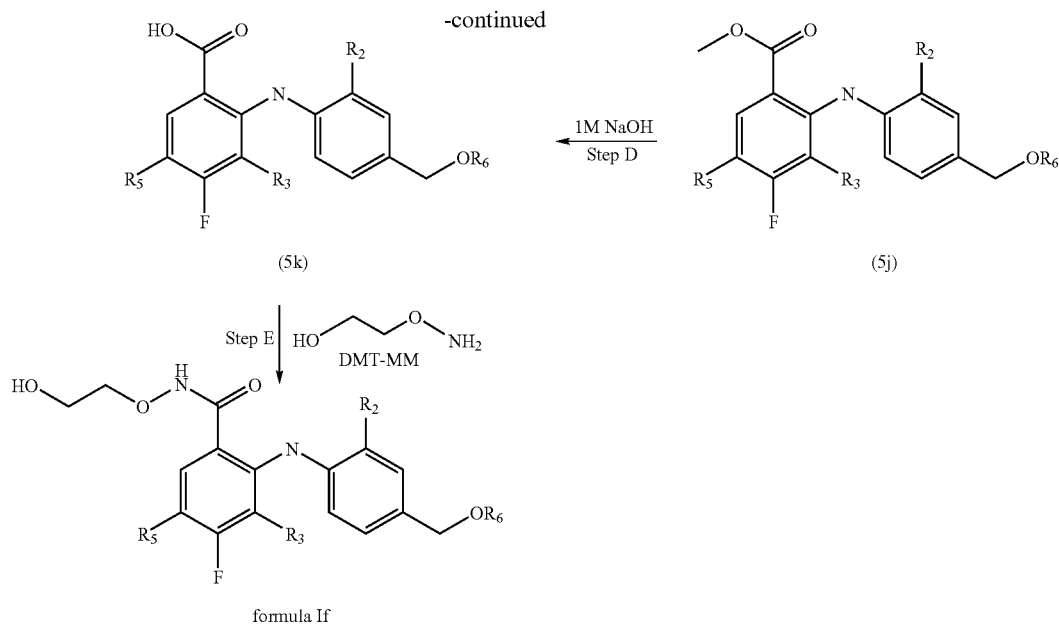

(5k)

(5j)

formula If

In Scheme 5, Step A, the alcohol compound (5c) is reacted with methanesulfonyl chloride to give the mesylate (5h) according to the general procedure of Scheme 4, Step E.

In Scheme 5, Step B, the mesylate (5d) is reacted with NaI in ethyl acetate to provide the iodide compound (5i).

In Scheme 5, Step C, the iodide compound (5i) is reacted with a suitable alkoxide to provide the compound (5j).

In Scheme 5, Step D, the methyl ester of the compound (5j) is deprotected according to the procedure of Scheme 2, Step F to provide the carboxylic acid (5k).

In Scheme 5, Step E, the carboxylic acid (5k) is coupled with an alkoxylamine (4) according to the general procedure of Scheme 1, Step B to provide the compound of formula I wherein $R_4$ is —$(CH_2)_mOR_6$ (formula If).

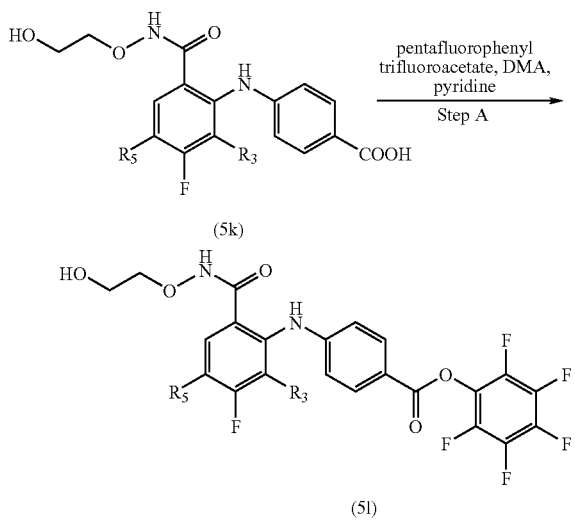

Scheme 6

(5k)

(5l)

formula Ig

In Scheme 6, Step A, the benzoic acid (5k) is activated according to the general procedure of Scheme 1, Step C to provide the pentafluorophenyl compound (5l).

In Scheme 6, Step B, sodium borohydride was added to a solution of the pentafluorophenyl compound (5l) in a suitable solvent, such as tetrahydrofuran to provide the compound of formula I wherein $R_4$ is methyl substituted with hydroxy (formula Ig).

The aniline (2) can be prepared by techniques and procedures readily available to one of ordinary skill in the art and by following the procedures as set forth in the following Schemes, or analogous variants thereof. These Schemes are not intended to limit the scope of the invention in any way.

Scheme 7

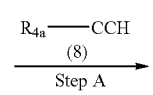

(2')

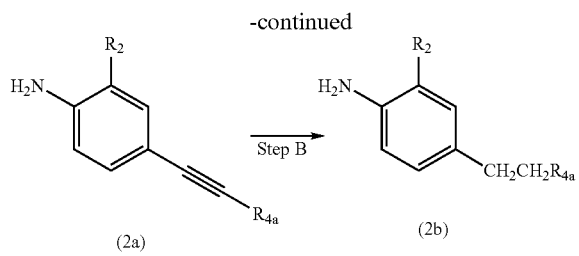

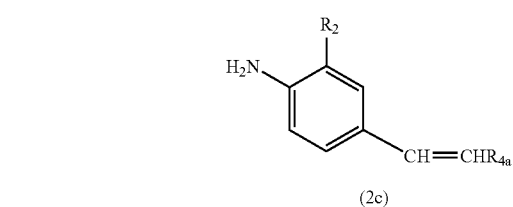

$R_{4a}$ is alkyl

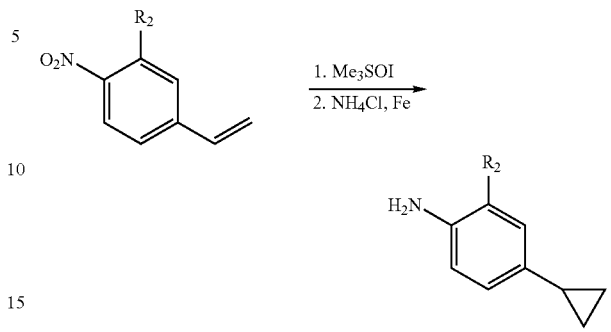

Bull. Soc. Chim. Belg., 95(2), 135-8; 1986

In Scheme 8, a suitably substituted para-nitrostyrene is reacted with dimethyloxosulfonium methylide to form the substituted para-nitrocyclopropylbenzene. Reduction of para-nitrocyclopropylbenzene with iron in the presence of weak acid gives the desired aniline.

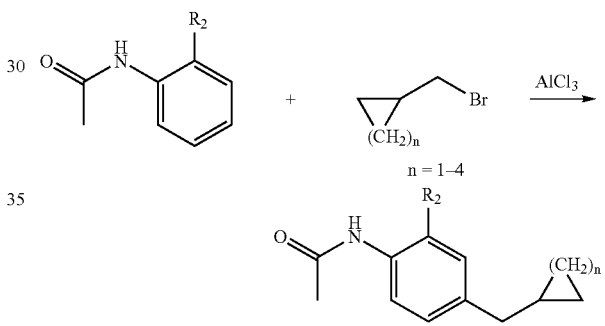

In Scheme 9, the suitable ortho-substituted acetamide is reacted with bromocyclobutane, bromocyclopropane, or bromocyclohexane under typical Friedel-Craft conditions, as known to one of skill in the art, to give the desired para-cycloalkylanilines.

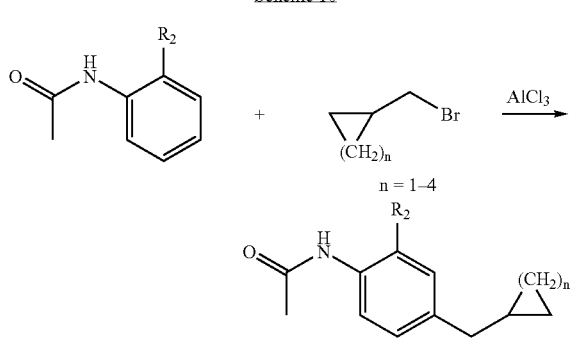

In Scheme 10, a suitable ortho-substituted acetamide is reacted with a suitable bromomethylcycloalkane under typical Friedel-Craft conditions, as known to one of skill in the art, to give para-cycloalkylmethylacetamides. The aceta- In Scheme 7, Step A, the alkynylaniline (2a) is prepared via Sonogashira coupling with a suitable 4-iodoaniline (5). For example, a 4-iodoaniline (5), such as 2-fluoro-4-iodoaniline, is combined with CuI and $(Ph_3P)_2PdCl_2$ under nitrogen. A suitable acetylene derivative (8) is added in a suitable solvent, such as TEA, and the entire mixture is stirred from about 2 to 24 hours at room temperature. The resulting alkynylaniline (2a) can be isolated by removing the solvent, for example by evaporation under reduced pressure, and further purified, if desired, by standard methods such as chromatography, crystallization, or distillation. It is understood that the alkynylaniline (2a) may be suitably protected. In such instances, Scheme 7 may be modified to include removal of a protecting group by a procedure known in the art.

In Scheme 7, Step B, alkynylaniline (2a) is reduced via hydrogenation to provide the aniline (2b). The alkynylaniline (2a) is dissolved in a suitable solvent, such as absolute ethanol, in the presence of a metal catalyst, such as palladium on carbon. This mixture is stirred under an atmosphere of hydrogen from about 1 to 24 hours at room temperature. The resulting aniline (2b) can be isolated by removing the solvent, for example by evaporation under reduced pressure, and further purified, if desired, by standard methods such as chromatography, crystallization, or distillation.

In Scheme 7, Step C, alkynylaniline (2a) is partially reduced via hydrogenation to provide the alkenylaniline (2c). For example, the alkynylaniline (2a) is dissolved in a suitable solvent, such as tetrahydrofuran, in the presence of a catalyst, such as Lindlar catalyst or palladium on carbon and, if desired, a suitable compound which disrupts the actions of the catalyst, such as quinoline or pyridine. This mixture is stirred under an atmosphere of hydrogen from about 1 to 24 hours at room temperature. The resulting alkenylaniline (2c) can be isolated by removing the solvent, for example by evaporation under reduced pressure, and further purified, if desired, by standard methods such as chromatography, crystallization, or distillation.

mide is deprotected under conditions known to one of skill in the art to provide the desired para-cycloalkylmethylanilines.

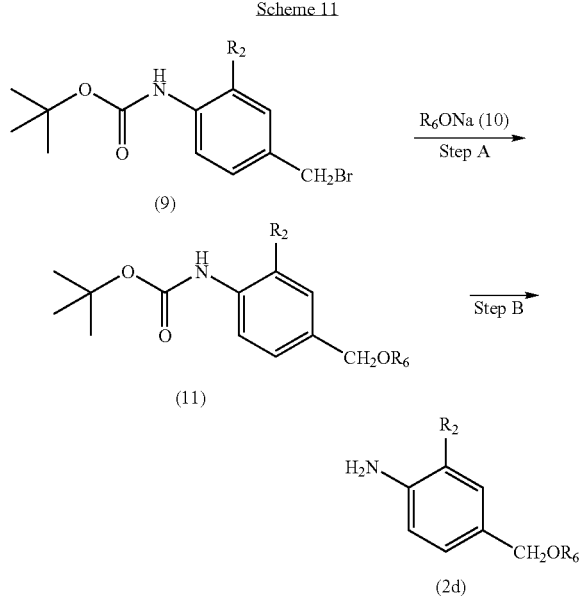

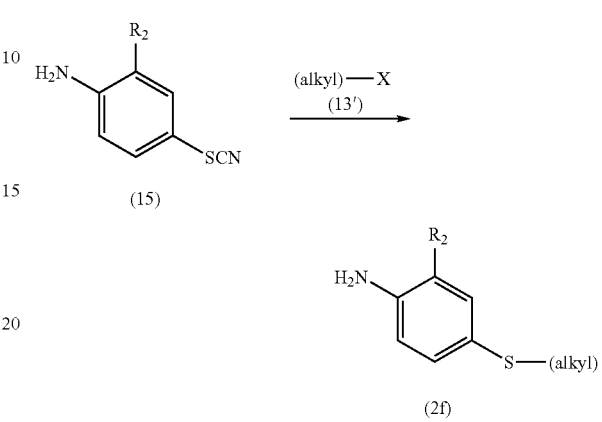

In Scheme 11, Step A, an alkoxide (10) is reacted with a 4-tert-butoxycarbonylamino-3-substituted-benzyl bromide (9), such as 4-tert-butoxycarbonylamino-3-fluorobenzyl bromide (*J. Med. Chem.*, 2000; 43:5017). In Step B, the BOC protecting group of compound of structure (11) is hydrolized with, for example, TFA, to provide the desired aniline (2d).

Step B, compound (14) is reduced via hydrogenation in the presence of a metal catalyst, such as palladium on carbon, in an atmosphere of hydrogen to provide the desired aniline (2e).

In Scheme 12, a suitable 4-(aminophenyl)thiocyanate (15), is alkylated with a compound of structure (13') in the presence of a suitable nucleophilic base to provide an alkylthio compound of structure (2f). After reaction under standard conditions to form the diphenylamine (3), wherein $R_4$ is —S—(alkyl), as in Scheme 1 above, this compound is then oxidized to the corresponding sulfonyl compound, also generally, the diphenylamine (3), wherein $R_4$ is —SO$_2$—(alkyl).

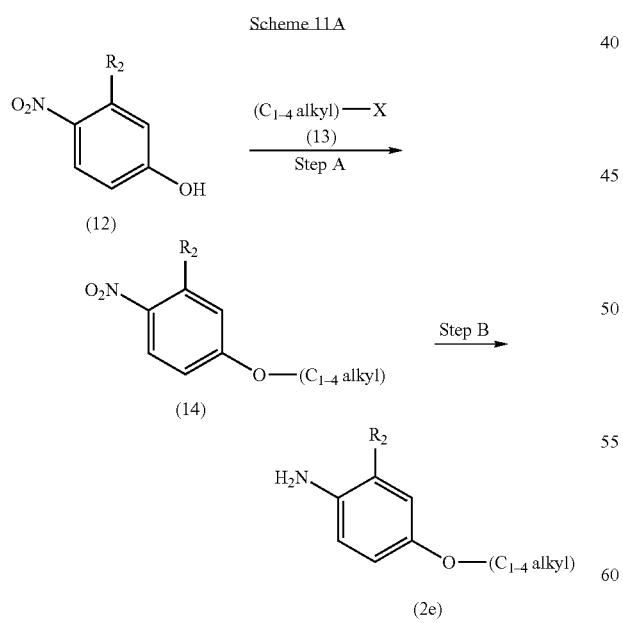

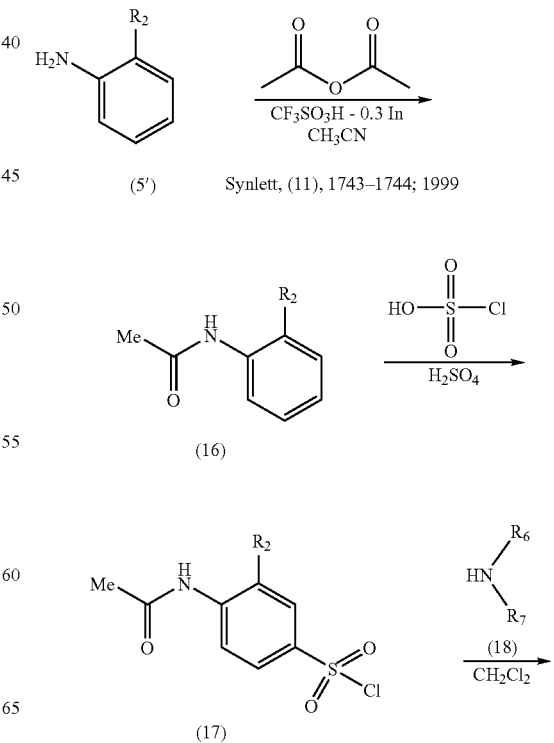

In Scheme 11A, Step A, a suitable 3-substituted-4-nitrophenol (12), such as 3-fluoro-4-nitrophenol, is alkylated with a compound of structure (13) in the presence of a suitable base to provide a compound of structure (14). In

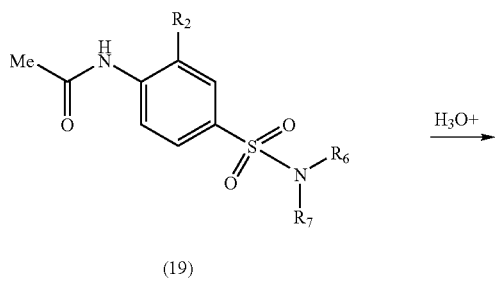

(19)

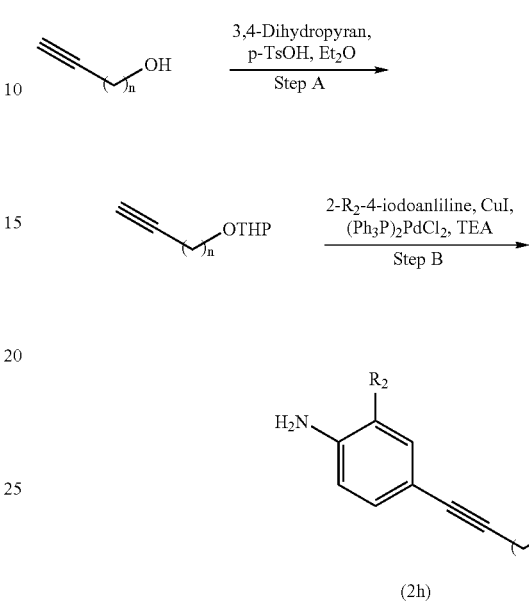

In Scheme 12A, the proper ortho-substituted or unsubstituted aniline (5') is acetylated with acetic anhydride in the presence of trifluoromethanesulfonic acid indium salt to give the protected aniline (16). Chlorosulfonation in the typical manner, as known in the art, gives the sulfonyl chloride derivative (17) which is reacted with an excess of a suitable amine (18) in a solvent such as dichloromethane or dichloroethane to give the protected para-aminobenzenesulfonamide (19). Acid-mediated deprotection in the appropriate solvent gives the desired aniline (2g).

Alternatively, the desired aniline (2g) wherein $R_2$ is methyl, fluorine or chlorine, using compound (17) as the starting material can be prepared. Where $R_2$ is fluorine, the sulfonyl chloride derivative (17) is a compound known in the literature (German Patent DE 2630060, 1978). Similarly, where $R_2$ is methyl, the sulfonyl chloride derivative (17) is also known in the literature (German Patent. DE 2750170, 1978). Finally, the sulfonyl chloride derivative (20) where $R_2$ is chlorine is commercially available.

In addition to the procedure described in Scheme 12A, one of ordinary skill in the art would appreciate that there are numerous ways of acetylating anilines. For example, heating the aniline and acetic anhydride together in a suitable solvent, such as acetic acid, would achieve the same result.

As in Scheme 7, Step A above, the compounds of Formula I, wherein $R_4$ is —C≡C—$(CH_2)_n$OH are prepared via the Sonogashira coupling with a suitable 4-iodoaniline, such as 2-fluoro-4-iodoaniline, and an appropriately substituted acetylene, as shown in Scheme 13 above. After reaction with aniline (2h) under standard conditions to form the diphenylamine, as in Scheme 1 above, hydrolysis of the tetrahydropyranyl-protecting group under conditions known in the art provides the desired compounds.

As in Scheme 7, Step A above, the compounds of Formula I, wherein $R_4$ is —$(CH_2)_m OR_6$, $R_6$=H or —C≡C$(CH_2)_n$OH, are prepared via the Sonogashira coupling with a suitable 4-iodoaniline, such as 2-fluoro-4-iodoaniline, and an appropriately substituted acetylene, as shown in Scheme 13 above. After reaction with aniline (2h) under standard conditions to form the diphenylamine, as in Scheme 1 above, and hydrolysis of the tetrahydropyranyl-protecting group under conditions known in the art, reduction via hydrogenation under the conditions as in Scheme 7, Steps B and C above, provides the desired compounds.

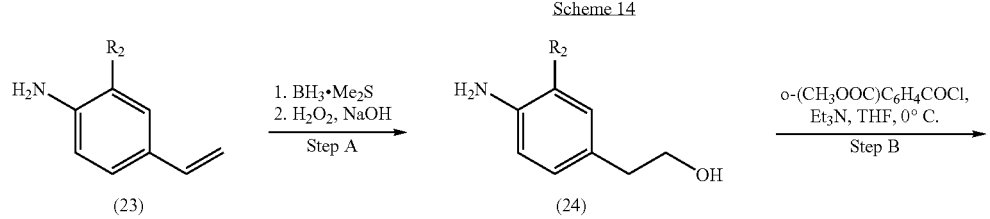

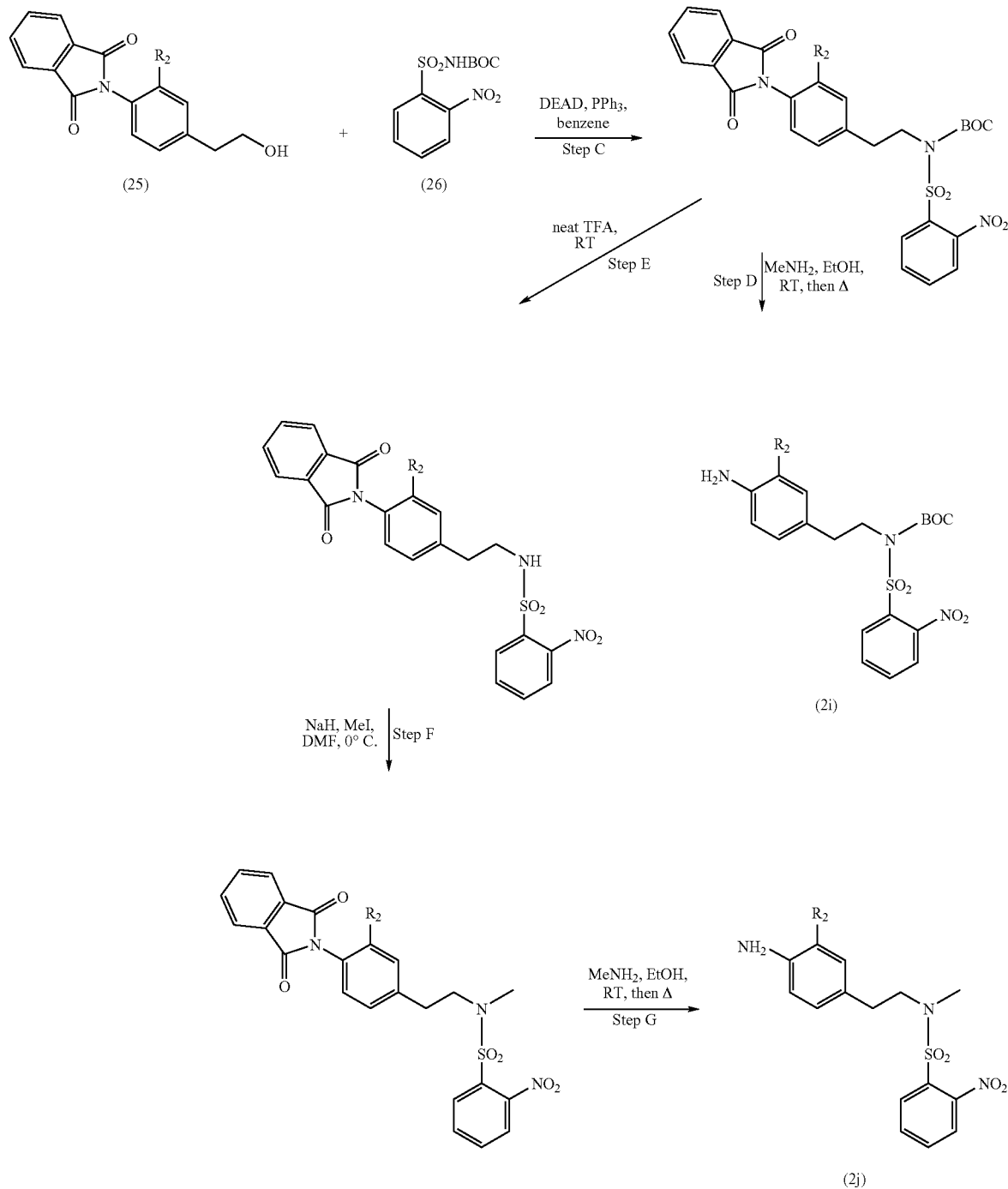

In Scheme 14, Step A, a suitable phenethyl alcohol (24) is prepared from a suitable 2-substituted-4-vinylaniline (23), such as 2-fluoro-4-vinylaniline (*Tetrahedron Letters,* 1997; 38:7433), by hydroboration and oxidation. The alcohol (24) is protected as the phthalimide (25) in Step B followed by the Mitsunobu reaction in Step C with the compound of structure (26), which is N-BOC-2-nitrobenzenesulfonamide (*Synlett,* 1999:1301). The anilines (2i) and (2j) are provided by deprotection of the phthalimide, as shown in Step D or alternatively, alkylation (*Tetrahedron Letters,* 1997; 38:5831), as shown in Step E and F, followed by deprotection of the phthalimide, as in Step G.

After reaction of the anilines (2i) and (2j) of Scheme 14, under the conditions as generally described in Scheme 1 above, a final deprotection (*Synlett,* 1999; 1301) provides the compounds of Formula 1 wherein $R_4$ is —$CH_2CH_2NH_2$ or —$CH_2CH_2NHCH_3$.

Scheme 15

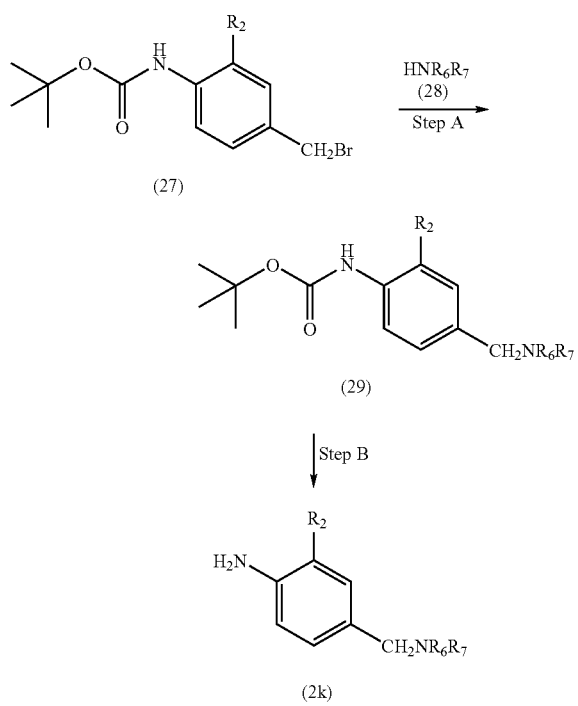

In Scheme 15, Step A, a suitable amine (28) is reacted with a 4-tert-butoxycarbonylamino-3-substituted-benzyl bromide (27), such as 4-tert-butoxycarbonylamino-3-fluorobenzyl bromide (*J. Med. Chem.* 2000; 43; 5017), followed by hydrolysis of the BOC protecting group of the compound of structure (29) with, for example, TFA in Step B to provide the compound of structure (2k).

The compounds of Formula I, wherein $R_4$ is $(CH_2)_qCF_3$ and q is 0 are prepared according to the general procedure of Scheme 1 where the suitable aniline (2) is the appropriate 4-trifluoromethylaniline (e.g., 2-fluoro; *J. Org. Chem.*, 1985; 50:457).

Scheme 16

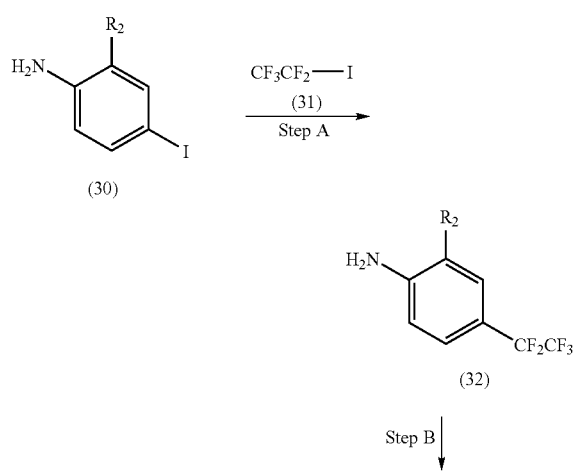

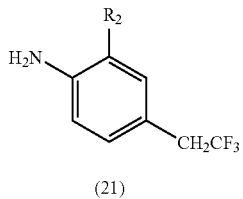

In Scheme 16, Step A, the compounds of structure (32) are prepared by an Ullmann condensation of a suitable 4-iodoaniline, such as 2-fluoro-4-iodoaniline, with a perfluoroalkyl iodide (31) (e.g., N. Yoshino et. al., *Bull. Chem. Soc. Jpn*, 1992; 65:2141).

In Scheme 16, Step B, the desired anilines (21) are prepared from compound (32) by reductive removal of the benzylic fluorine atoms with a suitable reducing agent, such as LiAlH$_4$ (*Tetrahedron Letters*, 1996; 37:4655).

Scheme 17

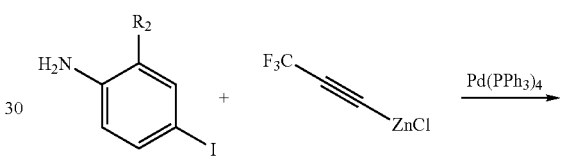

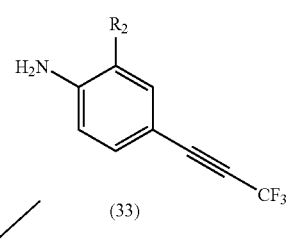

In Scheme 17, the compounds of Formula I, $R_4$ is —C≡CCF$_3$ are prepared by Negishi coupling with 3,3,3-trifluoropropynyl zinc chloride (e.g. *J. Fluorine Chem.*, 1987; 36:313 and 1992; 56:175).

In Scheme 17, the compounds of Formula I, wherein $R_4$ is —(CH$_2$)$_q$CF$_3$ or —CH═CHCF$_3$ and q is 2 are prepared by reduction of the analogous alkynes (33). Selective reduction of the alkynes (33) according to the general procedure of Scheme 7, Step C, provides the analogous alkenes.

Scheme 18

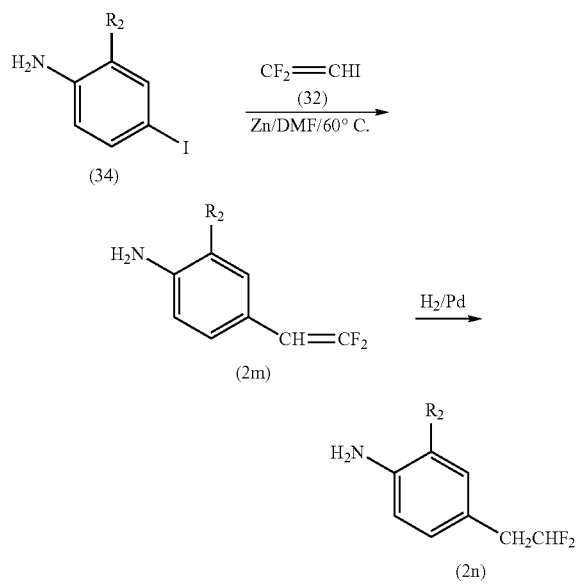

In Scheme 18, the compounds of Formula I where R<sub>4</sub> is —CH<sub>2</sub>CHCF<sub>2</sub>, or —CH═CF<sub>2</sub> are provided by a synthetic route based on the procedure of *J. Org. Chem.*, 1997; 62:7758. Thus, reaction of a suitable aniline (34), such 2-fluoro-4-iodoaniline with a suitable ethylene (35), such as 2,2-difluoroiodoethylene, and zinc provides 4-(2,2-difluorovinyl)-2-substituted-aniline (2m), which is reduced via hydrogenation in the presence of a metal catalyst, such as palladium on carbon, in an atmosphere of hydrogen to provide 4-(2,2-difluoroethyl)-2-substituted-aniline (2n).

Scheme 19

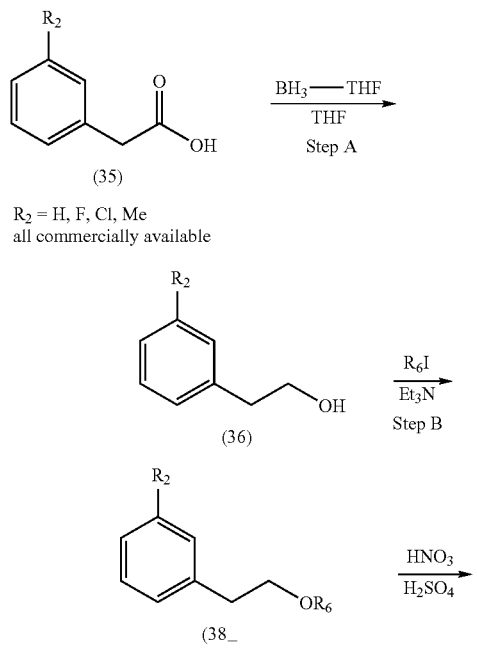

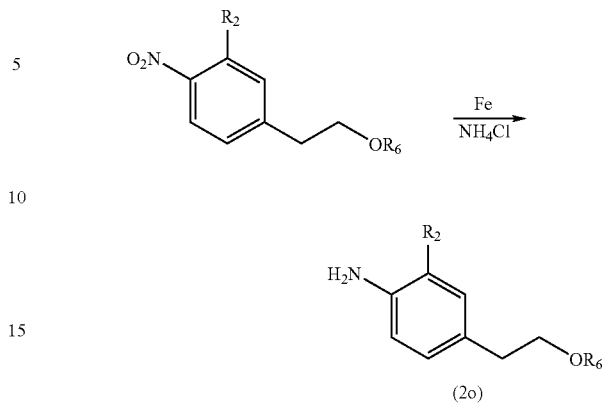

In Scheme 19, Step A, a suitable acetic acid (35), such as phenylacetic acid, 3-fluorophenylacetic acid, 3-chlorophenylacetic acid, and 3-methylphenylacetic acid, which are commercially available, is reduced to the respective alcohol (36) with borane-tetrahydrofuran complex. Alkylation of the primary alcohol in Step B with a suitable alkyl iodide (37) forms an ether (38), which is followed by nitration and mild iron reduction of the nitro group to provide the desired aniline (2o).

Scheme 20

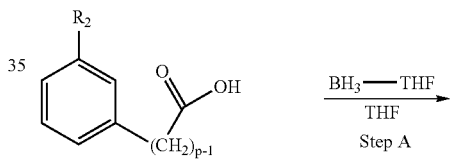

R<sub>2</sub> = H, F, Cl, Me
all commercially available
for phenylproprionic acids (p = 3). Only
R<sub>2</sub> = H available for phenylbutyric acid (p = 4)

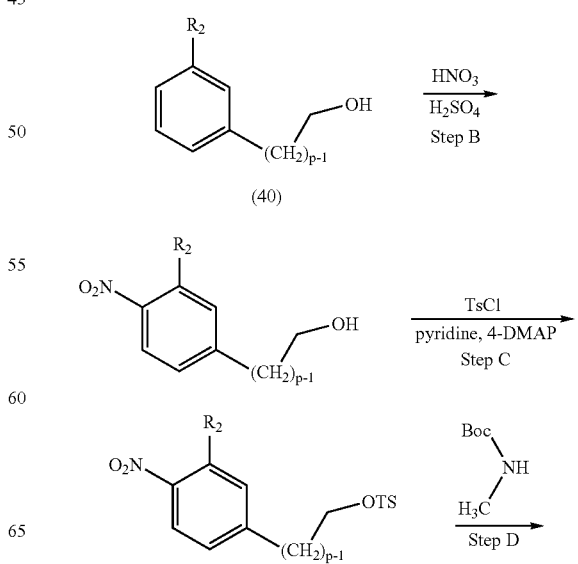

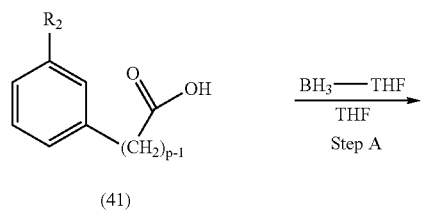

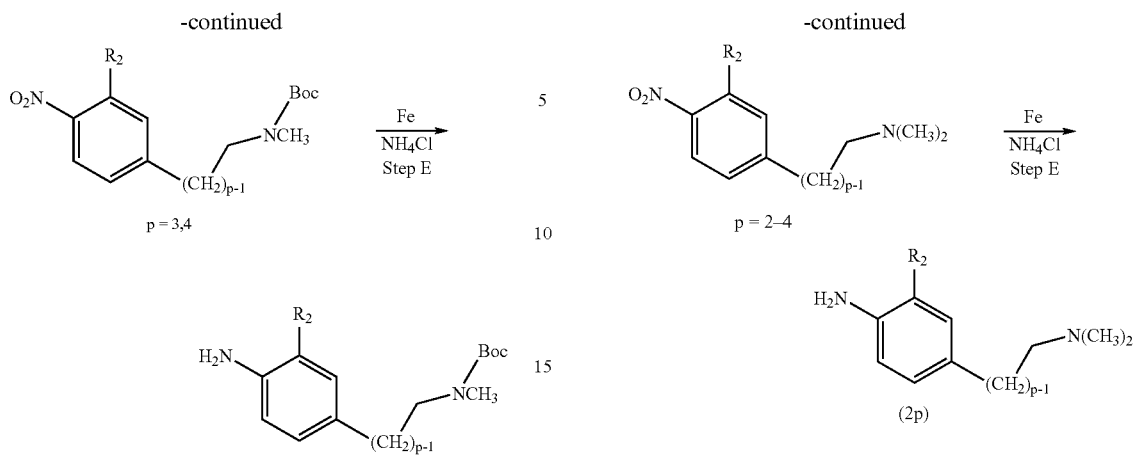

In Scheme 20, a suitable phenylproprionic acid or phenylbutyric acid (39) is reduced with borane-tetrahydrofuran in Step A to give the corresponding alcohol (40). Aromatic nitration in Step B, followed by tosylation of the primary alcohol in Step C, displacement with the BOC-protected monomethylamine in Step D, and reduction of the nitro group with iron under mildly acidic conditions in Step E provides the desired aniline. The Boc-protecting group is removed after formation of the Boc-protected desired diphenylamine product.

Scheme 21

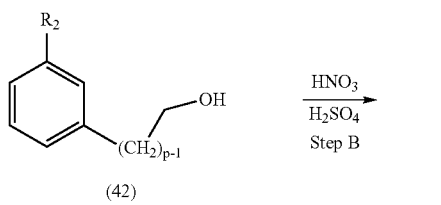

(41)

$R_2$ = H, F, Cl, Me
all commercially available

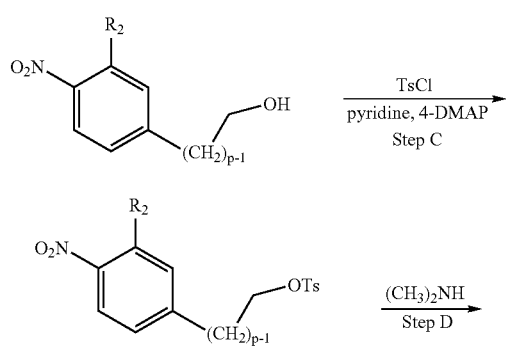

In Scheme 21, Step A, the proper acid starting material (41) is reduced with borane-tetrahydrofuran to the primary alcohol (42). Aromatic nitration in Step B is followed by tosylation of the alcohol in Step C, displacement of tosylate with dimethylamine in Step D, and iron reduction of the nitro group in Step E provides the desired aniline (2p).

Scheme 22

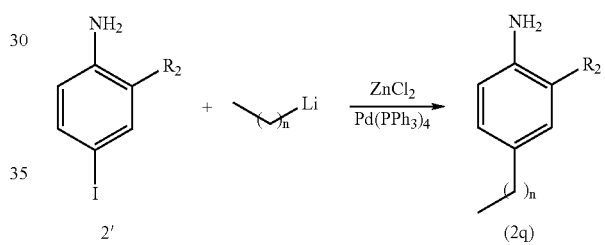

Scheme 22 demonstrates the Negishi coupling procedure, which is known to one of ordinary skill in the art.

The present invention also provides compounds of Formula I, wherein:

$R_2$ is hydrogen, fluorine, or chlorine; or $R_2$ is fluorine or chlorine; or $R_2$ is fluorine;

$R_4$ is $C_{1-6}$ alkyl, $C_{2-3}$ alkenyl, $C_{2-3}$ alkynyl, —$(CH_2)_mOR_6$, —S—($C_{1-2}$ alkyl) or —$SO_2CH_3$; or $R_4$ is $C_{1-3}$ alkyl; or $R_4$ is ethyl; or $R_4$ is $C_{2-4}$ alkenyl or $C_{2-3}$ alkynyl; or $R_4$ is vinyl; or $R_4$ is —$(CH_2)_mOR_6$; or $R_4$ is —$(CH_2)_qCF_3$, —$CH_2CHCF_2$, or —CH=$CF_2$; or $R_5$ is hydrogen.

Also provided by the present invention are compounds of the formula

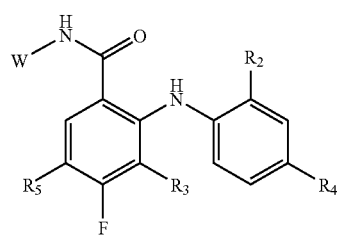

wherein
W is

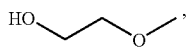 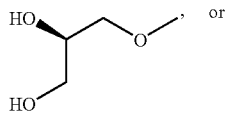

$R_2$ is hydrogen, fluorine, or chlorine;
$R_3$ is hydrogen or fluorine;
$R_4$ is $C_{1-6}$ alkyl, $C_{2-4}$ alkenyl, $C_{2-6}$ alkynyl, —S—($C_{1-2}$ alkyl), —SO$_2$CH$_3$, —C≡C—(CH$_2$)$_n$NH$_2$, —(CH$_2$)$_m$NH$_2$, —(CH$_2$)$_m$NHCH$_3$, —(CH$_2$)$_m$N(CH$_3$)$_2$, or —(CH$_2$)$_m$OR$_8$, wherein the $C_{1-6}$ alkyl and $C_{2-6}$ alkynyl are optionally substituted with between 1 and 3 substituents selected from hydroxy and alkyl;
m is 1 to 4;
n is 1 to 2;
q is 0 to 2;
$R_5$ is hydrogen or chlorine;
$R_6$ and $R_7$ are each independently hydrogen, methyl, or ethyl;
$R_8$ is independently methyl or ethyl;

and pharmaceutically acceptable salts thereof.

Additionally provided by the present invention are compounds of the formula

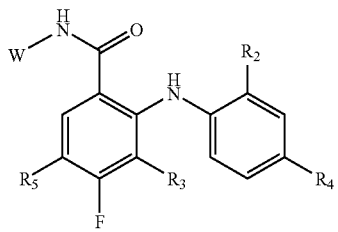

wherein
W is

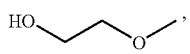 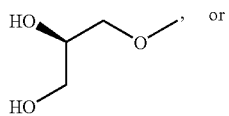

$R_2$ is fluorine, or chlorine;
$R_3$ is hydrogen or fluorine;
$R_4$ is $C_{1-4}$ alkyl, $C_{2-3}$ alkenyl, $C_{2-4}$ alkynyl, —S—($C_{1-2}$ alkyl), —SO$_2$CH$_3$, —C≡C—(CH$_2$)$_n$NH$_2$, or —(CH$_2$)$_m$OR$_8$, wherein the $C_{1-4}$ alkyl and $C_{2-4}$ alkynyl are optionally substituted with between 1 and 3 substituents selected from hydroxy and alkyl;

m is 1 to 4;
n is 1 to 2;
q is 0 to 2;
$R_5$ is hydrogen or chlorine;
$R_6$ and $R_7$ are each independently hydrogen, methyl, or ethyl;
$R_8$ is independently methyl or ethyl;

and pharmaceutically acceptable salts thereof.

Compounds of the present invention include, but are not limited to the following compounds:

2-[(4-Ethyl-2-fluorophenyl)amino]-3,4-difluoro-N-(2-hydroxyethoxy)benzamide;
2-(2-Chloro-4-ethyl-phenylamino)-3,4-difluoro-N-(2-hydroxy-ethoxy)-benzamide;
3,4-Difluoro-2-[(2-fluoro-4-vinylphenyl)amino]-N-(2-hydroxyethoxy)benzamide;
2-(2-Chloro-4-vinyl-phenylamino)-3,4-difluoro-N-(2-hydroxy-ethoxy)-benzamide;
2-[(4-Ethynyl-2-fluorophenyl)amino]-3,4-difluoro-N-(2-hydroxyethoxy)benzamide;
3,4-Difluoro-N-(2-hydroxyethoxy)-2-[[4-(hydroxymethyl)phenyl]amino]benzamide;
3,4-Difluoro-2-[[2-fluoro-4-(3-methoxypropyl)phenyl]amino]-N-(2-hydroxyethoxy)benzamide;
3,4-Difluoro-2-[[2-fluoro-4-(methylthio)phenyl]amino]-N-(2-hydroxyethoxy)benzamide;
3,4-Difluoro-2-[[2-fluoro-4-(ethylthio)phenyl]amino]-N-(2-hydroxyethoxy)benzamide;
3,4-Difluoro-2-[[2-fluoro-4-(methylsulfonyl)phenyl]amino]-N-(2-hydroxyethoxy)benzamide;
N-[(R−)2,3-Dihydroxy-propoxy]-2-(4-ethyl-2-fluoro-phenylamino)-3,4-difluoro-benzamide;
2-(4-Ethyl-2-fluoro-phenylamino)-3,4-difluoro-N-(2-hydroxy-1-hydroxymethyl-ethoxy)-benzamide;
3,4-Difluoro-2-(2-fluoro-4-methylanilino)-N-(2-hydroxyethoxy)benzamide;
2-(4-Allyl-2-fluoroanilino)-3,4-difluoro-N-(2-hydroxyethoxy)benzamide;
2-(2-Chloro-4-ethynyl-phenylamino)-3,4-difluoro-N-(2-hydroxy-ethoxy)-benzamide;
2-[4-(3-Amino-1-propynyl)-2-fluoroanilino]-3,4-difluoro-N-(2-hydroxyethoxy)benzamide;
3,4-Difluoro-2-[2-fluoro-4-(3-hydroxy-1-propynyl)anilino]-N-(2-hydroxyethoxy)benzamide;
3,4-Difluoro-2-[2-fluoro-4-(4-hydroxy-1-butynyl)anilino]-N-(2-hydroxyethoxy)benzamide;
3,4-Difluoro-2-[2-fluoro-4-(3-hydroxy-3-methyl-1-butynyl)anilino]-N-(2-hydroxyethoxy)benzamide;
3,4-Difluoro-2-[2-fluoro-4-(3-hydroxy-3-methyl-1-pentynyl)anilino]-N-(2-hydroxyethoxy)benzamide;
2-[4-(3-Aminopropyl)-2-fluoroanilino]-3,4-difluoro-N-(2-hydroxyethoxy)benzamide;
2-{4-[3-(Dimethylamino)propyl]-2-fluoroanilino}-3,4-difluoro-N-(2-hydroxyethoxy)benzamide;
3,4-Difluoro-2-{2-fluoro-4-[3-(methylamino)propyl]anilino}-N-(2-hydroxyethoxy)benzamide;
3,4-Difluoro-2-[2-fluoro-4-(hydroxymethyl)anilino]-N-(2-hydroxyethoxy)benzamide;
3,4-Difluoro-2-[2-fluoro-4-(2-hydroxyethyl)anilino]-N-(2-hydroxyethoxy)benzamide;
3,4-Difluoro-2-[2-fluoro-4-(3-hydroxypropyl)anilino]-N-(2-hydroxyethoxy)benzamide;
3,4-Difluoro-2-[2-fluoro-4-(4-hydroxybutyl)anilino]-N-(2-hydroxyethoxy)benzamide;
2-[4-(2,3-Dihydroxypropyl)-2-fluoroanilino]-3,4-difluoro-N-(2-hydroxyethoxy)benzamide;

3,4-Difluoro-2-[2-fluoro-4-(3-hydroxy-3-methylbutyl) anilino]-N-(2-hydroxyethoxy)benzamide;
3,4-Difluoro-2-[2-fluoro-4-(3-hydroxy-3-methylpentyl) anilino]-N-(2-hydroxyethoxy)benzamide;
3,4-Difluoro-2-(2-fluoro-4-propylanilino)-N-(2-hydroxyethoxy)benzamide; and
2-(4-Butyl-2-fluoroanilino)-3,4-difluoro-N-(2-hydroxyethoxy)benzamide.

Also provided by the present invention are compounds which include, but are not limited to the following compounds:
2-(4-Ethyl-2-fluoro-phenylamino)-3,4-difluoro-N-(2-hydroxy-ethoxy)-benzamide;
N-((R)-2,3-Dihydroxy-propoxy)-2-(4-ethyl-2-fluoro-phenylamino)-3,4-difluoro-benzamide;
N-((S)-2,3-Dihydroxy-propoxy)-2-(4-ethyl-2-fluoro-phenylamino)-3,4-difluoro-benzamide;
2-(4-Ethyl-2-fluoro-phenylamino)-3,4-difluoro-N-(2-hydroxy-1-hydroxymethyl-ethoxy)-benzamide;
2-(4-Ethyl-2-methyl-phenylamino)-3,4-difluoro-N-(2-hydroxy-ethoxy)-benzamide;
2-(2-Chloro-4-ethyl-phenylamino)-3,4-difluoro-N-(2-hydroxy-ethoxy)-benzamide;
5-Chloro-2-(4-ethyl-2-fluoro-phenylamino)-3,4-difluoro-N-(2-hydroxy-ethoxy)-benzamide;
5-Chloro-2-(4-ethyl-2-methyl-phenylamino)-3,4-difluoro-N-(2-hydroxy-ethoxy)-benzamide;
5-Chloro-2-(2-chloro-4-ethyl-phenylamino)-3,4-difluoro-N-(2-hydroxy-ethoxy)-benzamide;
2-(4-Ethynyl-2-fluoro-phenylamino)-3,4-difluoro-N-(2-hydroxy-ethoxy)-benzamide; 2-(4-Ethynyl-2-methyl-phenylamino)-4-fluoro-N-(2-hydroxy-ethoxy)-benzamide;
N-((R)-2,3-Dihydroxy-propoxy)-2-(4-ethynyl-2-fluoro-phenylamino)-3,4-difluoro-benzamide;
N-((S)-2,3-Dihydroxy-propoxy)-2-(4-ethynyl-2-fluoro-phenylamino)-3,4-difluoro-benzamide;
2-(4-Ethynyl-2-fluoro-phenylamino)-3,4-difluoro-N-(2-hydroxy-1-hydroxymethyl-ethoxy)-benzamide;
2-(4-Ethynyl-2-methyl-phenylamino)-3,4-difluoro-N-(2-hydroxy-ethoxy)-benzamide;
2-(2-Chloro-4-ethynyl-phenylamino)-3,4-difluoro-N-(2-hydroxy-ethoxy)-benzamide;
5-Chloro-2-(4-ethynyl-2-fluoro-phenylamino)-3,4-difluoro-N-(2-hydroxy-ethoxy)-benzamide;
5-Chloro-2-(4-ethynyl-2-methyl-phenylamino)-3,4-difluoro-N-(2-hydroxy-ethoxy)-benzamide;
5-Chloro-2-(2-chloro-4-ethynyl-phenylamino)-3,4-difluoro-N-(2-hydroxy-ethoxy)-benzamide;
3,4-Difluoro-2-(2-fluoro-4-methyl-phenylamino)-N-(2-hydroxy-ethoxy)-benzamide;
3,4-Difluoro-2-(2-fluoro-4-propyl-phenylamino)-N-(2-hydroxy-ethoxy)-benzamide;
3,4-Difluoro-2-(2-fluoro-4-isopropyl-phenylamino)-N-(2-hydroxy-ethoxy)-benzamide;
2-(4-Cyclopropyl-2-fluoro-phenylamino)-3,4-difluoro-N-(2-hydroxy-ethoxy)-benzamide;
2-(4-Butyl-2-fluoro-phenylamino)-3,4-difluoro-N-(2-hydroxy-ethoxy)-benzamide;
3,4-Difluoro-2-(2-fluoro-4-isobutyl-phenylamino)-N-(2-hydroxy-ethoxy)-benzamide;
2-(4-sec-Butyl-2-fluoro-phenylamino)-3,4-difluoro-N-(2-hydroxy-ethoxy)-benzamide;
2-(4-Cyclobutyl-2-fluoro-phenylamino)-3,4-difluoro-N-(2-hydroxy-ethoxy)-benzamide;
2-(4-tert-Butyl-2-fluoro-phenylamino)-3,4-difluoro-N-(2-hydroxy-ethoxy)-benzamide;
3,4-Difluoro-2-(2-fluoro-4-pentyl-phenylamino)-N-(2-hydroxy-ethoxy)-benzamide;
3,4-Difluoro-2-[2-fluoro-4-(1-methyl-butyl)-phenylamino]-N-(2-hydroxy-ethoxy)-benzamide;
2-[4-(1-Ethyl-propyl)-2-fluoro-phenylamino]-3,4-difluoro-N-(2-hydroxy-ethoxy)-benzamide;
2-[4-(2,2-Dimethyl-propyl)-2-fluoro-phenylamino]-3,4-difluoro-N-(2-hydroxy-ethoxy)-benzamide;
3,4-Difluoro-2-[2-fluoro-4-((R)-2-methyl-butyl)-phenylamino]-N-(2-hydroxy-ethoxy)-benzamide;
3,4-Difluoro-2-[2-fluoro-4-((S)-2-methyl-butyl)-phenylamino]-N-(2-hydroxy-ethoxy)-benzamide;
3,4-Difluoro-2-[2-fluoro-4-(3-methyl-butyl)-phenylamino]-N-(2-hydroxy-ethoxy)-benzamide;
2-(4-Cyclopentyl-2-fluoro-phenylamino)-3,4-difluoro-N-(2-hydroxy-ethoxy)-benzamide;
3,4-Difluoro-2-(2-fluoro-4-hexyl-phenylamino)-N-(2-hydroxy-ethoxy)-benzamide;
2-(4-Cyclohexyl-2-fluoro-phenylamino)-3,4-difluoro-N-(2-hydroxy-ethoxy)-benzamide;
2-(4-Cyclopropylmethyl-2-fluoro-phenylamino)-3,4-difluoro-N-(2-hydroxy-ethoxy)-benzamide;
2-(4-Allyl-2-fluoro-phenylamino)-3,4-difluoro-N-(2-hydroxy-ethoxy)-benzamide;
3,4-Difluoro-2-(2-fluoro-4-vinyl-phenylamino)-N-(2-hydroxy-ethoxy)-benzamide;
3,4-Difluoro-2-(2-fluoro-4-hydroxymethyl-phenylamino)-N-(2-hydroxy-ethoxy)-benzamide;
3,4-Difluoro-N-(2-hydroxy-ethoxy)-2-(4-hydroxymethyl-phenylamino)-benzamide;
3,4-Difluoro-2-(2-fluoro-4-methoxymethyl-phenylamino)-N-(2-hydroxy-ethoxy)-benzamide;
2-(4-Ethoxymethyl-2-fluoro-phenylamino)-3,4-difluoro-N-(2-hydroxy-ethoxy)-benzamide;
3,4-Difluoro-2-[2-fluoro-4-(2-hydroxy-ethyl)-phenylamino]-N-(2-hydroxy-ethoxy)-benzamide;
3,4-Difluoro-2-[2-fluoro-4-(3-hydroxy-propyl)-phenylamino]-N-(2-hydroxy-ethoxy)-benzamide;
3,4-Difluoro-2-[2-fluoro-4-(3-methoxy-propyl)-phenylamino]-N-(2-hydroxy-ethoxy)-benzamide;
3,4-Difluoro-2-(2-fluoro-4-methoxy-phenylamino)-N-(2-hydroxy-ethoxy)-benzamide;
2-(4-Ethoxy-2-fluoro-phenylamino)-3,4-difluoro-N-(2-hydroxy-ethoxy)-benzamide;
3,4-Difluoro-2-(2-fluoro-4-propoxy-phenylamino)-N-(2-hydroxy-ethoxy)-benzamide;
2-(4-Butoxy-2-fluoro-phenylamino)-3,4-difluoro-N-(2-hydroxy-ethoxy)-benzamide;
3,4-Difluoro-2-(2-fluoro-4-methylsulfanyl-phenyl amino)-N-(2-hydroxy-ethoxy)-benzamide;
4-Fluoro-2-(2-fluoro-4-methylsulfanyl-phenylamino)-N-(2-hydroxy-ethoxy)-benzamide;
2-(4-Ethylsulfanyl-2-fluoro-phenylamino)-3,4-difluoro-N-(2-hydroxy-ethoxy)-benzamide;
3,4-Difluoro-2-(2-fluoro-4-methanesulfonyl-phenyl amino)-N-(2-hydroxy-ethoxy)-benzamide;
2-[4-(3-Amino-prop-1-ynyl)-2-fluoro-phenylamino]-3,4-difluoro-N-(2-hydroxy-ethoxy)-benzamide;
3,4-Difluoro-2-[2-fluoro-4-(3-hydroxy-prop-1-ynyl)-phenylamino]-N-(2-hydroxy-ethoxy)-benzamide;
3,4-Difluoro-2-[2-fluoro-4-(4-hydroxy-but-1-ynyl)-phenylamino]-N-(2-hydroxy-ethoxy)-benzamide;
2-[4-(2-Amino-ethyl)-2-fluoro-phenylamino]-3,4-difluoro-N-(2-hydroxy-ethoxy)-benzamide;
2-[4-(3-Amino-propyl)-2-fluoro-phenylamino]-3,4-difluoro-N-(2-hydroxy-ethoxy)-benzamide;

2-[4-(4-Amino-butyl)-2-fluoro-phenylamino]-3,4-difluoro-N-(2-hydroxy-ethoxy)-benzamide;
3,4-Difluoro-2-[2-fluoro-4-(2-methylamino-ethyl)-phenylamino]-N-(2-hydroxy-ethoxy)-benzamide;
3,4-Difluoro-2-[2-fluoro-4-(3-methylamino-propyl)-phenylamino]-N-(2-hydroxy-ethoxy)-benzamide;
3,4-Difluoro-2-[2-fluoro-4-(4-methylamino-butyl)-phenylamino]-N-(2-hydroxy-ethoxy)-benzamide;
2-(4-Dimethylaminomethyl-2-fluoro-phenylamino)-3,4-difluoro-N-(2-hydroxy-ethoxy)-benzamide;
3,4-Difluoro-2-(2-fluoro-4-sulfamoyl-phenylamino)-N-(2-hydroxy-ethoxy)-benzamide;
3,4-Difluoro-2-(2-fluoro-4-methylsulfamoyl-phenylamino)-N-(2-hydroxy-ethoxy)-benzamide;
2-(4-Dimethylsulfamoyl-2-fluoro-phenylamino)-3,4-difluoro-N-(2-hydroxy-ethoxy)-benzamide;
3,4-Difluoro-2-(2-fluoro-4-trifluoromethyl-phenylamino)-N-(2-hydroxy-ethoxy)-benzamide;
3,4-Difluoro-2-[2-fluoro-4-(2,2,2-trifluoro-ethyl)-phenylamino]-N-(2-hydroxy-ethoxy)-benzamide;
3,4-Difluoro-2-[2-fluoro-4-(3,3,3-trifluoro-propyl)-phenylamino]-N-(2-hydroxy-ethoxy)-benzamide;
3,4-Difluoro-2-[2-fluoro-4-(4,4,4-trifluoro-butyl)-phenylamino]-N-(2-hydroxy-ethoxy)-benzamide;
3,4-Difluoro-2-[2-fluoro-4-(5,5,5-trifluoro-pentyl)-phenylamino]-N-(2-hydroxy-ethoxy)-benzamide;
3,4-Difluoro-2-[2-fluoro-4-(6,6,6-trifluoro-hexyl)-phenylamino]-N-(2-hydroxy-ethoxy)-benzamide;
2-[4-(2,2-Difluoro-ethyl)-2-fluoro-phenyl amino]-3,4-difluoro-N-(2-hydroxy-ethoxy)-benzamide; and
2-[4-(2,2-Difluoro-vinyl)-2-fluoro-phenyl amino]-3,4-difluoro-N-(2-hydroxy-ethoxy)-benzamide.

As used herein, the term "patient" refers to any warm-blooded animal such as, but not limited to, a human, horse, dog, guinea pig, or mouse. Preferably, the patient is human.

The term "treating" for purposes of the present invention refers to treatment, prophylaxis or prevention, amelioration or elimination of a named condition once the condition has been established.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a therapeutically effective amount of a disclosed compound of formula I or pharmaceutical composition thereof.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount will be between about 0.1 and about 1000 mg/kg per day, preferably between about 1 and about 300 mg/kg body weight, and daily dosages will be between about 10 and about 5000 mg for an adult subject of normal weight. Commercially available capsules or other formulations (such as liquids and film-coated tablets) of 100, 200, 300, or 400 mg can be administered according to the disclosed methods.

The compounds of the present invention are preferably formulated prior to administration. Therefore, another aspect of the present invention is a pharmaceutical composition comprising a compound of Formula I and a pharmaceutically acceptable carrier. In making the compositions of the present invention, the active ingredient, such as a compound of Formula I, will usually be mixed with a carrier, or diluted by a carrier or enclosed within a carrier. Dosage unit forms or pharmaceutical compositions include tablets, capsules, pills, powders, granules, aqueous and nonaqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

The following examples represent typical syntheses of the compounds of the present invention as described generally above. These examples are illustrative only and are not intended to limit the invention in any way. The reagents and starting materials are readily available to one of ordinary skill in the art.

EXAMPLE 1

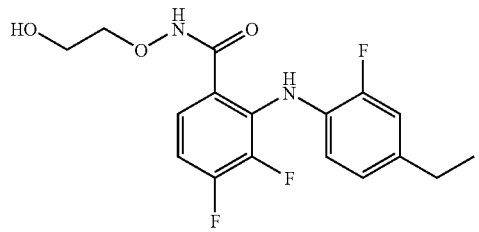

2-[(4-Ethyl-2-fluorophenyl)amino]-3,4-difluoro-N-(2-hydroxyethoxy)benzamide

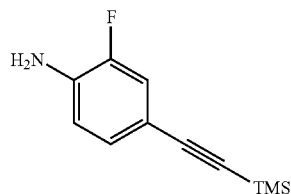

Step A: Preparation of
2-fluoro-4-[(trimethylsilyl)ethynyl]aniline

2-Fluoro-4-iodoaniline (5.00 g, 21.1 mmol), CuI (90 mg, 0.42 mmol), and (Ph$_3$P)$_2$PdCl$_2$ (300 mg, 0.42 mmol) were weighed into a flask which was sealed and flushed with N$_2$. A solution of TMS-acetylene (2.28 g, 23.2 mmol) in TEA (20 mL) was added, then the entire mixture stirred 15 hours at room temperature. The reaction mixture was diluted with diethyl ether (200 mL), filtered through Celite®, then all solvents removed under reduced pressure. The resulting dark brown oil was purified by filtration through a plug of flash silica (5% EtOAc/hexanes as eluant) to afford the desired product as a pale brown oil which rapidly solidified to give a crystalline solid (3.85 g, 88%); m.p. (EtOAc/hexanes) 45–47° C. $^1$H NMR (400 MHz, CDCl$_3$) δ 7.10 (dd, J=11.7, 1.8 Hz, 1 H), 7.06 (ddd, J=8.3, 1.8, 1.0 Hz, 1 H), 6.66 (dd, J=9.4, 8.3 Hz, 1 H), 3.86 (br s, 2 H), 0.22 (s, 9 H). Anal. Calcd for C$_{11}$H$_{14}$FNSi: C, 63.7; H, 6.8; N, 6.8. Found: C, 63.7; H, 6.9; N, 6.7.

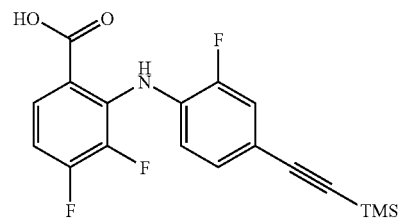

Step B: Preparation of 3,4-difluoro-2-[[2-fluoro-4 (trimethylsilylethynyl)phenyl]amino]benzoic acid A mixture of the product of Step A, 2-fluoro-4-[(trimethylsilyl)ethynyl]aniline (3.85 g, 18.6 mmol) and 2,3,4-trifluorobenzoic acid (3.27 g, 18.6 mmol) was dissolved in dry THF (25 mL). The flask was fitted with a pressure-equalising dropping funnel and the entire apparatus evacuated and flushed with N$_2$. The solution was then cooled to –78° C. (acetone/dry ice) and a solution of 1.06 M LiHMDS (52.64 mL, 55.8 mmol) was added dropwise from the dropping funnel. Following this addition, the reaction mixture was allowed to warm to room temperature and stirred for a further 15 hours. The reaction solvent was removed under reduced pressure and the resulting residue partitioned between 1 M HCl (100 mL) and EtOAc (2×100 mL). The combined EtOAc fractions were then washed with water (100 mL) and saturated NaCl (100 mL), dried (Na$_2$SO$_4$), and the EtOAc removed under reduced pressure to afford a crude product which was purified by chromatography on flash silica (10% EtOAc/hexanes as eluant), giving the desired product as a pale yellow solid (3.99 g, 59%); m.p. (EtOAc/hexanes) 164–167° C. $^1$H NMR [400 MHz, (CD$_3$)$_2$SO] δ 13.70 (br s, 1 H), 9.31 (br s, 1 H), 7.82 (ddd, J=9.1, 6.1, 2.0 Hz, 1 H), 7.34 (dd, J=12.0, 1.9 Hz, 1 H), 7.18 (ddd, J=8.3, 1.9, 0.8 Hz, 1 H), 7.16 (td, J=9.5, 7.3 Hz, 1 H), 6.93 (ddd, J=8.9, 8.3, 5.4 Hz, 1 H), 0.22 (s, 9 H). Anal. Calcd for C$_{18}$H$_{16}$F$_3$NO$_2$Si: C, 59.5; H, 4.4; N, 3.9. Found: C, 59.7; H, 4.7; N, 3.9.

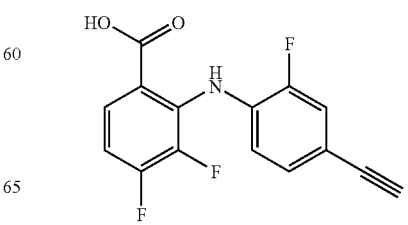

Step C: Preparation of 3,4-difluoro-2-[(4-ethynyl-2-fluorophenyl)amino]benzoic acid The product of Step B, 3,4-difluoro-2-[[2-fluoro-4-(trimethylsilylethynyl)phenyl]amino]benzoic acid (3.99 g, 11.0 mmol), was dissolved in MeOH (200 mL), to which was added $K_2CO_3$ (3.03 g, 22.0 mmol). This mixture was stirred at room temperature for 15 hours, then the reaction solvent removed under reduced pressure. The resulting residue was dissolved in water (50 mL), to which was added 1 M HCl until the pH=4. The resulting pale brown precipitate was collected by filtration and dried to afford the desired product (3.17 g, 99%); m.p. (EtOAc/hexanes) 160–162° C. $^1$H NMR [400 MHz, $(CD_3)_2SO$] δ 13.70 (br s, 1 H), 9.24 (br s, 1 H), 7.82 (ddd, J=9.2, 6.1, 2.1 Hz, 1 H), 7.38 (dd, J=12.0, 1.9, 1 H), 7.21 (ddd, J=8.4, 1.9, 0.8 Hz, 1 H), 7.16 (td, J=9.5, 7.3 Hz, 1 H), 6.96 (ddd, J=8.9, 8.4, 5.4 Hz, 1 H), 4.15 (s, 1 H). Anal. Calcd for $C_{15}H_8F_3NO_2$: C, 62.4; H, 3.1; N, 4.7. Found: C, 62.4; H, 3.2; N, 4.6.

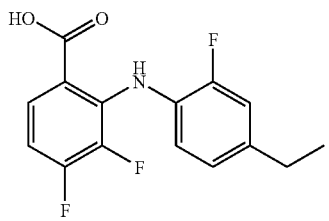

Step D: Preparation of 2-[(4-ethyl-2-fluorophenyl)amino]-3,4-difluorobenzoic acid The product of Step C, 3,4-difluoro-2-[(4-ethynyl-2-fluorophenyl)amino]benzoic acid (300 mg, 1.03 mmol), was dissolved in absolute ethanol (30 mL) and 5% Pd/C (30 mg) added. This mixture was stirred under an atmosphere of hydrogen (60 psi) for 2 hours at room temperature. The Pd/C was removed over Celite®, which was washed well with additional ethanol, then the solvent removed from the resultant filtrate under reduced pressure to afford 2-[(4-ethyl-2-fluorophenyl)amino]-3,4-difluorobenzoic acid as an off-white solid (280 mg, 92%); m.p. (EtOAc/hexanes) 199–201° C. $^1$H NMR [400 MHz, $(CD_3)_2SO$] δ 14.10 (br s, 1 H), 9.31 (br s, 1 H), 7.80 (ddd, J=8.5, 6.1, 1.9 Hz, 1 H), 7.09 (dd, J=12.4, 1.5 Hz, 1 H), 7.04–6.92 (m, 3 H), 2.52 (q, J=7.6 Hz, 2 H), 1.17 (t, J=7.5 Hz, 3 H).

Step E: Preparation of 2-[(4-ethyl-2-fluorophenyl)amino]-3,4-difluoro-N-(2-hydroxyethoxy)benzamide The title compound was prepared from the reaction of the product of Step D, 2-[(4-ethyl-2-fluorophenyl)amino]-3,4-difluorobenzoic acid (93 mg, 0.32 mmol) dissolved in dry THF (5 mL), and carbonyldiimidazole (CDI) (102 mg, 0.63 mmol). Within 10 minutes, a bright yellow solution was obtained and conversion to the imidazolide was confirmed by TLC (50% EtOAc/hexanes). A solution of 2-(aminooxy) ethanol (97 mg, 1.26 mmol) in THF (5 mL) was then added and the mixture stirred for 15 hours at room temperature. The reaction solvent was removed under reduced pressure and the residue partitioned between 1 M HCl (50 mL) and EtOAc (50 mL). The EtOAc layer was then washed with water (50 mL) and saturated NaCl solution (50 mL), dried ($Na_2SO_4$), and the solvent removed under reduced pressure to afford an oil which was purified by flash column chromatography on silica gel (50% EtOAc/hexanes) to give 2-[(4-ethyl-2-fluorophenyl)amino]-3,4-difluoro-N-(2-hydroxyethoxy)benzamide as a cream solid (65%); m.p. (EtOAc/hexanes) 134–138° C. $^1$H NMR [400 MHz, $(CD_3)_2SO$] δ 11.84 (br s, 1 H), 8.76 (br s, 1 H), 7.43–7.37 (m, 1 H), 7.14–7.02 (m, 2 H), 6.90 (dd, J=8.3, 1.5 Hz, 1 H), 6.83. (td, J=8.6, 4.4 Hz, 1 H), 4.70 (br s, 1 H), 3.86 (t, J=4.9 Hz, 2 H), 3.57 (t, J=4.9 Hz, 2 H), 2.54 (q, J=7.6 Hz, 2 H), 1.15 (t, J=7.6 Hz, 3 H).

EXAMPLE 2

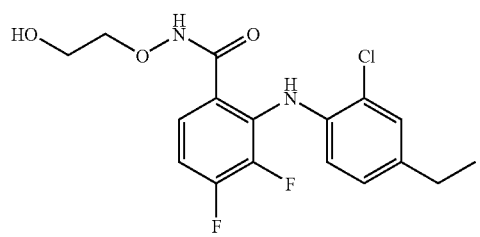

2-(2-Chloro-4-ethyl-phenylamino)-3,4-difluoro-N-(2-hydroxy-ethoxy)-benzamide

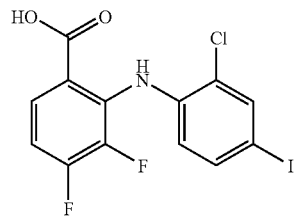

Step A: Preparation of 2-(2-chloro-4-iodophenylamino)-3,4-difluorobenzoic acid To a solution of 2,3,4-trifluorobenzoic acid (75 g, 0.426 mol) in anhydrous tetrahydrofuran at −78° C. under nitrogen was added slowly lithium bis(trimethylsilyl)amide (426 mL, 0.426 mol, 1.0 M solution in THF). The dark brown reaction mixture was stirred for 15 minutes at −65° C. (inside temp). This is referred to as Solution A.

To a solution of 2-chloro-4-iodoaniline (108 g, 0.426 mol) in anhydrous tetrahydrofuran (1000 mL) at −78° C. (outside) under nitrogen was added slowly lithium bis(trimethylsilyl)amide (852 mL, 0.852 mol, Aldrich, 1.0 M solution in THF). The dark green solution was stirred for 0.5 hours. This is referred to as Solution B.

Solution A was transferred to Solution B using positive nitrogen pressure. The reaction mixture was stirred at ambient temperature overnight. The reaction was quenched with 2.5 L dry ether (saturated with hydrogen chloride gas) until the pH was about 1.0. The precipitated solid was filtered off through Celite® and washed thoroughly with ether.

The filtrate was washed with 1N HCl (2×500 mL), brine (2×500 mL), dried and concentrated to give a light brown solid (143 g) which was crystallized from methanol (450 mL) and methylene chloride (1.25 L) to afford 2-(2-chloro-4-iodophenylamino)-3,4-difluorobenzoic acid (104 g, 60% yield) as an off-white powder: m.p. 226–227° C.; $^1$H NMR (400 MHz, DMSO-$d_6$) δ 13.83 (br s), 9.26 (s), 7.85 (ddd, J=8.9, 6.1, 1.9 Hz, 1 H), 7.81 (d, J=1.9 Hz, 1 H), 7.54 (dd, J=8.6, 1.9 Hz, 1 H), 7.18 (dt, J=7.3, 9.3 Hz, 1 H), 6.74 (dd, J=8.5, 7.1 Hz, 1 H); $^{19}$F-NMR (376 MHz, DMSO-$d_6$) δ −129.9, −141.9. Anal. Calcd/found for $C_{13}H_7NO_2F_2ClI$: C, 38.13/37.33; H, 1.72/1.60; N, 3.42/3.31.

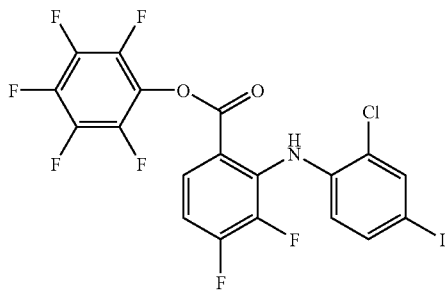

Step B: Preparation of 2-(2-chloro-4-iodophenylamino)-3,4-difluorobenzoic acid Pentafluorophenyl Ester To a solution of the product of Example 2, Step A, 2-(2-chloro-4-iodophenylamino)-3,4-difluorobenzoic acid (10.0 g, 24.4 mmol), and pyridine (2.16 mL, 26.8 mmol) in anhydrous dimethylformamide (49 mL) was added pentafluorophenyl trifluoroacetate (5.35 mL, 30.5 mmol). The resultant solution was stirred at ambient temperature for 2 hours. The reaction mixture was diluted with ethyl acetate (600 mL) and washed with 0.1 M aqueous hydrochloric acid (2×240 mL), 25% saturated aqueous sodium bicarbonate (2×240 mL), and saturated brine (240 mL). The organics were dried over anhydrous magnesium sulfate and concentrated under reduced pressure to afford an oil that was purified on silica gel. Elution with hexanes-ethyl acetate (19:1) afforded 2-(2-chloro-4-iodophenylamino)-3,4-difluorobenzoic acid pentafluorophenyl ester (12.8 g, 91%) as a pale-yellow powder: m.p. 108.5–110.0° C.; $^1$H-NMR (400 MHz, CDCl$_3$) δ 8.77 (br s, 1 H), 8.07 (br s, 1 H), 7.69 (br s, 1 H), 7.48 (br d, J=7.0 Hz, 1 H), 6.91 (br d, J=7.2 Hz, 1 H), 6.67 (br s., 1 H); $^{19}$F-NMR (376 MHz, CDCl$_3$) δ −123.74 (s, 1F), −139.17 (d, J=16.8 Hz, 1F), −152.35 (d, J=21.4 Hz, 2F), −156.96 (t, J=21.4 Hz, 1F), −161.81 (t, J=21.4 Hz, 2F). Anal. Calcd/found for $C_{19}H_6NO_2F_7ClI$: C, 39.65/39.32; H, 1.05/0.91; N, 2.43/2.35; F, 23.10/22.85; Cl, 6.16/6.92; I, 22.05/22.50.

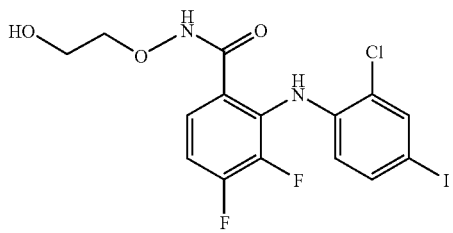

Step C: Preparation of 2-(2-chloro-4-iodo-phenylamino)-3,4-difluoro-N-(2-hydroxy-ethoxy)-benzamide To a solution of the product of Example 2, Step B, 2-(2-chloro-4-iodo-phenylamino)-3,4-difluorobenzoic acid pentafluorophenyl ester (10.0 g, 17.4 mmol), in anhydrous dimethylformamide (36 mL) was added 2-(aminooxy)-ethanol [prepared by the literature procedure: Dhanak, D.; Reese, C. B., J. Chem. Soc., Perkin Trans. 1987; 1:2829] (1.6 g, 20.8 mmol) and N,N-diisopropylethylamine (6.0 mL, 34.8 mmol). The resultant solution was stirred at ambient temperature for 16 hours. The reaction mixture was concentrated to 20% volume then diluted with ethyl acetate (360 mL). The resultant solution was washed with water (6×60 mL) and brine (2×60 mL). The organics were dried over anhydrous magnesium sulfate and concentrated under reduced pressure to afford a white solid that was purified on silica gel. Elution with ethyl acetate-methanol (9:1) afforded 2-(2-chloro-4-iodo-phenylamino)-3,4-difluoro-N-(2-hydroxy-ethoxy)-benzamide (7.31 g, 90%) as a white solid. Recrystallization from methanol afforded analytically pure material: m.p. 173–175° C.; $^1$H NMR (400 MHz, DMSO-$d_6$) δ 11.93 (br s, 1 H), 8.85 (br s, 1 H), 7.76 (d, J=1.7 Hz, 1 H), 7.48 (dd, J=8.6, 1.7 Hz, 1 H), 7.44 (dd, J=8.5, 6.2 Hz, 1 H), 7.25 (dt, J=8.5, 9.3 Hz, 1 H), 6.58 (dd, J=8.5, 6.4 Hz, 1 H), 4.70 (br s, 1 H), 3.86 (br s, 2 H), 3.56 (br d, J=3.9 Hz, 2 H); MS (APCI+)=469.0; MS (APCI−)=467.0; Anal. Calcd/found for $C_{15}H_{12}ClF_{21}N_2O_3$: C, 38.45/38.60; H, 2.58/2.53; N, 5.98/5.91; F, 8.11/8.08; I, 27.08/27.43.

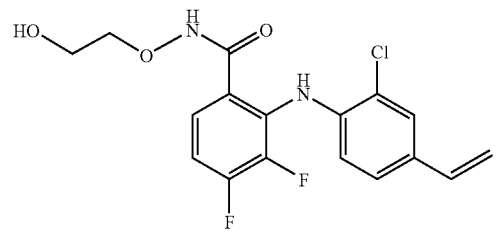

Step D: Preparation of 2-(2-chloro-4-vinyl-phenylamino)-3,4-difluoro-N-(2-hydroxy-ethoxy)-benzamide A solution of the product of Example 2, Step C, 2-(2-chloro-4-iodo-phenylamino)-3,4-difluoro-N-(2-hydroxy-ethoxy)-benzamide (2.00 g, 4.27 mmol), in 1,4-dioxane (30 mL) was twice deoxygenated using the freeze-pump-thaw technique and subsequently stirred at ambient temperature under nitrogen. Tributyl(vinyl)tin (1.37 mL, 4.68 mmol) and tetrakis(triphenylphosphine)palladium (250 mg, 0.21 mmol) were added, and the reaction mixture was gradually warmed to 95° C. over 4 hours and was stirred at 95° C. overnight under an atmosphere of nitrogen. The reaction mixture was cooled to ambient temperature and filtered through a pad of Celite®, washing the filter cake with ethyl acetate (120 mL). The combined filtrate and washings were shaken with 1 M aqueous potassium fluoride solution (25 mL). The aqueous salts were removed by filtration and the organics were further washed with 1 M aqueous potassium fluoride solution (25 mL), water (2×50 mL), and saturated aqueous brine (50 mL). The organics were dried over anhydrous magnesium sulfate and were concentrated under reduced pressure to afford a dark colored oil that was purified by silica gel chromatography. Elution with ethyl acetate afforded a yellow-colored foam (0.79 g) which was triturated with ether/hexanes to afford 2-(2-chloro-4-vinyl-phenylamino)-3,4-difluoro-N-(2-hydroxy-ethoxy)-benzamide as a straw-colored solid (0.69 g, 44% yield): $^1$H NMR (400 MHz, DMSO-$d_6$) δ 11.97 (br s, 1 H), 8.94 (br s, 1 H), 7.59 (d, J=1.7 Hz, 1 H), 7.47 (br t, J=6.4 Hz, 1 H), 7.31 (dd, J=8.3, 2.0 Hz, 1 H), 7.29–7.21 (m, 1 H), 6.77 (dd, J=8.3, 6.6 Hz, 1 H), 6.64 (dd, J=17.6, 11.0 Hz, 1 H), 5.75 (dd, J=17.6, 0.7 Hz, 1 H), 5.18 (dd, J=10.8, 0.7 Hz, 1 H), 4.73 (br s, 1 H), 3.88 (br s, 2 H), 3.58 (br s, 2 H); $^{19}$F NMR (376 MHz, DMSO-$d_6$) δ −132.5, −141.3 (d, J=20.2 Hz); MS (APCI+)=368.9. Anal. Calcd/found for $C_{17}H_{15}ClF_2N_2O_3$: C, 55.37/55.46; H, 4.10/3.91; N, 7.60/7.37.

Step E: Preparation of 2-(2-chloro-4-ethyl-phenylamino)-3,4-difluoro-N-(2-hydroxy-ethoxy)-benzamide A solution of the product of Example 2, Step D, 2-(2-chloro-4-vinyl-phenylamino)-3,4-difluoro-N-(2-hydroxy-ethoxy)-benzamide (0.291 g, 0.789 mmol) in tetrahydrofuran (16 mL) was hydrogenated over 10% palladium on carbon (0.08 g) at 6900 psig at room temperature for 17 hours. The catalyst was removed by filtration and the filtrate was concentrated in vacuo to afford a crystalline solid. The solid was dissolved in methanol and concentrated to near dryness. Ether (10 mL) was added and the mixture was allowed to stand at ambient temperature for 6 hours. during which crystallization ensued. The white crystals were filtered, washed with a small volume of ether, and dried in vacuo at 60° C. overnight yielding 2-(2-chloro-4-ethyl-phenylamino)-3,4-difluoro-N-(2-hydroxy-ethoxy)-benzamide (222 mg): m.p. 142.5–145° C.; $^1$H NMR (400 MHz, DMSO-$d_6$) δ 11.94 (br s, 1 H), 8.85 (br s, 1 H), 7.44 (br t, J=6.4 Hz, 1 H), 7.30 (d, J=2.0 Hz, 1 H), 7.22–7.15 (m, 1 H), 7.05 (dd, J=8.3, 2.0 Hz, 1 H), 6.75 (dd, J=8.3, 6.3 Hz, 1 H), 4.71 (br s, 1 H), 3.89 (br s, 2 H), 3.59 (br s, 2 H), 2.54 (q, J=7.6 Hz, 2 H), 1.15 (t, J=7.6 Hz, 3 H); $^{19}$F NMR (376 MHz, DMSO-$d_6$) δ −132.7, −142.0; MS (APCI+)=371.0. Anal. Calcd/found for $C_{17}H_{17}ClF_2N_2O_3$: C, 55.07/55.14; H, 4.62/4.51; N, 7.56/7.38; F, 10.25/9.98.

EXAMPLE 3

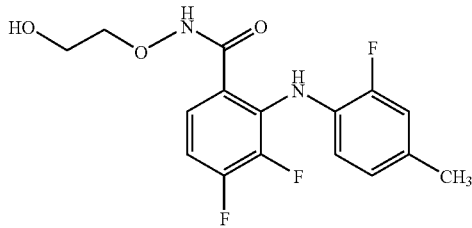

3,4-Difluoro-2-(2-fluoro-4-methylanilino)-N-(2-hydroxyethoxy)benzamide 2,3,4-Trifluorobenzoic acid and 2-fluoro-4-methylaniline were reacted in the presence of LiHMDS solution in THF by the general procedure of Example 1, Step B. After workup, 3,4-difluoro-2-[2-fluoro-4-methylanilino]benzoic acid was isolated as a crude pale brown solid which was reacted directly with 2-(aminooxy)ethanol and DMT-MM by the general procedure of Example 6, Step B below, then purified by column chromatography on silica gel (100% EtOAc as eluant) to give 3,4-difluoro-2-(2-fluoro-4-methylanilino)-N-(2-hydroxyethoxy)benzamide as a white solid (44%); m.p. (EtOAc/hexane) 134–139° C. $^1$H NMR [400 MHz, $(CD_3)_2SO$] [ ] 11.82 (v br s, 1H), 8.77 (br s, 1 H), 7.41 (ddd, J=8.1, 5.7, 1.6 Hz, 1 H), 7.13–7.00 (m, 2 H), 6.88 (dd, J=8.3, 1.1 Hz, 1 H), 6.82 (ddd, J=8.5, 8.5, 4.2 Hz, 1 H), 4.76 (v br s, 1 H), 3.86 (t, J=5.0 Hz, 2 H), 3.58 (J=5.0 Hz, 2 H), 2.25 (s, 3 H). Anal. calcd. for $C_{16}H_{15}F_3N_2O_3$: C, 56.5; H, 4.4; N, 8.2. Found C, 56.3; H, 4.5; N, 8.2.

EXAMPLE 4

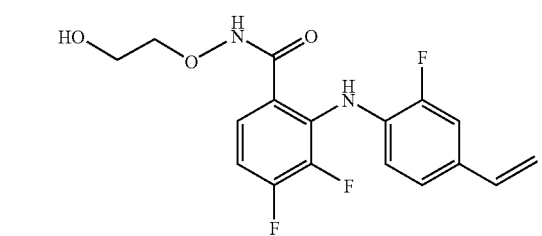

3,4-Difluoro-2-[(2-fluoro-4-vinylphenyl)amino]-N-(2-hydroxyethoxy)benzamide

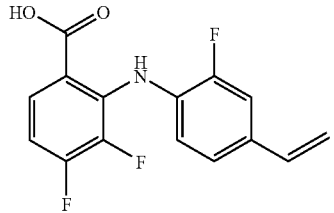

Step A: Preparation of 3,4-difluoro-2-[(2-fluoro-4-vinylphenyl)amino]benzoic acid The product of Example 1, Step C, 2-[(4-ethynyl-2-fluorophenyl)amino]-3,4-difluorobenzoic acid (540 mg, 1.86 mmol) and quinoline (220 mg) were dissolved in THF (50 mL), then Lindlar catalyst (11 mg) added. This mixture was stirred under an atmosphere of hydrogen (60 psi) for 3 periods of 15 minutes and monitored carefully by TLC (50% EtOAc/hexanes as eluant). The reaction mixture was filtered through Celite® which was washed well with EtOAc and the resulting filtrate concentrated (to 100 mL) under reduced pressure. This organic solution was then washed with 1 M HCl (2×100 mL), water (100 mL) and saturated NaCl solution (100 mL), dried ($Na_2SO_4$), and the solvent removed under reduced pressure. The resulting crude solid was purified by flash chromatography on silica (10% EtOAc/hexanes as eluant) to afford 3,4-difluoro-2-[(2-fluoro-4-vinylphenyl)amino]benzoic acid as a crystalline yellow solid (390 mg, 72%); m.p. (EtOAc/hexanes) 162–166° C. $^1$H NMR [400 MHz, $(CD_3)_2SO$] δ 13.20 (br s, 1 H), 9.30 (br s, 1 H), 7.52 (ddd, J=8.3, 6.1, 1.8 Hz, 1 H), 7.41 (dd, J=12.8, 1.7 Hz, 1 H), 7.19 (dd, J=8.3, 1.7 Hz, 1 H), 7.08 (dd, J=16.6, 9.3 Hz, 1 H), 7.00 (td, J=8.7, 5.2 Hz, 1 H), 6.67 (dd, J=17.6, 10.9 Hz, 1 H), 5.78 (d, J=17.6 Hz, 1 H), 5.22 (d, J=11.0 Hz, 1 H). Anal. Calcd for $C_{15}H_{10}F_3NO_2$: C, 61.4; H, 3.3; N, 4.9. Found C, 61.4; H, 3.4; N, 4.8.

Step B: Preparation of 3,4-difluoro-2-[(2-fluoro-4-vinylphenyl)amino]-N-(2-hydroxyethoxy)benzamide The title compound was prepared from reaction of the product of Example 4, Step A, 3,4-difluoro-2-[(2-fluoro-4-vinylphenyl)amino]benzoic acid with CDI and 2-(aminooxy)ethanol by the general procedure of Example 1, Step E, then purified by flash column chromatography on silica gel (10% EtOAc/hexanes) to give 3,4-difluoro-2-[(2-fluoro-4-vinylphenyl)amino]-N-(2-hydroxyethoxy)benzamide as a crystalline white solid (78%); m.p. (EtOAc/hexanes) 134–138° C. $^1$H NMR [400 MHz, $(CD_3)_2SO$] δ 11.85 (br s, 1 H), 8.82 (br s, 1 H), 7.45–7.38 (m, 1 H), 7.37 (dd, J=12.9, 1.8 Hz, 1 H), 7.21–7.15 (m, 1 H), 7.14 (dd, J=8.4, 1.7 Hz, 1 H), 6.83 (td, J=8.7, 4.8 Hz, 1 H), 6.65 (dd, J=17.6, 10.8 Hz, 1 H), 5.73 (d, J=17.9 Hz, 1 H), 5.18 (d, J=11.1 Hz, 1 H), 4.70 (br s, 1 H), 3.85 (t, J=4.8 Hz, 1 H), 3.56 (t, J=4.8 Hz, 2 H). Anal. Calcd for $C_{17}H_{15}F_3N_2O_3$: C, 58.0; H, 4.3; N, 8.0. Found C, 57.6; H, 4.6; N, 8.1.

EXAMPLE 4A

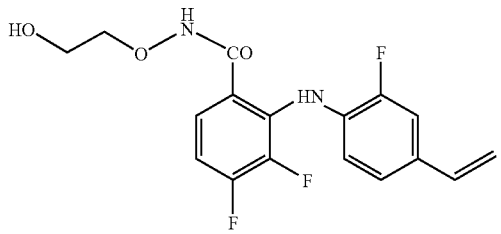

2-[(4-vinyl-2-fluorophenyl)amino]-3,4-difluoro-N-(2-hydroxy-ethoxy)benzamide

Step A: Preparation of Vinylboronic Acid

In a three-necked, round-bottomed flask equipped with a low temperature thermometer and magnetic stirrer under nitrogen was placed a solution of trimethyl borate (10 ml, 89.2 mmol) in dry THF (75 ml). The contents of the flask were cooled to −70° C. and a 1 M solution of vinylmagnesium bromide (50 ml, 50 mmol) was added dropwise over 50 minutes. The resulting solution was stirred at this temperature for an additional hour and then quenched with 1 N HCl (25 ml). The contents of the flask were allowed to warm up to ambient temperature and brine (50 ml) was added. The aqueous phase was extracted with diethyl ether (2×100 ml) and the combined organic extracts were washed with water (50 ml), brine (50 ml) and dried over $MgSO_4$. The solvent was evaporated under vacuum to a final volume of, approximately, 25 ml and this solution of vinylboronic acid was used without any further purification for the next step.

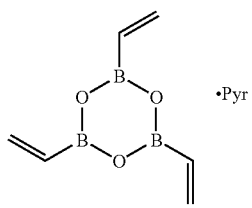

2

Step B: Preparation of Boron Complex 2

To the solution obtained in the previous step was added dry pyridine (10 ml) and the resulting mixture was stirred at ambient temperature for 18 h. The solvent was removed under vacuum and the clear, oily residue was distilled to give 3.00 g (42% yield) of a clear oil 2 (bp 50–52° C., 0.1 mm of Hg) which, after being placed in a freezer at −24° C. overnight, turned into a white solid. $^1$H NMR $(CDCl_3)$: δ 5.75–5.79 (m, 3 H), 5.91–5.99 (m, 6 H), 7.58–7.62 (m, 2 H), 7.99–8.03 (m, 1 H), 8.79–8.81 (m, 2 H).

Step C: Preparation of 2-[(4-vinyl-2-fluorophenyl)amino]-3,4-difluoro-N-(2-hydroxy-ethoxy)benzamide 3,4-difluoro-2-(2-fluoro-4-iodo-phenylamino)-N-(2-hydroxy-ethoxy)-benzamide (1.00 g, 2.21 mmol) was dissolved in dry dimethoxyethane (DME, 18 ml) under a nitrogen atmosphere, $Pd(Ph_3P)_4$ (0.13 g, 0.11 mmol) was added and the resulting yellow solution was stirred at ambient temperature for 20 min. $K_2CO_3$ (−325 mesh, 0.31 g, 2.21 mmol), water (5.3 ml) and boron complex 2 (0.54 g, 2.21 mmol) were added and the contents of the flask were refluxed for 1 h.[1] Water (50 ml) and brine (50 ml) were added and the aqueous phase was extracted with ethyl acetate (3×50 ml). The combined organic extracts were washed with brine (20 ml) and dried over $MgSO_4$. The solvent was removed under vacuum and the residual dark orange oil was chromatographed (ethyl acetate as eluent) to give 0.59 g (76% yield) of 2-[(4-vinyl-2-fluorophenyl)amino]-3,4-difluoro-N-(2-hydroxy-ethoxy)benzamide as a light yellow solid, mp 134–137° C. $^1$H NMR ($d_6$-DMSO) δ 3.53–3.54 (m, 2 H), 3.82 (s, 2 H), 4.69–4.72 (m, 1 H), 5.14 (d, 1H, J=11 Hz), 5.69–5.77 (m, 1 H), 6.57–6.64 (m, 1 H), 6.77–6.83 (m, 1 H), 7.09–7.18 (m, 2 H), 7.33–7.40 (m, 2 H), 8.74 (bs, 1 H), 11.86 (bs, 1 H).

A small sample was recrystallized from hexanes/ethyl acetate and submitted for elemental analysis. The results are as follows: C, 57.81 (57.96); H, 4.38 (4.29); N, 7.56 (7.95); F, 16.02 (16.28).

EXAMPLE 5

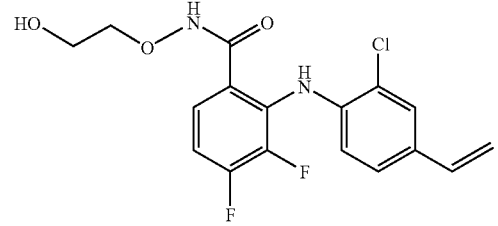

2-(2-Chloro-4-vinyl-phenylamino)-3,4-difluoro-N-(2-hydroxy-ethoxy)-benzamide

The title compound can be prepared by the procedure of Example 2, Steps A–D (0.69 g, 44% yield): $^1$H NMR (400 MHz, DMSO-$d_6$) δ 11.97 (br s, 1 H), 8.94 (br s, 1 H), 7.59 (d, J=1.7 Hz, 1 H), 7.47 (br t, J=6.4 Hz, 1 H), 7.31 (dd, J=8.3, 2.0 Hz, 1 H), 7.29–7.21 (m, 1 H), 6.77 (dd, J=8.3, 6.6 Hz, 1 H), 6.64 (dd, J=17.6, 11.0 Hz, 1 H), 5.75 (dd, J=17.6, 0.7 Hz, 1 H), 5.18 (dd, J=10.8, 0.7 Hz, 1 H), 4.73 (br s, 1 H), 3.88 (br s, 2 H), 3.58 (br s, 2 H); $^{19}$F NMR (376 MHz, DMSO-$d_6$) δ −132.5, −141.3 (d, J=20.2 Hz); MS (APCI+)= 368.9. Anal. Calcd/found for $C_{17}H_{15}ClF_2N_2O_3$: C, 55.37/55.46; H, 4.10/3.91; N, 7.60/7.37.

EXAMPLE 6

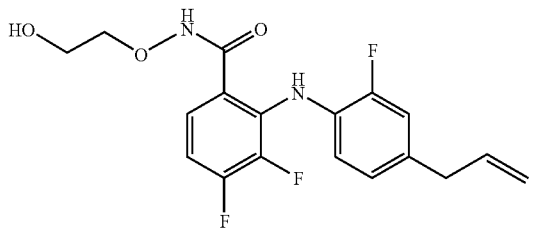

2-(4-Allyl-2-fluoroanilino)-3,4-difluoro-N-(2-hydroxyethoxy)benzamide

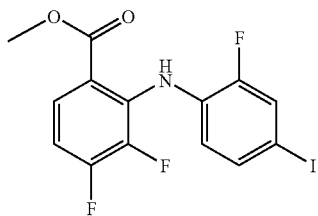

Step A: Preparation of methyl 3,4-difluoro-2-(2-fluoro-4-iodoanilino)-3,4-difluorobenzoate 2-(2-Fluoro-4-iodoanilino)-3,4-difluorobenzoic acid (which can be prepared according to the procedure in PCT publication No. WO 00/41505) (5.00 g, 12.7 mmol) was dissolved in a mixture of Et$_2$O (60 mL) and MeOH (30 mL), then TMS-diazomethane solution (8.27 ml of a 2 M solution in hexanes, 16.5 mmol) was added dropwise. This mixture was stirred at RT for 15 h., the excess reagent quenched with acetic acid, then all solvents removed under reduced pressure. The resulting residue was dissolved in EtOAc (200 mL), which was washed with saturated NaHCO$_3$ (2×200 mL), water (200 mL) and brine (100 mL). The EtOAc layer was then dried (Na$_2$SO$_4$) and the solvent removed under reduced pressure to afford methyl 3,4-difluoro-2-(2-fluoro-4-iodoanilino)-3,4-difluorobenzoate as a pink solid (5.16 g, 100%) which was used directly in the next step. $^1$H NMR [400 MHz, (CD$_3$)$_2$SO] δ 8.73 (s, 1 H), 7.76 (ddd, J=9.0, 6.0, 2.1 Hz, 1 H), 7.61 (dd, J=10.8, 1.9 Hz, 1 H), 7.41 (ddd, J=8.5, 1.9, 1.0 Hz, 1 H), 7.21–7.12 (m, 1 H), 6.80 (ddd, J=8.8, 8.8, 4.4 Hz, 1 H), 3.81 (s, 3H).

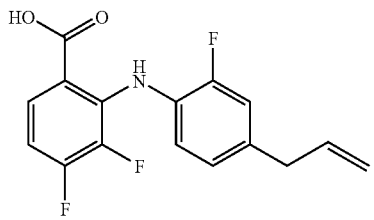

Step B: Preparation of 2-(4-Allyl-2-fluoroanilino)-3,4-difluorobenzoic acid

Methyl 3,4-difluoro-2-(2-fluoro-4-iodoanilino)benzoate (1.00 g), 2.45 mmol) and (Ph$_3$P)$_4$Pd (568 mg, 0.49 mmol) were weighed into a dry flask which was fitted with a condensor and flushed with nitrogen. Dioxane (20 mL) and allyltributyltin (976 mg, 2.95 mmol) were added via syringe and the entire mixture heated at reflux overnight. All solvent was removed under reduced pressure and the residue loaded directly onto a silica gel column (10% EtOAc/PE as eluant). After chromatography, the crude methyl ester was obtained as a pale yellow oil which was dissolved in a mixture of EtOH (25 mL) and 1 M NaOH (25 mL) and stirred overnight at RT. The mixture was then diluted with water (70 mL) and acidified with 1 M HCl (approx. 30 mL), then extracted with EtOAc (3×100 mL). The combined EtOAc fractions were washed with water (100 mL), brine (100 mL), dried (Na$_2$SO$_4$), then the solvent removed under reduced pressure to afford a pale yellow solid which was purified by chromatography on silica gel (50% EtOAc/PE as eluant) to afford 2-(4-allyl-2-fluoroanilino)-3,4-difluorobenzoic acid as pale yellow needles (583 mg, 72%); m.p. (EtOAc/hexane) 199–201° C. $^1$H NMR [400 MHz, (CD$_3$)$_2$SO] δ 13.68 (v br s, 1 H), 9.25 (br s, 1 H), 7.81 (ddd, J=8.3, 6.1, 2.0 Hz, 1 H), 7.07 (dd, J=12.2, 1.7 Hz, 1 H), 7.06–6.98 (m, 2 H), 6.93 (dd, J=8.2, 1.6 Hz, 1 H), 6.01–5.89 (m, 1 H), 5.13–5.03 (m, 2 H), 3.51–3.40 (m, 2H, obscured by H$_2$O). Anal. calcd. for C$_{16}$H$_{12}$F$_3$NO$_2$: C, 62.5; H, 3.9; N, 4.6. Found C, 62.7; H, 4.1; N, 4.5.

Step C: Preparation of 2-(4-allyl-2-fluoroanilino)-3,4-difluoro-N-(2-hydroxyethoxy)benzamide 2-(4-Allyl-2-fluoroanilino)-3,4-difluorobenzoic acid (700 mg, 2.28 mmol) was dissolved in MeOH (20 mL) to which was added 2-(aminooxy)ethanol (263 mg, 3.42 mmol), followed by 4-(4,6-dimethoxy-1,3,5-triazin-2-yl)-4-methylmorpholinium chloride [DMT-MM, prepared according to the procedure of Kunishima et al [*Tetrahedron*, 55, 13159–13170 (1999)]] (946 mg, 3.42 mmol). This mixture was stirred 15 h. at room temperature. The MeOH was removed under reduced pressure and the resulting oil dissolved in EtOAc (100 mL), which was washed with water (2×100 mL), brine (100 mL) and dried (Na$_2$SO$_4$). The solvent was removed under reduced pressure to afford a crude yellow oil which was purified by filtration through a plug of silica gel (50% EtOAc/PE as eluant) to give 2-(4-allyl-2-fluoroanilino)-3,4-difluoro-N-(2-hydroxyethoxy) benzamide as a white solid (734 mg, 88%); m.p. (EtOAc/hexane) 173–177° C. $^1$H NMR [400 MHz, (CD$_3$)$_2$SO] δ 11.85 (br s, 1 H), 8.75 (br s, 1 H), 7.43–7.37 (m, 1 H), 7.14–7.07 (m, 1 H), 7.05–6.99 (m, 1 H), 6.90–6.81 (m, 2 H), 5.99–5.87 (m, 1 H), 5.02–5.11 (m, 2 H), 4.70 (br s, 1 H), 3.85 (t, J=4.9 Hz, 1H), 3.57 (t, J=4.9 Hz, 2H), 3.51–3.40 (m, 2H, obscured by H$_2$O). Anal. calcd. for C$_{18}$H$_{17}$F$_3$N$_2$O$_3$: C, 59.0; H, 4.7; N, 7.7. Found C, 59.1; H, 4.5; N, 7.4.

EXAMPLE 7

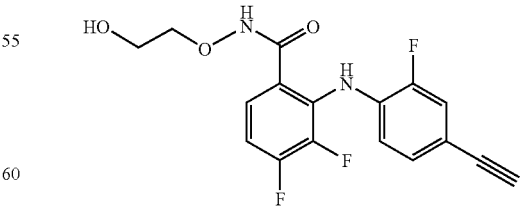

2-[(4-Ethynyl-2-fluorophenyl)amino]-3,4-difluoro-N-2-hydroxyethoxy)benzamide

The product of Example 1, Step C, 3,4-difluoro-2-[(4-ethynyl-2-fluorophenyl)amino]benzoic acid (349 mg, 1.20 mmol) was dissolved in dry THF (15 mL), to which was added carbonyldiimidazole (CDI) (389 mg, 2.40 mmol). Within 10 minutes, a bright yellow solution was obtained and conversion to the imidazolide was confirmed by TLC (50% EtOAc/hexanes). A solution of 2-(aminooxy)ethanol (370 mg, 4.80 mmol) in THF (5 mL) was then added and the mixture stirred for 15 hours at room temperature. The reaction solvent was removed under reduced pressure and the residue partitioned between 1 M HCl (100 mL) and EtOAc (100 nL). The EtOAc layer was then washed with water (100 mL) and saturated NaCl solution (100 mL), dried (Na$_2$SO$_4$), and the solvent removed under reduced pressure to afford an oil which was purified by flash column chromatography on silica gel (50% EtOAc/hexanes) to give 2-[(4-ethynyl-2-fluorophenyl)amino]-3,4-difluoro-N-(2-hydroxyethoxy)benzamide as a pale yellow solid (232 mg, 55%); m.p. (EtOAc/hexanes) 158–161° C. $^1$H NMR [400 MHz, (CD$_3$)$_2$SO] δ 11.80 (br s, 1 H), 8.84 (br s, 1 H), 7.43 (ddd, J=8.8, 5.9, 1.9 Hz, 1 H), 7.34 (dd, J=12.2, 1.9 Hz, 1 H), 7.25 (ddd, J=9.9, 9.0, 7.3 Hz, 1 H), 7.16 (ddd, J=8.3, 1.9, 0.9 Hz, 1 H), 6.79 (ddd, J=9.1, 8.3, 4.9 Hz, 1 H), 4.71 (br s, 1 H), 4.10 (s, 1 H), 3.84 (t, J=5.0 Hz, 2 H), 3.56 (t, J=5.0 Hz, 2 H). Anal. Calcd for C$_{17}$H$_{13}$F$_3$N$_2$O$_3$: C, 58.5; H, 4.1; N, 8.0. Found: C, 58.3; H, 3.7; N, 8.0.

EXAMPLE 7A

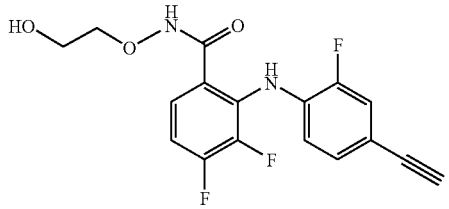

2-[(4-ethynyl-2-fluorophenyl)amino]-3,4-difluoro-N-(2-hydroxy-ethoxy)benzamide

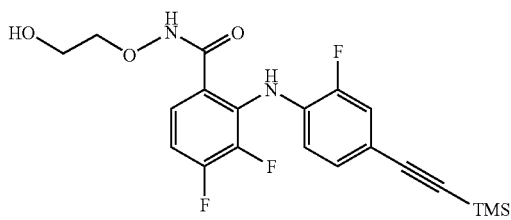

Step A: Preparation of 2-[(4-(2-trimethylsilyl)ethynyl-2-fluorophenyl)amino]-3,4-difluoro-N-(2-hydroxyethoxy)benzamide A 1 L round-bottomed flask was charged with compound 3,4-difluoro-2-(2-fluoro-4-iodo-phenylamino)-N-(2-hydroxy-ethoxy)-benzamide (45.2 g, 0.1 M) and PdCl$_2$(PPh$_3$)$_2$ (1.4 g, 2.0 mmol, 0.02 eq) and flushed with argon gas. Trimethylsilyl-acetylene (15.5 mL, 0.11 mole, 1.1 eq.) was added, followed by the addition of Et$_3$N (250 mL). The mixture was stirred under argon at ambient temperature for 15 minutes. Solid CuI (0.38 g, 2.0 mmol, 0.02 eq.) was added. The orange mixture was stirred at RT overnight (18 hrs). The reaction mixture turned dark brown. The high performance liquid chromatography (HPLC) test of an aliquot showed 99% of product and no starting material. The mixture was concentrated under reduced pressure. Water (100 mL) was added and the mixture was acidified to pH ~1 with 1N HCl. The mixture was extracted with EtOAc (3×100 mL). The combined organic extracts were washed with brine, saturated NaHCO$_3$, and dried (MgSO$_4$). The solvent was evaporated under vacuo to give a brown solid, which was stirred in heptane-dichloromethane (1:1, 200 mL) for 15 min. The solid (most of the brown impurities were washed out with this trituration.) was filtered, and recrystallized from heptane-EtOAc (Decolorizing charcoal was used to remove yellow color. If charcoal was not used, the product was off-white.) to give white solid. The solid was dried at 50° C. vacuum oven for 20 hrs to yield 2-[(4-(2-trimethylsilyl)ethynyl-2-fluorophenyl)amino]-3,4-difluoro-N-(2-hydroxyethoxy)benzamide as a white solid, 33.9 g, 80.4%, mp 178–178.5° C., Anal.: C, 56.86 (56.86); H, 5.11 (5.01); N, 6.61 (6.63); F, 13.62 (13.49).

Step B: Preparation of 2-[(4-ethynyl-2-fluorophenyl)amino]-3,4-difluoro-N-(2-hydroxy-ethoxy)benzamide A 0.5 L round-bottomed flask was charged with compound 2-[(4-(2-trimethylsilyl)ethynyl-2-fluorophenyl)amino]-3,4-difluoro-N-(2-hydroxyethoxy)benzamide (10.2 g, 24.14 mmol) and anhydrous MeOH (200 mL). Powder K$_2$CO$_3$ (6.7 g, 48.29 mmol, 2.0 eq.) was added. The white suspension was stirred at ambient temperature for 5 hrs. Two thirds of MeOH was evaporated under reduced pressure. Water (300 mL) was added to the mixture. The mixture was acidified to pH ~1 with slow addition of 1N HCl. White solid formed. The mixture was stirred for 15 min. The solid was filtered washed with water, and dried at 50° C. vacuum oven for 18 hrs. The solid was recrystallized from heptane-EtOAc (Decolorizing carbon was used. Without charcoal, the product obtained was light yellow.) to give white solid. The solid was dried at 50° C. vacuum oven for 20 hrs to yield 2-[(4-ethynyl-2-fluorophenyl)amino]-3,4-difluoro-N-(2-hydroxy-ethoxy)benzamide as a white solid, 7.9 g, 93.8%, mp 161.5–162.5° C., Anal.: C, 58.19 (58.29); H, 3.59 (3.74); N, 7.81 (8.00); F, 16.34 (16.27).

EXAMPLE 7B

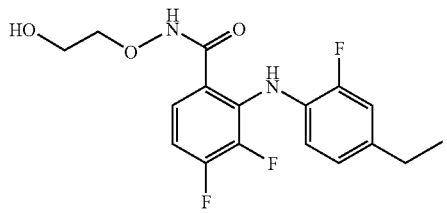

2-[(4-ethyl-2-fluorophenyl)amino]-3,4-difluoro-N-(2-hydroxyethoxy)-benzamide

A mixture of the product of Example 7A, 2-[(4-ethynyl-2-fluorophenyl)amino]-3,4-difluoro-N-(2-hydroxy-ethoxy) benzamide (11.0 g, 31.40 mmol), Pd—C (10%, 1.0 g) in THF (100 mL) and MeOH (100 mL) was subject to hydrogenation (25 psi) for 14.8 hrs (The reaction was followed by HPLC until all SM peak disappeared.). The mixture was filtered through Celite® and the filtrates were concentrated to give a light yellow solid. The solid was recrystallized from heptane-EtOAc to give the title compound as a white solid, 6.97 g, 62.8%, mp 112–112.5° C. Anal.: C, 58.00 (57.63); H, 4.99 (4.84); N, 7.59 (7.91); F, 15.55 (16.09).

EXAMPLE 8

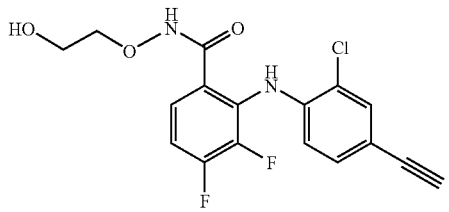

2-(2-Chloro-4-ethynyl-phenylamino)-3,4-difluoro-N-(2-hydroxy-ethoxy)-benzamide

Step A: Preparation of 2-(2-chloro-4-trimethylsilanylethynyl-phenylamino)-3,4difluoro-N-(2-hydroxy-ethoxy)-benzamide

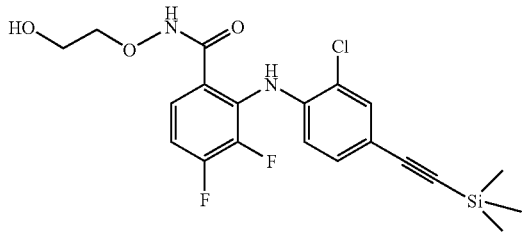

The product of Example 2, Step C, 2-(2-chloro-4-iodo-phenylamino)-3,4-difluoro-N-(2-hydroxy-ethoxy)-benzamide (3.25 g, 6.93 mmol) and (trimethylsilyl)acetylene (1.10 mL, 7.78 mmol) were combined in triethylamine (17 mL). Dichlorobis(triphenylphosphine)-palladium(II) (0.120 g, 0.017 mol) and cuprous iodide (0.033 g, 0.17 mmol) were added and the resultant solution was stirred at ambient temperature for 22 hours. The reaction mixture was adsorbed onto Celite® for 20 min and was filtered, washing with ethyl acetate. The filtrate was concentrated to a thick oil, further diluted with ethyl acetate (100 mL) and washed with aqueous citric acid (2 M, 2×25 mL), water, and brine. The organic layer was then dried over magnesium sulfate and concentrated in vacuo to afford a tan-colored solid. Recrystallization from heptane-ethyl acetate afforded 2-(2-chloro-4-trimethylsilanylethynyl-phenylamino)-3,4-difluoro-N-(2-hydroxy-ethoxy)-benzamide (2.34 g, 76% yield) as a grey-colored solid: $^1$H NMR (400 MHz, DMSO-$d_6$) δ 11.96 (s, 1 H), 8.95 (s, 1 H), 7.53 (d, J=1.7 Hz, 1 H), 7.47 (m, 1 H), 7.32 (m, 1 H), 7.27 -(dd, J=8.4, 1.8 Hz, 1 H), 6.72 (dd, J=8.0, 6.6 Hz, 1 H), 4.73 (t, J=5.5 Hz, 1 H), 3.87 (apparent t, J=4.7 Hz, 2 H), 3.57 (m, 2 H), 0.21 (s, 9 H); MS (APCI+)=439.1; MS (APCI−)=437.1.

Step B: Preparation of 2-(2-chloro-4-ethynyl-phenylamino)-3,4-difluoro-N-(2-hydroxy-ethoxy)-benzamide To a solution of the product of Example 8, Step A, 2-(2-Chloro-4-trimethylsilanylethynyl-phenylamino)-3,4-difluoro-N-(2-hydroxy-ethoxy)-benzamide (0.704 g, 1.60 mmol) in methanol (21 mL) was added acetic acid (0.1 mL) and cesium fluoride (0.600 g, 3.95 mmol). The resultant solution was stirred at ambient temperature. After 26 hours, the reaction mixture was partitioned between ethyl acetate (100 mL) and water (25 mL) and the organic layer was further washed with water (25 mL) and saturated brine (25 mL). The combined aqueous was extracted with ethyl acetate (50 mL). The combined organics were dried over magnesium sulfate and concentrated to a dark brown oil. Ether (15 mL) was added and crystallization ensued. The cream-colored solid was collected and dried under vacuum at 70° C. to afford 2-(2-chloro-4-ethynyl-phenylamino)-3,4-difluoro-N-(2-hydroxy-ethoxy)-benzamide (0.290 g): m.p. 155–157° C.; $^1$H NMR (400 MHz, DMSO-$d_6$) δ 11.94 (br s, 1 H), 8.95 (br s, 1 H), 7.55 (d, J=2.0 Hz, 1 H), 7.48 (m, 1H), 7.34–7.27 (m, 2 H), 6.74 (dd, J=8.4, 6.5 Hz, 1 H), 4.71 (br s, 1 H), 4.13 (s, 1 H), 3.88 (t, J=4.6 Hz, 2 H), 3.58 (t, J=4.7 Hz, 2 H); MS (APCI+)=367.0; MS (APCI−)=365.0; Anal. Calcd/found for $C_{17}H_{13}ClF_2N_2O_3$: C, 55.67/55.54; H, 3.57/3.23; N, 7.64/7.31. Concentration of the mother liquor afforded an additional crop of product (0.209 g, 85% total yield).

EXAMPLE 9

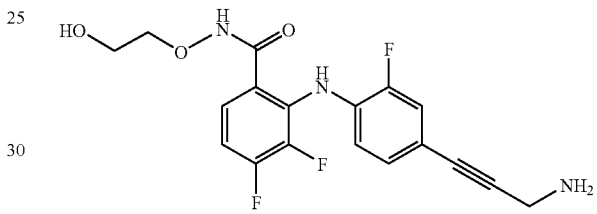

2-[4-(3-Amino-1-propynyl)-2-fluoroanilino]-3,4-difluoro-N-(2-hydroxyethoxy)benzamide The title compound was prepared by Sonogashira reaction of propargyl amine and 3,4-difluoro-2-(2-fluoro-4-iodo-phenylamino)-N-(2-hydroxy-ethoxy)-benzamide by the general procedure of Example 1, Step A. The orange oil resulting from workup was purified by chromatography on silica gel (10% MeOH/CH$_2$Cl$_2$ as eluant), to give 2-[4-(3-amino-1-propynyl)-2-fluoroanilino]-3,4-difluoro-N-(2-hydroxyethoxy)benzamide as a pale orange solid (100%); m.p. (Et$_2$O) 72–76° C. $^1$H NMR [400 MHz, (CD$_3$)$_2$SO] δ 9.14 (v br s, 1 H), 7.49–7.44 (m, 1 H), 7.21 (dd, J=12.3, 1.7 Hz, 1 H), 7.24–7.14 (m, 1 H), 7.08 (dd, J=8.4, 1.6 Hz, 1 H), 6.77 (ddd, J=8.8, 8.8, 5.1 Hz, 1 H), 5.45 (br s, 2 H), 3.83 (t, J=4.8 Hz, 2 H), 3.55 (t, J=5.0 Hz, 2H), 3.41–3.32 (m, 2H, obscured by H$_2$O). Not all exchangeable protons observed. CRL10671. Await HRMS. Anal. calcd. for $C_{28}H_{16}F_3N_3O_3$: C, 57.0; H, 4.3; N, 11.1. Await Found. HRMS (EI+) calcd for $C_{18}H_{16}F_3N_3O_3$ 379.1144 (M+), found 379.1140.

EXAMPLE 10

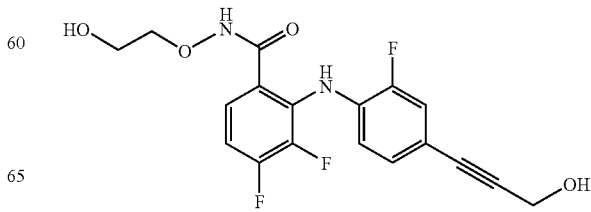

3,4-Difluoro-2-[2-fluoro-4-(3-hydroxy-1-propynyl)anilino]-N-(2-hydroxyethoxy)benzamide

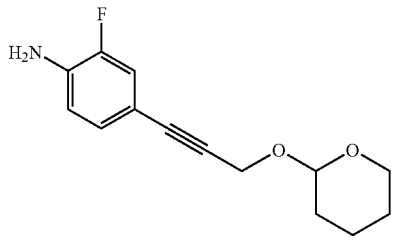

Step A: Preparation of 2-fluoro-4-[3-(tetrahydro-2H-pyran-2-yloxy)-1-propnyl]aniline 2-Propynyl tetrahydro-2H-pyran-2-yl ether was prepared according the method of Li et al [*J. Am Chem. Soc.*, 121(39), 9034–9042 (1999)]. 2-Fluoro-4-[3-(tetrahydro-2H-pyran-2-yloxy)-1-propynyl]aniline was then prepared by Sonogashira reaction of 2-propynyl tetrahydro-2H-pyran-2-yl ether and 2-fluoro-4-iodoaniline by the general procedure of Example 1, Step A. The desired product was isolated as an amber oil (91%). $^1$H NMR [400 MHz, (CD$_3$)$_2$SO] δ 7.07 (dd, J=12.1, 1.8 Hz, 1 H), 6.98 (dd, J=8.2, 1.7 Hz, 1 H), 6.70 (dd, J=9.3, 8.3 Hz, 1 H), 5.56 (br s, 2 H), 4.78 (br s, 1 H), 4.42 (d, J=15.9 Hz, 1 H), 4.33 (d, J=15.9 Hz, 1 H), 3.78–3.70 (m, 2 H), 3.50–3.43 (m, 2 H), 1.77–1.59 (m, 2 H), 1.56–1.41 (m, 4 H). HRMS (EI$^+$) calcd. for C$_{14}$H$_{16}$FNO$_2$ 249.1165 (M$^+$), found 249.1164.

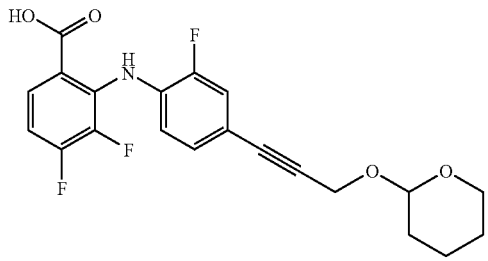

Step B: Preparation of 3,4-difluoro-2-{2-fluoro-4-[3-(tetrahydro-2H-pyran-2-yloxy)-1-propynyl]anilino}benzoic acid 2,3,4-Trifluorobenzoic acid and 2-fluoro-4-[3-(tetrahydro-2H-pyran-2-yloxy)-1-propynyl]aniline were reacted in the presence of LiHMDS solution in THF by the general procedure of Example 1, Step B. After workup, followed by purification by chromatography on silica gel (50% EtOAc/PE as eluant), 3,4-difluoro-2-{2-fluoro-4-[3-(tetrahydro-2H-pyran-2-yloxy)-1-propynyl]anilino}benzoic acid was isolated as a cream-yellow solid (68%); m.p. (Et$_2$O/hexane) 164–166° C. $^1$H NMR [400 MHz, (CD$_3$)$_2$SO] δ 13.60 (v br s, 1 H), 9.27 (br s, 1 H), 7.83 (ddd, J=8.2, 6.1, 1.9 Hz, 1 H), 7.36 (dd, J=12.0, 1.7 Hz, 1 H), 7.21–7.11 (m, 2 H), 6.96 (td, J=8.8, 5.5 Hz, 1 H), 4.80 (br s, 1 H), 4.47 (d, J=16.0 Hz, 1 H), 4.38 (d, J=16.0 Hz, 1 H), 3.79–3.71 (m, 2H), 3.51–3.45 (m, 2 H), 1.77–1.61 (m, 2 H), 1.56–1.44 (m, 4 H). Anal. calcd. for C$_{21}$H$_{18}$F$_3$NO$_4$: C, 62.2; H, 4.5; N, 3.5. Found C, 62.5; H, 4.4; N, 3.6.

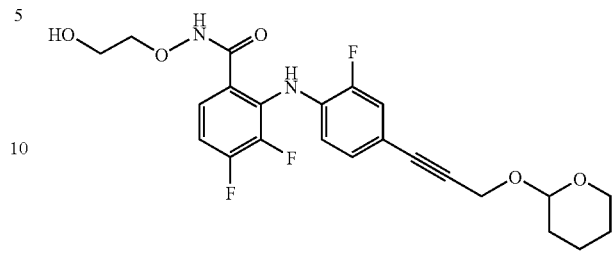

Step C: Preparation of 3,4-difluoro-2-{2-fluoro-4-[3-(tetrahydro-2H-pyran-2-yloxy)-1-propynyl]anilino}-N-(2-hydroxyethoxy)benzamide The title compound was prepared from reaction of 3,4-difluoro-2-{2-fluoro-4-[3-(tetrahydro-2H-pyran-2-yloxy)-1-propynyl]anilino}benzoic acid with CDI and 2-(aminooxy)ethanol by the general procedure of Example 1, Step E, then purified by column chromatography on silica gel (50% EtOAc/PE) as eluant), to give 3,4-difluoro-2-{2-fluoro-4-[3-(tetrahydro-2H-pyran-2-yloxy)-1-propynyl]anilino}-N-(2-hydroxyethoxy)benzamide as a white solid (69%) which was used directly in the next step. $^1$H NMR [400 MHz, (CD$_3$)$_2$SO] δ 11.80 (br s, 1 H), 8.87 (br s, 1 H), 7.46–7.39 (m, 1 H), 7.31 (dd, J=12.2, 1.8 Hz, 1 H), 7.28–7.20 (m, 1 H), 7.14 (dd, J=8.3, 1.6 Hz, 1 H), 6.79 (ddd, J=8.8, 8.8, 4.7 Hz, 1H), 4.80 (br s, 1H), 4.46 (d, J=16.1 Hz, 1H), 4.36 (d, J=16.0 Hz, 1 H), 3.84 (t, J=4.8 Hz, 2 H), 3.75 (ddd, J=11.5, 8.6, 3.3 Hz, 2 H), 3.55 (t, J=4.8 Hz, 2 H), 3.51–3.44 (m, 2 H), 1.76–1.60 (m, 2 H), 1.55–1.42 (m, 4 H). HRMS (EI$^+$) calcd. for C$_{23}$H$_{23}$F$_3$N$_2$O$_5$ 464.1559 (M$^+$), found 464.1558.

Step D: Preparation of 3,4-difluoro-2-[2-fluoro-4-(3-hydroxy-1-propynyl)anilino]-N-(2-hydroxyethoxy)benzamide 3,4-Difluoro-2-{2-fluoro-4-[3-(tetrahydro-2H-pyran-2-yloxy)-1-propynyl]anilino}-N-(2-hydroxyethoxy)benzamide (115 mg, 0.25 mmol) was dissolved in EtOH (4 mL) to which was added 1 M HCl (5 drops). This reaction mixture was stirred overnight at RT, then the mixture was diluted with water (50 mL) and extracted with EtOAc (4×30 mL). The combined EtOAc fractions were washed with water (2×20 mL), brine (50 mL) and dried (Na$_2$SO$_4$) then the solvent removed under reduced pressure to afford a white solid which was purified by filtration through a plug of silica gel (EtOAc as eluant) to afford 3,4-difluoro-2-[2-fluoro-4-(3-hydroxy-1-propynyl)anilino]-N-(2-hydroxyethoxy)benzamide as a cream solid (94 mg, 100%); m.p. (Et$_2$O/hexane) 169–172° C. $^1$H NMR [400 MHz, (CD$_3$)$_2$SO] δ 11.84 (br s, 1 H), 8.91 (br s, 1 H), 7.46–7.40 (m, 1 H), 7.29–7.19 (m, 2 H), 7.10 (dd, J=8.3, 1.6 Hz, 1 H), 6.78 (ddd, J=8.9, 8.9, 4.8 Hz, 1 H), 5.29 (t, J=5.9 Hz, 1 H), 4.76 (br s, 1 H), 4.27 (d, J=5.9 Hz, 2 H), 3.84 (t, J=4.8 Hz, 2 H), 3.56 (t, J=4.8 Hz, 2 H). Anal. calcd. for C$_{18}$H$_{15}$F$_3$N$_2$O$_4$: C, 56.9; H, 4.0; N, 7.4. Found C, 56.8; H, 4.0; N, 7.4.

EXAMPLE 11

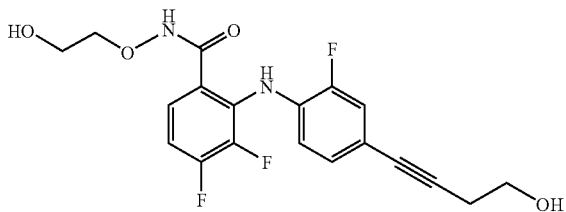

3,4-Difluoro-2-[2-fluoro-4-(4-hydroxy-1-butynyl)anilino]-N-(2-hydroxyethoxy)benzamide

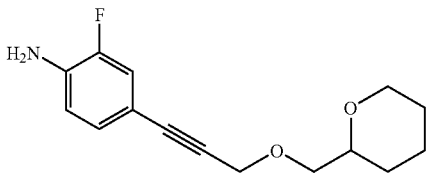

Step A: Preparation of 2-fluoro-4-[4-(tetrahydro-2H-pyran-2-yloxy)-1-butynyl]aniline 3-Butynyl tetrahydro-2H-pyran-2-yl ether was prepared according to the method of Li et al [*J. Am Chem. Soc.*, 121(39), 9034–9042 (1999)]. 2-Fluoro-4-[4-(tetrahydro-2H-pyran-2-yloxy)-1-butynyl]aniline was then prepared by Sonogashira reaction of 3-butynyl tetrahydro-2H-pyran-2-yl ether and 2-fluoro-4-iodoaniline by the general procedure of Example 1, Step A. The desired product was isolated as an orange oil (100%). $^1$H NMR [400 MHz, (CD$_3$)$_2$SO] δ 6.96 (dd, J=12.2, 1.7 Hz, 1 H), 6.90 (dd, J=8.2, 1.8 Hz, 1 H), 6.67 (dd, J=9.4, 8.4 Hz, 1 H), 5.43–5.41 (m, 2 H), 4.66–4.63 (m, 1 H), 3.82–3.67 (m, 2 H), 3.56–3.40 (m, 2 H), 2.62 (t, J=6.9 Hz, 2 H), 1.78–1.56 (m, 2 H), 1.54–1.39 (m, 4 H). HRMS (EI$^+$) calcd. for C$_{15}$H$_{18}$FNO$_2$ 263.1322 (M$^+$), found 263.1323.

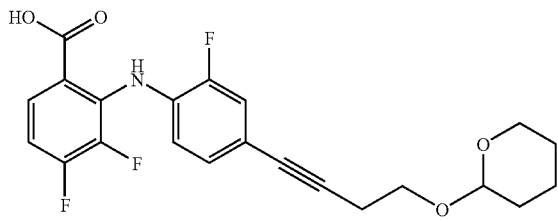

Step B: Preparation of 3,4-difluoro-2-{2-fluoro-4-[4-(tetrahydro-2H-pyran-2-yloxy)-1-butynyl]anilino}benzoic acid 2,3,4-Trifluorobenzoic acid and 2-fluoro-4-[4-(tetrahydro-2H-pyran-2-yloxy)-1-butynyl]aniline were reacted in the presence of LiHMDS solution by the general procedure of Example 1, Step B. After workup, followed by purification by column chromatography on silica gel (50% EtOAc as eluant), unreacted aniline (26%), followed by 3,4-difluoro-2-{2-fluoro-4-[4-(tetrahydro-2H-pyran-2-yloxy)-1-butynyl]anilino}benzoic acid (31%) were isolated; m.p. (Et$_2$O/hexane) 175–178° C. $^1$H NMR [400 MHz, (CD$_3$)$_2$SO] δ 13.55 (v br s, 1 H), 9.28 (br s, 1 H), 7.82 (ddd, J=8.2, 6.0, 1.8 Hz, 1 H), 7.25 (dd, J=12.0, 1.7 Hz, 1 H), 7.16–7.08 (m, 2 H), 6.95 (ddd, J=8.8, 8.8, 5.4 Hz, 1 H), 4.66 (t, J=3.4 Hz, 1 H), 3.83–3.70 (m, 2 H), 3.59–3.41 (m, 2H), 2.68 (t, J=6.8 Hz, 1 H), 1.78–1.58 (m, 2 H), 1.53–1.40 (m, 4 H). Anal. calcd. for C$_{22}$H$_{20}$F$_3$NO$_4$: C, 63.0; H, 4.8; N, 3.3. Found C, 63.0; H, 4.8; N, 3.5.

Step C: Preparation of 3,4-difluoro-2-[2-fluoro-4-(4-hydroxy-1-butynyl)anilino]-N-(2-hydroxyethoxy)benzamide The title compound was prepared by reaction of 3,4-difluoro-2-{2-fluoro-4-[4-(tetrahydro-2H-pyran-2-yloxy)-1-butynyl]anilino}benzoic acid with CDI and 2-(aminooxy)ethanol by the general procedure of Example 1, Step E, then purified by column chromatography on silica gel (50% EtOAc/PE as eluant) to give 3,4-difluoro-2-{2-fluoro-4-[4-(tetrahydro-2H-pyran-2-yloxy)-1-butynyl]anilino}-N-(2-hydroxyethoxy)benzamide as a viscous transparent oil which was immediately dissolved in EtOH and treated with 1 M HCl according to the general procedure of Example 10, Step D. Purification of the resulting oil was carried out by filtration through a plug of silica gel (EtOAc as eluant) to give 3,4-difluoro-2-[2-fluoro-4-(4-hydroxy-1-butynyl)anilino]-N-(2-hydroxyethoxy)benzamide as a pale yellow crystalline solid (51%); m.p. (EtOAc/Et$_2$O) 126–129° C. $^1$H NMR [400 MHz, (CD$_3$)$_2$SO] δ 11.82 (br s, 1 H), 8.85 (br s, 1 H), 7.45–7.39 (m, 1 H), 7.25–7.17 (m, 2H), 7.07 (dd, J=8.3, 1.4 Hz, 1 H), 6.78 (dd, J=8.8, 8.8, 4.7 Hz, 1 H), 4.88 (t, J=5.6 Hz, 1 H), 4.73 (br s, 1 H), 3.85 (t, J=4.8 Hz, 2 H), 3.59–3.53 (m, 4 H), 2.53 (t, J=6.9 Hz, 1 H). Anal. calcd. for C$_{19}$H$_{17}$F$_3$N$_2$O$_4$.0.25Et$_2$O: C, 58.2; H, 4.8; N, 6.8. Found C, 58.1; H, 4.8; N, 7.1.

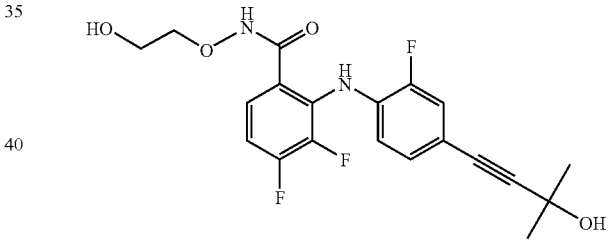

EXAMPLE 12

3,4-Difluoro-2-[2-fluoro-4-(3-hydroxy-3-methyl-1-butynyl)anilino]-N-(2-hydroxyethoxy)benzamide 3,4-difluoro-2-(2-fluoro-4-iodoanilino)-N-(2-hydroxyethoxy)benzamide, which can be prepared according to the procedure in PCT Publication No. WO 00/41505, and 2-methyl-3-butyn-2-ol were reacted in the presence of CuI and (PhP$_3$)$_2$Cl$_2$ by the general procedure of Example 1, Step A, and the mixture stirred at RT for 4 h. The reaction mixture was diluted with 50% Et$_2$O/MeOH and filtered through Celite®. The filtrate was concentrated under reduced pressure and further purified by flash chromatography on silica (CH$_2$Cl$_{2-10}$% MeOH/CH$_2$Cl$_2$ gradient elution) to give 3,4-difluoro-2-[2-fluoro-4-(3-hydroxy-3-methyl-1-butynyl)anilino]-N-(2-hydroxyethoxy)benzamide (97%) as a cream solid; m.p. (CH$_2$Cl$_2$/Hexane) 139–142° C. $^1$H NMR [400 MHz, (CD$_3$)$_2$SO] δ 11.80 (br s, 1 H), 8.78 (br s, 1 H), 7.46–7.40 (m, 1 H), 7.28–7.19 (m, 2 H), 7.07 (dd, J=8.4, 1.5 Hz, 1 H), 6.79 (ddd, J=8.7, 8.7, 4.7 Hz, 1 H), 5.43 (br s, 1 H), 4.70 (br s, 1 H), 3.86 (t, J=4.7 Hz, 2 H), 3.57 (t, J=4.7

Hz, 2 H), 1.45 (s, 6 H). Anal. Calcd for $C_{20}H_{19}F_3N_2O_4$: C, 58.8; H, 4.7; N, 6.9. Found C, 58.5; H, 4.8; N, 6.7.

EXAMPLE 13

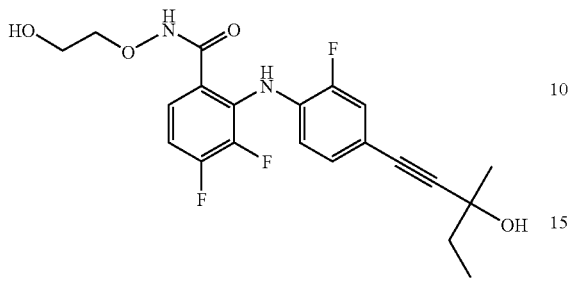

3,4-Difluoro-2-[2-fluoro-4-(3-hydroxy-3-methyl-1-pentynyl)anilino]-N-(2-hydroxyethoxy)benzamide 3,4-difluoro-2-(2-fluoro-4-iodoanilino)-N-(2-hydroxyethoxy)benzamide which can be prepared according to the procedure in PCT Publication No. WO 00/41505, and 3-methyl-1-pentyn-3-ol were reacted in the presence of CuI and $(PhP_3)_2PdCl_2$ by the general procedure of Example 1, Step A, and the mixture stirred at RT for 4 h. The reaction mixture was diluted with 50% $Et_2O$/MeOH and filtered through Celite®. The filtrate was concentrated under reduced pressure and further purified by flash chromatography on silica ($CH_2Cl_2$-10% MeOH/$CH_2Cl_2$ gradient elution) to give 3,4-difluoro-2-[2-fluoro-4-(3-hydroxy-3-methyl-1-pentynyl)anilino]-N-(2-hydroxyethoxy)benzamide (77%) as a white solid; m.p. ($CH_2Cl_2$/Hexane) 127–131° C.

$^1$H NMR [400 MHz, $(CD_3)_2SO$] δ 11.79 (br s, 1 H), 8.79 (br s, 1 H), 7.45–7.39 (m, 1H), 7.28–7.18 (m, 2 H), 7.07 (dd, J=8.4, 1.5 Hz, 1 H), 6.79 (ddd, J=8.7, 8.7, 4.6 Hz, 1 H), 5.31 (br s, 1 H), 4.71 (br s, 1 H), 3.86 (t, J=4.7 Hz, 2 H), 3.57 (t, J=4.7 Hz, 2H), 1.68–1.57 (m, 2 H), 1.40 (s, 3 H), 0.98 (t, J=7.4 Hz, 3 H). Anal. Calcd for $C_{21}H_{21}F_3N_2O_4$: C, 59.7; H, 5.0; N, 6.6. Found C, 59.9; H, 5.1; N, 6.9.

EXAMPLE 14

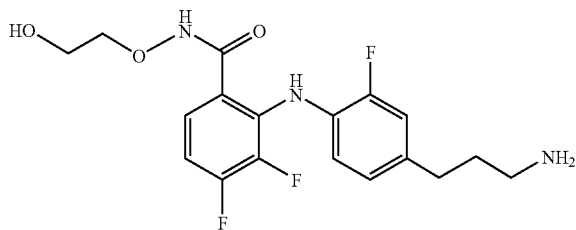

2-[4-(3-Aminopropyl)-2-fluoroanilino]-3,4-difluoro-N-(2-hydroxyethoxy)benzamide

The product of Example 9, 2-[4-(3-amino-1-propynyl)-2-fluoroanilino]-3,4-difluoro-N-(2-hydroxyethoxy)benzamide was dissolved in absolute EtOH and hydrogenated in the presence of 5% Pd/C by the general procedure of Example 1, Step D. Purification of the resulting oil was carried out by column chromatography on silica gel (1% $NH_4OH$ in 25% MeOH/$CH_2Cl_2$ as eluant) to give 2-[4-(3-aminopropyl)-2-fluoroanilino]-3,4-difluoro-N-(2-hydroxyethoxy)benzamide as a cream solid (46%); m.p. (MeOH/$CH_2Cl_2$) 178–181° C. $^1$H NMR [400 MHz, $(CD_3)_2SO$] δ 7.61–7.53 (m, 1 H), 6.97–6.87 (m, 2 H), 6.78 (dd, J=8.2, 1.3 Hz, 1 H), 6.60 (dd, J=15.1, 8.6 Hz, 1 H), 4.10 (br s, 1 H), 3.77 (t, J=5.0 Hz, 2 H), 3.56 (t, J=5.0 Hz, 2 H), 2.70 (t, J=7.3 Hz, 2 H), 2.53 (t, J=8.0 Hz, 2 H), 1.75 (pentet, J=7.5 Hz, 2 H). Not all exchangeable protons observed. Anal. calcd. for $C_{18}H_{20}F_3N_3O_3$: C, 56.4; H, 5.3; N, 11.0. Await Found.

EXAMPLE 15

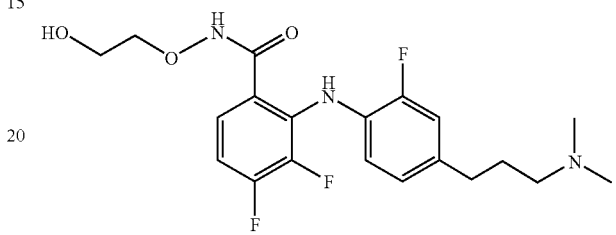

2-{4-[3-(Dimethylamino)propyl]-2-fluoroanilino}-3,4-difluoro-N-(2-hydroxyethoxy)benzamide

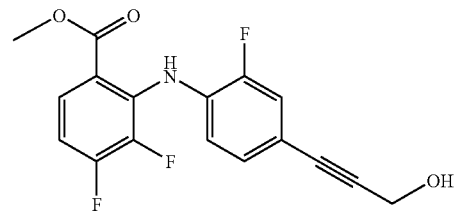

Step A: Preparation of methyl 3,4-difluoro-2-[2-fluoro-4-(3-hydroxy-1-propynyl)anilino]benzoate The title compound was prepared by Sonogashira reaction of propargyl alcohol and methyl 3,4-difluoro-2-(2-fluoro-4-iodoanilino)benzoate by the general procedure of Example 1, Step A. The oil resulting from workup was purified by chromatography on silica gel (20% EtOAc/PE as eluant), to give methyl 3,4-difluoro-2-[2-fluoro-4-(3-hydroxy-1-propynyl)anilino]benzoate as a pale yellow solid (94%); m.p. ($Et_2O$/hexane) 116–120° C. $^1$H NMR [400 MHz, $(CD_3)_2SO$] δ 8.79 (s, 1H), 7.79 (ddd, J=8.3, 5.9, 2.0 Hz, 1 H), 7.30 (dd, J=12.2, 1.8 Hz, 1 H), 7.26–7.17 (m, 1 H), 7.15 (dd, J=8.5, 1.6 Hz, 1 H), 6.92 (ddd, J=8.8, 8.8, 4.7 Hz, 1 H), 5.31 (br s, 1 H), 4.28 (s, 2 H), 3.81 (s, 3 H). Anal. calcd. for $C_{17}H_{12}F_3NO_3$: C, 60.9; H, 3.6; N, 4.2. Found C, 61.4; H, 3.9; N, 4.7.

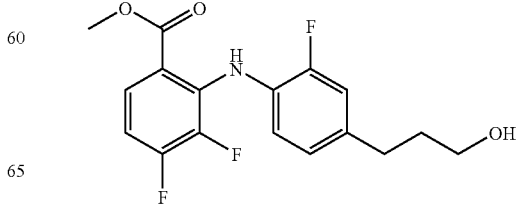

Step B: Preparation of methyl 3,4-difluoro-2-[2-fluoro-4-(3-hydroxypropyl)anilino]benzoate Methyl 3,4-difluoro-2-[2-fluoro-4-(3-hydroxy-1-propynyl)anilino]benzoate was dissolved in absolute EtOH and hydrogenated in the presence of 5% Pd/C by the general procedure of Example 1, Step D. Purification of the resulting oil was carried out by column chromatography on silica gel (20% EtOAc/PE as eluant) to give methyl 3,4-difluoro-2-[2-fluoro-4-(3-hydroxypropyl)anilino]benzoate as a waxy white solid (93%), used directly in the next step. $^1$H NMR [400 MHz, (CD$_3$)$_2$SO] δ 8.81 (s, 1 H), 7.78 (ddd, J=9.0, 6.1, 2.0 Hz, 1 H), 7.10–7.02 (m, 2 H), 6.98 (ddd, J=8.3, 8.3, 4.0 Hz, 1 H), 6.94 (dd, J=8.2, 1.9 Hz, 1 H), 4.46 (t, J=4.8 Hz, 1 H), 3.82 (s, 3 H), 3.43–3.37 (m, 2 H), 2.58 (t, J=7.7 Hz, 2 H), 1.74–1.66 (m, 2 H). LCMS (APCI–) 338 (M–H).

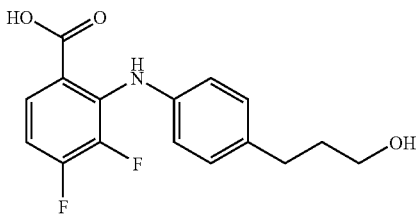

Step C: Preparation of 3,4-difluoro-2-[2-fluoro-4-(3-hydroxypropyl)anilino]benzoic acid Methyl 3,4-difluoro-2-[2-fluoro-4-(3-hydroxypropyl)anilino]benzoate was deprotected using EtOH/1 M NaOH as above to afford, after workup, 3,4-difluoro-2-[2-fluoro-4-(3-hydroxypropyl)anilino]benzoic acid as a white solid (99%); m.p. (EtOAc/hexane) 130–133° C. $^1$H NMR [400 MHz, (CD$_3$)$_2$SO] δ 13.66 (br s, 1 H), 9.25 (br s, 1 H), 7.81 (ddd, J=8.5, 6.1, 1.9 Hz, 1 H), 7.08 (dd, J=12.6, 1.7 Hz, 1 H), 7.05–6.96 (m, 2 H), 6.93 (dd, J=8.2, 1.6 Hz, 1 H), 4.63 (br s, 1 H), 3.40 (t, J=6.3 Hz, 2 H), 2.59 (t, J=7.7 Hz, 2 H), 1.74–1.65 (m, 2 H). Anal. calcd. for C$_{16}$H$_{14}$F$_3$NO$_3$: C, 59.1; H, 4.3; N, 4.3. Found C, 59.2; H, 4.4; N, 4.3.

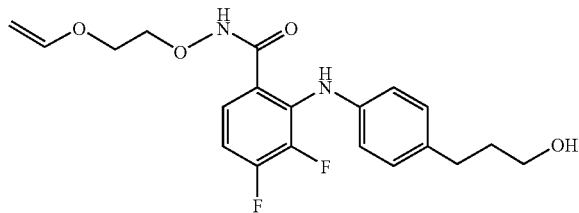

Step D: Preparation of 3,4-difluoro-2-[2-fluoro-4-(3-hydroxypropyl)anilino]-N-[2 (vinyloxy)ethoxy]benzamide The title compound was prepared from reaction of 3,4-difluoro-2-[2-fluoro-4-(3-hydroxypropyl)anilino]benzoic acid with 1-[2-(aminooxy)ethoxy]ethylene and DMT-MM by the general procedure of Example 6, Step B, then purified by column chromatography on silica gel (20% EtOAc/PE as eluant) to give 3,4-difluoro-2-[2-fluoro-4-(3-hydroxypropyl)anilino]-N-[2-(vinyloxy)ethoxy]benzamide as a white solid (46%), which was employed directly in the next step. $^1$H NMR [400 MHz, (CD$_3$)$_2$SO] δ 11.93 (br s, 1 H), 8.79 (br s, 1 H), 7.44–7.38 (m, 1 H), 7.14–7.05 (m, 1H), 7.04 (dd, J=12.6, 1.6 Hz, 1 H), 6.89 (dd, J=8.2, 1.6 Hz, 1 H), 6.82 (ddd, J=8.7, 8.7, 4.4 Hz, 1 H), 6.50 (dd, J=14.3, 6.7 Hz, 1 H), 4.45 (t, J=5.1 Hz, 1 H), 4.18 (dd, J=14.3, 1.9 Hz, 1 H), 4.06–4.01 (m, 2 H), 3.98 (dd, J=6.6, 1.9 Hz, 1 H), 3.89–3.82 (m, 2 H), 3.42–3.35 (m, 2 H), 2.56 (t, J=7.7 Hz, 2 H), 1.72–1.64 (m, 2 H). LCMS (APCI–) 409 (M–H).

Step E: Preparation of 3,4-difluoro-2-[2-fluoro-4-(3-iodopropyl)anilino]-N-[2-(vinyloxy)ethoxy]benzamide 3,4-Difluoro-2-[2-fluoro-4-(3-hydroxypropyl)anilino]-N-[2-(vinyloxy)ethoxy]benzamide (710 mg, 1.73 mmol) was dissolved in THF (10 mL), to which was added TEA (875 mg, 8.65 mmol), followed by methanesulfonyl chloride (396 mg, 3.46 mmol). This mixture was stirred at RT for 1 hour, then partitioned between water (100 mL) and EtOAc (100 mL). The EtOAc layer was washed with water (100 mL), sat. NaHCO$_3$ (100 mL), brine (100 mL) and dried (Na$_2$SO$_4$). The solvent was removed under reduced pressure to give a bright yellow oil (844 mg, 1.73 mmol) which was dissolved in EtOAc (15 mL). NaI (5.19 g, 34.6 mmol) was added, and the mixture heated to 70° C. for 1.5 hours, at which time complete reaction was observed by TLC. The excess NaI was removed by filtration, and the EtOAc removed from the filtrate under reduced pressure to afford a yellow oil which was purified by chromatography on silica gel (10% EtOAc/PE as eluant). 3,4-Difluoro-2-[2-fluoro-4-(3-iodopropyl)anilino]-N-[2-(vinyloxy)ethoxy]benzamide was isolated as a pale yellow oil (474 mg, 53%). $^1$H NMR [400 MHz, (CD$_3$)$_2$SO] δ 8.45 (s, 1 H), 7.50 (ddd, J=9.0, 5.8, 1.8 Hz, 1 H), 7.26–7.17 (m, 1 H), 7.10 (dd, J=12.7, 1.7 Hz, 1 H), 6.96–6.86 (m, 2 H), 6.38 (dd, J=14.3, 6.7 Hz, 1 H), 4.44–4.39 (m, 1 H), 4.15 (dd, J=14.3, 1.9 Hz, 1 H), 3.97–3.91 (m, 2 H), 3.59 (br s, 2 H), 3.22 (t, J=6.7 Hz, 2 H), 2.63 (t, J=7.4 Hz, 2 H), 2.05 (pentet, J=7.1 Hz, 2 H). Not all exchangeable protons were observed. HRMS (E+) calcd for C$_{20}$H$_{20}$F$_3$N$_2$O$_3$I 520.0471 (M+), found 520.0467.

Step F: Preparation of 2-{4-[3-(dimethylamino)propyl]-2-fluoroanilino}-3,4-difluoro-N-(2-hydroxyethoxy)benzamide 3,4-Difluoro-2-[2-fluoro-4-(3-iodopropyl)anilino]-N-[2-(vinyloxy)ethoxy]benzamide (200 mg, 0.39 mmol) was dissolved in DMA (10 mL), to which was added dimethylamine (0.15 mL of a 40% solution in water). This mixture was stirred at RT for 15 hours, then the DMA removed under reduced pressure, affording a yellow oil. This oil was then dissolved in EtOH (6 mL), to which was added 1 M HCl solution (4 mL). The resulting mixture was stirred at RT for 15 h. The reaction mixture was then diluted with water (50 mL) and this aqueous solution basicified with solid K$_2$CO$_3$ and saturated with solid NaCl. The resulting solution was extracted with EtOAc (3×50 mL), the combined organic extract dried (Na$_2$SO$_4$) and the solvent removed under reduced pressure to afford an oil. This oil was purified by column chromatography on silica gel (1% NH$_4$OH in 25% MeOH/CH$_2$Cl$_2$ as eluant) to give 2-{4-[3-(dimethylamino)propyl]-2-fluoroanilino}-3,4-difluoro-N-(2-hydroxyethoxy)benzamide as a cream foam (55 mg, 36%). $^1$H NMR [400 MHz, (CD$_3$)$_2$SO] δ 11.70 (v br s, 1 H), 8.82 (br s, 1 H), 7.44–7.38 (m, 1 H), 7.14–7.06 (m, 1H), 7.05 (dd, J=12.5, 1.6 Hz, 1 H), 6.89 (dd, J=8.2, 1.6 Hz, 1 H), 6.82 (ddd, J=8.7, 8.7, 4.5 Hz, 1 H), 4.53 (br s, 1 H), 3.85 (t, J=4.9 Hz, 2 H), 3.57 (t, J=4.9 Hz, 2 H), 2.53 (t, J=7.5 Hz, 2 H), 2.24 (t, J=7.1 Hz, 2 H), 2.16 (s, 6 H), 1.67 (q, J=7.5 Hz, 2H). Anal. calcd. for C$_{20}$H$_{24}$F$_3$N$_3$O$_3$·0.75H$_2$O: C, 56.5; H, 6.1; N, 9.9. Found C, 56.4; H, 6.4; N, 9.1.

EXAMPLE 16

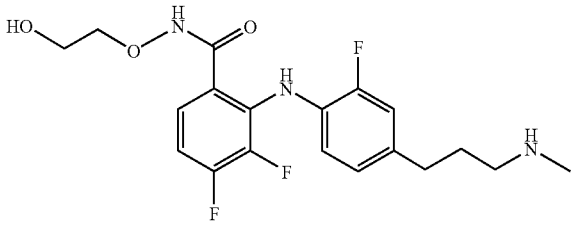

3,4-Difluoro-2-{2-fluoro-4-[3-(methylamino)propyl]anilino}-N-(2-hydroxyethoxy)benzamide The product of Example 15, Step E, 3,4-Difluoro-2-[2-fluoro-4-(3-iodopropyl)anilino]-N-[2-(vinyloxy)ethoxy]benzamide was reacted with methylamine and then deprotected according to the general procedure of Example 15, Step F, to afford 3,4-difluoro-2-{2-fluoro-4-[3-(methylamino)propyl] anilino}-N-(2-hydroxyethoxy)benzamide as a pale brown solid (32%); m.p. (Et$_2$O) 112–116° C. $^1$H NMR [400 MHz, (CD$_3$)$_2$SO] δ 9.61 (v br s, 1 H), 7.57–7.50 (m, 1 H), 7.02–6.94 (m, 1H), 6.93 (dd, J=12.4, 1.5 Hz, 1 H), 6.79 (dd, J=8.3, 1.5 Hz, 1 H), 6.65 (ddd, J=8.8, 8.8, 5.9 Hz, 1 H), 3.80 (t, J=4.9 Hz, 2 H), 3.54 (t, J=4.9 Hz, 2 H), 2.66 (t, J=7.3 Hz, 2 H), 2.52 (t, J=7.6 Hz, 2 H), 2.41 (s, 3 H), 1.73 (q, J=7.5 Hz, 2 H). Not all exchangeable protons were observed. Anal. calcd. for C$_{19}$H$_{22}$F$_3$N$_3$O$_3$·0.5H$_2$O: C, 56.2; H, 5.7; N, 10.3. Found C, 56.2; H, 5.6; N, 10.2.

EXAMPLE 17

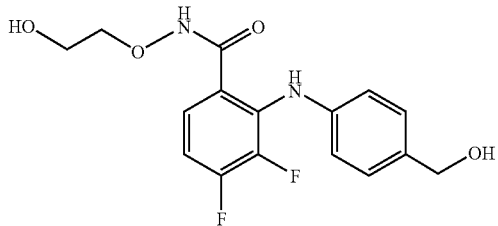

3,4-Difluoro-N-(2-hydroxyethoxy)-2-[[4-(hydroxymethyl)phenyl]amino]benzamide

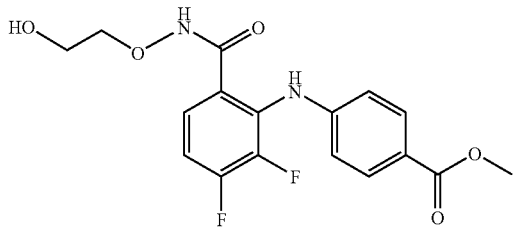

Step A: Preparation of methyl 4-[[2,3-difluoro-6-[[(2-hydroxyethoxy)amino]carbonyl]phenyl]amino]benzoate 2,3,4-Trifluorobenzoic acid and methyl 4-aminobenzoate were reacted in the presence of LiHMDS solution in THF by the general procedure of Example 1, Step B, to afford after workup, crude 3,4-difluoro-2-[[4-(methoxycarbonyl)-phenyl]amino]benzoic acid as a cream solid. This material was then coupled directly with 2-(aminooxy)ethanol by the general procedure of Example 1; Step E, and purified on flash silica (10% EtOAc as eluant) to give methyl 4-[[2,3-difluoro-6-[[(2-hydroxyethoxy)amino]carbonyl]phenyl]amino]benzoate (48%) as a white solid; m.p. (EtOAc/hexanes) 158–160° C. $^1$H NMR [400 MHz, (CD$_3$)$_2$SO] δ 11.64 (br s, 1 H), 8.76 (br s, 1 H), 7.78 (d, J=8.8 Hz, 2 H), 7.41–7.27 (m, 2 H), 6.80 (dd, J=8.8, 1.8 Hz, 2 H), 4.67 (br s, 1 H), 3.78 (s, 3 H), 3.76 (t, J=4.8 Hz, 2 H), 3.50 (t, J=4.6 Hz, 2 H). Anal. Calcd for C$_{17}$H$_{16}$F$_2$N$_2$O$_5$: C, 55.7; H, 4.4; N, 7.7. Found: C, 55.7; H, 4.4; N, 7.6.

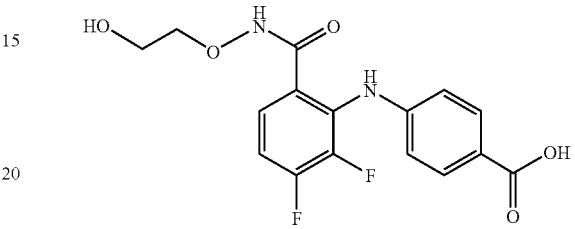

Step B: Preparation of 4-[[2,3-difluoro-6-[[(2-hydroxyethoxy)amino]carbonyl]-phenyl]amino]benzoic acid The product of Example 17, Step A, methyl 4-[[2,3-difluoro-6-[[(2-hydroxyethoxy)amino]carbonyl]phenyl]amino]benzoate (306 mg, 0.84 mmol) was dissolved in ethanol (40 mL), to which was added 1 M NaOH solution (40 mL). This mixture was stirred at room temperature for 15 hours, then poured into 1 M HCl solution (100 mL). The resulting precipitate was extracted with EtOAc (3×80 mL) and the combined EtOAc extracts then combined and washed with water (2×100 mL) and saturated NaCl (100 mL). The organic fraction was dried (Na$_2$SO$_4$), the solvent removed under reduced pressure and the resulting residue purified by column chromatography on flash silica (50% EtOAc/hexanes as eluant) to afford 4-[[2,3-difluoro-6-[[(2-hydroxyethoxy)amino]carbonyl]phenyl]-amino]benzoic acid as a crystalline white solid (168 mg, 57%); m.p. (EtOAc/hexanes) 180–183° C.

$^1$H NMR [400 MHz, (CD$_3$)$_2$SO] δ 11.89 (br s, 2 H), 8.75 (br s, 1 H), 7.75 (d, J=8.8 Hz, 2 H), 7.41–7.25 (m, 2 H), 6.79 (dd, J=8.6, 1.7 Hz, 2 H), 4.76 (br s, 1 H), 3.76 (t, J=4.8 Hz, 2 H), 3.50 (t, J=4.8 Hz, 2 H). Anal. Calcd for C$_{16}$H$_{14}$F$_2$N$_2$O$_5$: C, 54.5; H, 4.0; N, 8.0. Found: C, 54.8; H, 3.9; N, 8.0.

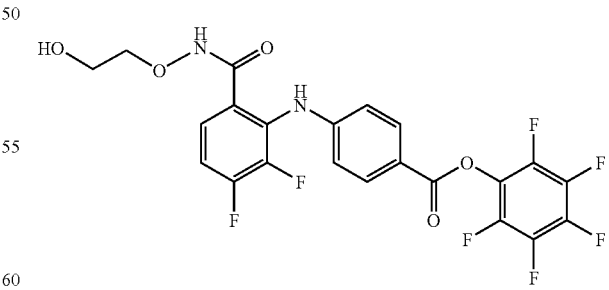

Step C: Preparation of 2,3,4,5,6-pentafluorophenyl 4-[[2,3-difluoro-6-[[(2-hydroxyethoxy)-amino]carbonyl]-phenyl]amino]benzoate The product of Example 17, Step B, 4-[[2,3-difluoro-6-[[(2-hydroxyethoxy)amino]carbonyl]phenyl]amino]benzoic acid (265 mg, 0.75 mmol), was dissolved in dry DMA (3 mL). The flask was sealed and flushed with nitrogen, then pyridine (65 mg, 0.83 mmol) and pentafluorophenyltrifluoroacetate (232 mg, 0.83 mmol) was added via syringe. This reaction mixture was stirred at room temperature for 15 hours, then all solvent was removed under reduced pressure. The residue was partitioned between 1 M HCl (50 mL) and EtOAc (50 mL), then the EtOAc layer washed with water (50 mL), saturated NaCl (50 mL), dried ($Na_2SO_4$). The solvent was removed under reduced pressure to give an oil which was purified by column chromatography on flash silica (10% EtOAc/hexanes as eluant) to afford 2,3,4,5,6-pentafluorophenyl 4-[[2,3-difluoro-6-[[(2-hydroxyethoxy)amino]carbonyl]phenyl]amino]benzoate (156 mg, 40%) as a white solid. $^1$H NMR [400 MHz, $(CD_3)_2SO$] δ 11.65 (br s, 1 H), 9.01 (br s, 1 H), 7.96 (d, J=8.8 Hz, 2 H), 7.45–7.36 (m, 2 H), 6.88 (dd, J=8.6, 1.3 Hz, 2 H), 4.67 (br s, 1 H), 3.81–3.72 (m, 2 H), 3.54–3.46 (m, 2 H). HRMS (EI$^+$) calcd for $C_{22}H_{13}F_7N_2O_5$ 518.0713 (M+), found 518.0702.

Step D: Preparation of 3,4-difluoro-N-(2-hydroxyethoxy)-2-[[4(hydroxymethyl)phenyl]amino]benzamide The product of Example 17, Step C, 2,3,4,5,6-pentafluorophenyl 4-[[2,3-difluoro-6-[[(2-hydroxyethoxy)amino]carbonyl]phenyl]amino]benzoate (150 mg, 0.29 mmol) was dissolved in THF (2 mL), then added dropwise to a solution of NaBH$_4$ (110 mg, 2.90 mmol) in water (2 mL). This mixture was stirred at room temperature for 2 hours, acidified with 1 M HCl, and diluted with water (50 mL). The resulting aqueous mixture was extracted with EtOAc (2×50 mL), then the combined EtOAc fractions washed with water (50 mL), saturated NaCl (50 mL), and dried ($Na_2SO_4$). The solvent was removed under reduced pressure and the resulting residue purified by column chromatography on flash silica (50% EtOAc/hexanes as eluant) to afford 3,4-difluoro-N-(2-hydroxyethoxy)-2-[[4-(hydroxymethyl)phenyl]amino]benzamide as a cream solid (36 mg, 37%); m.p. (EtOAc/hexanes) 73–77° C. $^1$H NMR [400 MHz, $(CD_3)_2SO$] δ 11.73 (br s, 1 H), 8.68 (br s, 1 H), 7.41–7.35 (m, 1H), 7.15 (d, J=8.5 Hz, 2 H), 7.14–7.06 (m, 1 H), 6.79 (dd, J=8.5, 2.3 Hz, 2 H), 4.99 (t, J=5.7 Hz, 1 H), 4.72 (br s, 1 H), 4.38 (d, J=5.6, 2 H), 3.80 (t, J=4.9 Hz, 2 H), 3.54 (t, J=4.9 Hz, 2 H). Anal. Calcd for $C_{16}H_{16}F_2N_2O_4$: C, 56.8; H, 4.8; N, 8.3. Found: C, 56.3; H, 4.7; N, 8.1.

EXAMPLE 18

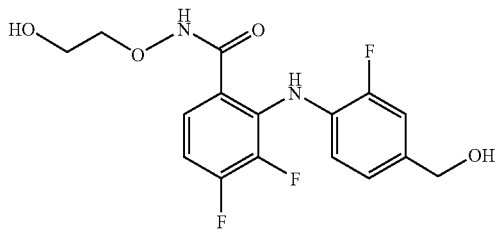

3,4-Difluoro-2-[2-fluoro-4-(hydroxymethyl)anilino]-N-(2-hydroxyethoxy)benzamide

The product of Example 4,3,4-Difluoro-2-(2-fluoro-4-vinylanilino)-N-(2-hydroxyethoxy)benzamide (170 mg, 0.48 mmol) was dissolved in MeOH (50 mL) and the solution cooled to −78° C. (acetone/dry ice). Ozone was bubbled through the solution until a pale blue-grey solution was obtained, then nitrogen bubbled through the solution until the blue colour disappeared. A solution of NaBH$_4$ (92 mg, 2.41 mmol) in MeOH (10 mL) was added, the reaction mixture removed from the cold bath and allowed to stir for 0.5 h. at RT. The MeOH was removed from the mixture under reduced pressure and the resulting residue partitioned between EtOAc (50 mL) and 1 M HCl (50 mL). The EtOAc layer was washed with water (50 mL) and brine (50 mL), then dried ($Na_2SO_4$) and the solvent removed under reduced pressure to afford an oil which was purified by chromatography on silica gel (10% EtOAc as eluant). 3,4-Difluoro-2-[2-fluoro-4-(hydroxymethyl)anilino]-N-(2-hydroxyethoxy)benzamide was isolated as a pale yellow crystalline solid (99 mg, 58%); m.p. (Et$_2$O/hexane) 108–110° C. $^1$H NMR [400 MHz, $(CD_3)_2SO$] δ 11.86 (br s, 1 H), 8.74 (br s, 1 H), 7.44–7.37 (m, 1 H), 7.16–7.08 (m, 2 H), 7.02–6.97 (m, 1 H), 6.86 (ddd, J=8.6, 8.6, 4.5 Hz, 1 H), 5.18 (t, J=5.7 Hz, 1 H), 4.71 (br s, 1 H), 4.43 (d, J=5.8 Hz, 2 H), 3.85 (t, J=4.7 Hz, 2 H), 3.60–3.52 (m, 2 H). Anal. calcd. for $C_{16}H_{15}F_3N_2O_4$: C, 53.9; H, 4.2; N, 7.9. Found C, 54.2; H, 4.6; N, 7.6.

EXAMPLE 19

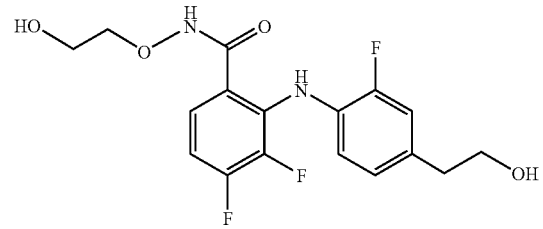

3,4-Difluoro-2-[2-fluoro-4-(2-hydroxyethyl)anilino]-N-(2-hydroxyethoxy)benzamide

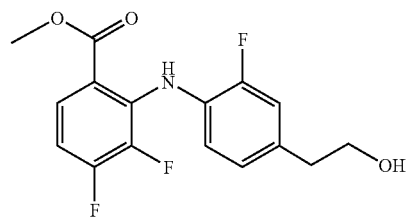

Step A: Preparation of methyl 3,4-difluoro-2-[2-fluoro-4-(2-hydroxyethyl)anilino]benzoate Crude methyl 2-(4-allyl-2-fluoroanilino)-3,4-difluorobenzoate, prepared as above, was subjected to ozonolysis and reduction with NaBH$_4$ as above to afford methyl 3,4-difluoro-2-[2-fluoro-4-(2-hydroxyethyl)anilino]benzoate as a pale yellow oil (37%). $^1$H NMR [400 MHz, $(CD_3)_2SO$] δ 8.82 (br s, 1 H), 7.78 (ddd, J=8.3, 6.1, 2.0 Hz, 1 H), 7.13–6.92 (m, 4 H), 4.64 (t, J=5.2 Hz, 1 H), 3.83 (s, 3 H), 3.60 (q, J=6.3 Hz, 2 H), 2.69 (t, J=6.9 Hz, 2 H). LCMS (APCI+) 326 (M+H).

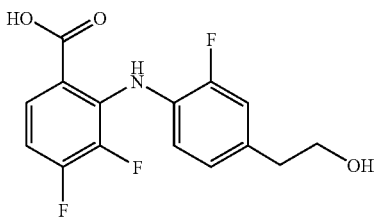

Step B: Preparation of 3,4-difluoro-2-[2-fluoro-4-(2-hydroxyethyl)anilino]benzoic acid Methyl 3,4-difluoro-2-[2-fluoro-4-(2-hydroxyethyl)anilino]benzoate was deprotected using EtOH/1 M NaOH as above to afford 3,4-difluoro-2-[2-fluoro-4-(2-hydroxyethyl)anilino]benzoic acid as a crystalline cream solid (93%); m.p. (EtOAc/hexane) 196–200° C. $^1$H NMR [400 MHz, (CD$_3$)$_2$SO] δ 13.67 (v br s, 1 H), 9.28 (br s, 1 H), 7.80 (ddd, J=8.4, 6.1, 1.8 Hz, 1 H), 7.13–6.93 (m, 4 H), 4.65 (br s, 1H), 3.63–3.55 (br m, 2 H), 2.69 (t, J=6.8 Hz, 2 H). Anal. calcd. for C$_{15}$H$_{12}$F$_3$NO$_3$: C, 57.9; H, 3.9; N, 4.5. Found C, 58.3; H, 4.1; N, 4.7.

Step C: Preparation of 3,4-difluoro-2-[2-fluoro-4-(2-hydroxyethyl)anilino]-N-(2-hydroxyethoxy)benzamide 3,4-Difluoro-2-[2-fluoro-4-(2-hydroxyethyl)anilino]benzoic acid was dissolved in MeOH and prepared from reaction with 2(aminooxy)ethanol and DMT-MM by the general procedure of Example 6, Step B, affording a crude yellow oil after workup which was purified by filtration through a plug of silica gel (100% EtOAc as eluant). 3,4-Difluoro-2-[2-fluoro-4-(2-hydroxyethyl)anilino]-N-(2-hydroxyethoxy)benzamide was isolated as a viscous, transparent oil (57%). $^1$H NMR [400 MHz, (CD$_3$)$_2$SO] δ 11.85 (v br s, 1 H), 8.77 (br s, 1 H), 7.44–7.37 (m, 1 H), 7.15–7.05 (m, 1 H), 7.06 (dd, J=12.5, 1.7 Hz, 1 H), 6.90 (dd, J=8.2, 1.7 Hz, 1 H), 6.81 (ddd, J=8.8, 8.8, 4.5 Hz, 1 H), 4.75 (br s, 1 H), 4.63 (t, J=5.2 Hz, 1H), 3.86 (t, J=5.0 Hz, 2 H), 3.61–3.52 (m, 4 H), 2.66 (t, J=6.9 Hz, 2 H). HRMS (EI$^+$) calcd. for C$_{20}$H$_{16}$F$_2$N$_2$O$_3$ 370.1129 (M$^+$), found 370.1133.

EXAMPLE 20

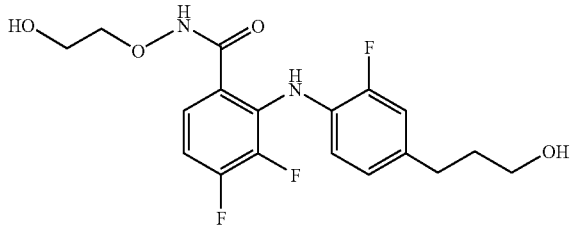

3,4-Difluoro-2-[2-fluoro-4-(3-hydroxypropyl)anilino]-N-(2-hydroxyethoxy)benzamide The product of Example 10, Step D, 3,4-Difluoro-2-[2-fluoro-4-(3-hydroxy-1-propynyl)anilino]-N-(2-hydroxyethoxy)-benzamide was hydrogenated in absolute EtOH in the presence of 5% Pd/C by the procedure of Example 1, Step D. An off-white solid was isolated which was purified by filtration through a plug of silica gel (EtOAc as eluant). 3,4-Difluoro-2-[2-fluoro-4-(3-hydroxypropyl)anilino]-N-(2-hydroxyethoxy)benzamide was isolated as a crystalline cream solid (52 mg, 73%); m.p. (EtOAc/Et$_2$O) 115–116° C. $^1$H NMR [400 MHz, (CD$_3$)$_2$SO] δ 11.85 (br s, 1 H), 8.83 (br s, 1 H), 7.44–7.37 (m, 1 H), 7.13–7.05 (m, 1 H), 7.03 (dd, J=12.6, 1.6 Hz, 1H), 6.88 (dd, J=8.2, 1.6 Hz, 1 H), 6.81 (ddd, J=8.7, 8.7, 4.5 Hz, 1 H), 4.76 (br s, 1H), 4.46 (t, J=5.1 Hz, 1 H), 3.86 (t, J=4.8 Hz, 2 H), 3.57 (t, J=5.0 Hz, 2 H), 3.43–3.35 (m, 2 H), 2.58–2.52 (m, 2 H), 1.72–1.64 (m, 2 H). Anal. calcd. for C$_{18}$H$_{19}$F$_3$N$_2$O$_4$·0.5Et$_2$O: C, 57.0; H, 5.7; N, 6.7. Found C, 56.6; H, 5.5; N, 6.8.

EXAMPLE 21

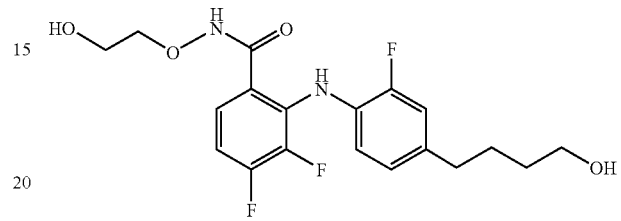

3,4-Difluoro-2-[2-fluoro-4-(4-hydroxybutyl)anilino]-N-(2-hydroxyethoxy)benzamide The product of Example 11, 3,4-Difluoro-2-[2-fluoro-4-(4-hydroxy-1-butynyl)anilino]-N-(2-hydroxyethoxy)-benzamide was hydrogenated in absolute EtOH in the presence of 5% Pd/C by the procedure of Example 1, Step D. Purification of the resulting oil was carried out by filtration through a plug of silica gel (EtOAc as eluant) to afford 3,4-difluoro-2-[2-fluoro-4-(4-hydroxybutyl)anilino]-N-(2-hydroxyethoxy)benzamide as a white crystalline solid (46%); m.p. (Et$_2$O/EtOAc) 65-69° C. $^1$H NMR [400 MHz, (CD$_3$)$_2$SO] δ 11.90 (br s, 1 H), 8.83 (br s, 1 H), 7.44–7.38 (m, 1 H), 7.13–7.07 (m, 1 H), 7.03 (dd, J=12.5, 1.6 Hz, 1 H), 6.88 (dd, J=8.2, 1.7 Hz, 1 H), 6.82 (ddd, J=8.7, 8.7, 4.3 Hz, 1 H), 4.76 (v br s, 1 H), 4.35 (t, J=5.2 Hz, 1H), 3.84 (t, J=4.8 Hz, 2 H), 3.56 (t, J=4.9 Hz, 2 H), 3.43–3.34 (m, 2 H), 2.55–2.47 (m, 2 H), 1.61–1.51 (m, 2 H), 1.46–1.37 (m, 2 H). Anal. calcd. for C$_{19}$H$_{21}$F$_3$N$_2$O$_4$: C, 57.3; H, 5.3; N, 7.0. Found C, 57.4; H, 5.4; N, 6.9.

EXAMPLE 22

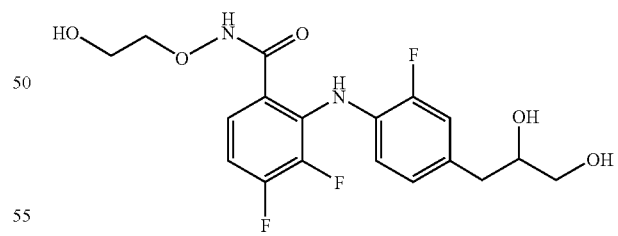

2-[4-(2,3-Dihydroxypropyl)-2-fluoroanilino]-3,4-difluoro-N-(2-hydroxyethoxy)benzamide The product of Example 6,2-(4-allyl-2-fluoroanilino)-3,4-difluoro-N-(2-hydroxyethoxy)benzamide (227 mg, 0.62 mmol) was dissolved in tert-butanol (15 mL) and water (15 mL) to which was added K$_2$CO$_3$ (257 mg, 1.86 mmol), K$_3$Fe(CN)$_6$ (613 mg, 1.86 mmol) and 1,4-diazabicyclo[2.2.2]octane (70 mg, 0.62 mmol). To this mixture was then added a 4% w/w solution of OsO$_4$ in water (0.21 ml, 0.031 mmol). The reaction was then stirred 15 h. at room temperature, poured into 10% Na$_2$S$_2$O$_4$ (100 mL), and this aqueous solution extracted with EtOAc (3×80 mL). The EtOAc extracts were combined, washed with saturated NaCl solution and dried (Na$_2$SO$_4$), then the solvent removed under reduced pressure to afford a viscous oil. This oil was purified by flash chromatography on silica (10% MeOH/CH$_2$Cl$_2$ as eluant) to give 2-[4-(2,3-dihydroxypropyl)-2-fluoroanilino]-3,4-difluoro-N-(2-hydroxyethoxy)benzamide as a cream solid (159 mg, 64%); m.p. (Et$_2$O) 118–120° C. $^1$H NMR [400 MHz, (CD$_3$)$_2$SO] δ 11.86 (br s, 1 H), 8.78 (br s, 1 H), 7.44–7.37 (m, 1H), 7.14–7.08 (m, 1 H), 7.05 (dd, J=12.8, 1.7 Hz, 1 H), 6.90 (dd, J=8.2, 1.6 Hz, 1H), 6.81 (ddd, J=8.8, 8.8, 4.5 Hz, 1 H), 4.71 (br s, 1 H), 4.55 (t, J=6.1 Hz, 2 H), 3.57 (t, J=4.9 Hz, 2 H), 3.63–3.55 (m, 2 H), 3.30–3.20 (m, 2 H), 2.71 (dd, J=13.8, 4.5 Hz, 1 H), 2.43–2.49 (m, 2 H). HRMS (EI$^+$) calcd. For C$_{18}$H$_{19}$F$_3$N$_2$O$_5$ 400.1246 (M+), found 400.1248. Anal. calcd. for C$_{18}$H$_{19}$F$_3$N$_2$O$_5$: C, 54.0; H, 4.8; N, 7.0. Found: C, 54.0; H, 4.8; N, 7.0.

EXAMPLE 23

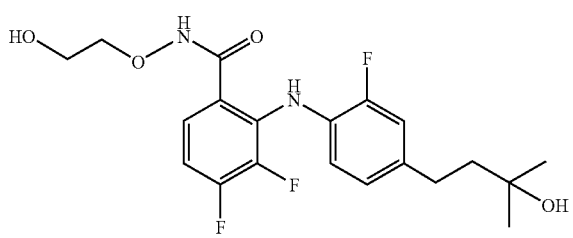

3,4-Difluoro-2-[2-fluoro-4-(3-hydroxy-3-methylbutyl)anilino]-N-(2-hydroxyethoxy)benzamide The product of Example 12, 3,4-difluoro-2-[2-fluoro-4-(3-hydroxy-3-methyl-1-butynyl)anilino]-N-(2-hydroxyethoxy)benzamide was hydrogenated in absolute ethanol in the presence of 5% Pd/C by the general procedure of Example 1, Step D. The resulting crude solid was purified by filtration through a plug of silica (MeOH as eluant) to give 3,4-difluoro-2-[2-fluoro-4-(3-hydroxy-3-methylbutyl)anilino]-N-(2-hydroxyethoxy)benzamide (99%) as a cream foam (hygroscopic). $^1$H NMR [400 MHz, (CD$_3$)$_2$SO] δ 10.09 (br s, 1 H), 7.60–7.55 (m, 1 H), 7.03–6.91 (m, 2 H), 6.86 (dd, J=8.2, 1.4 Hz, 1 H), 6.71 (ddd, J=8.6, 8.6, 5.8 Hz, 1 H), 4.22 (br s, 1 H), 3.79 (t, J=4.9 Hz, 2 H), 3.55 (t, J=4.9 Hz, 2 H), 2.60–2.49 (m, 2 H), 1.65–1.59 (m, 2 H), 1.13 (s, 6 H). HRMS (EI$^+$) calcd for C$_{20}$H$_{23}$F$_3$N$_2$O$_4$ 412.1610 (M+), found 412.1617.

EXAMPLE 24

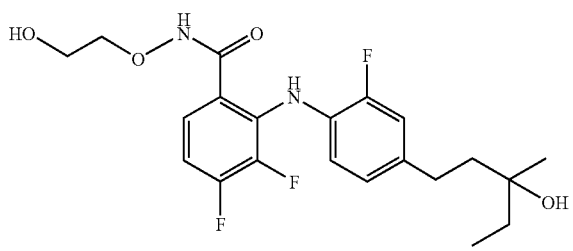

3,4-Difluoro-2-[2-fluoro-4-(3-hydroxy-3-methylpentyl)anilino]-N-(2-hydroxyethoxy)benzamide The product of Example 13, 3,4-difluoro-2-[2-fluoro-4-(3-hydroxy-3-methyl-1-pentynyl)anilino]-N-(2-hydroxyethoxy)benzamide was hydrogenated in absolute ethanol in the presence of 5% Pd/C by the general procedure of Example 1, Step D. The resulting crude solid was purified by filtration through a plug of silica (MeOH as eluant) to give 3,4-difluoro-2-[2-fluoro-4-(3-hydroxy-3-methylpentyl)anilino]-N-(2-hydroxyethoxy)benzamide (98%) as a light yellow foam (hygroscopic). $^1$H NMR [400 MHz, (CD$_3$)$_2$SO] δ 9.62 (br s, 1 H), 7.54–7.48 (m, 1 H), 7.04–6.96 (m, 2 H), 6.86 (dd, J=8.2, 1.6 Hz, 1 H), 6.75 (ddd, J=8.6, 5.2 Hz, 1 H), 4.08 (br s, 1 H), 3.80 (t, J=4.9 Hz, 2 H), 3.53 (t, J=4.9 Hz, 2 H), 2.55–2.50 (m, 2 H), 1.60–1.54 (m, 2 H), 1.41 (q, I=7.6 Hz, 2 H), 1.06 (s, 3 H), 0.84 (t, J=7.6 Hz, 3 H). HRMS (EI$^+$) calcd for C$_{21}$H$_{25}$F$_3$N$_2$O$_4$ 426.1766 (M$^+$), found 426.1770.

EXAMPLE 25

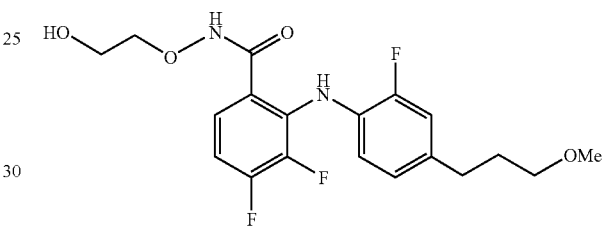

3,4-Difluoro-2-[[2-fluoro-4-(3-methoxypropyl)phenyl]amino]-N-(2-hydroxyethoxy)benzamide

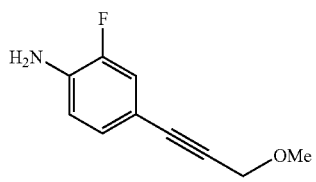

Step A: Preparation of 2-fluoro-4-(3-methoxy-1-propynyl)aniline

2-Fluoro-4-iodoaniline and methyl propargyl ether were combined by the general procedure of Example 1, Step A, to prepare 2-fluoro-4-(3-methoxy-1-propynyl)aniline. The desired product was isolated as a dark orange solid (91%); $^1$H NMR [400 MHz, (CD$_3$)$_2$SO] δ 7.07 (dd, J=12.2, 1.8 Hz, 1 H), 6.98 (dd, J=8.2, 1.7 Hz, 1 H), 6.71 (dd, J=9.3, 8.4 Hz, 1 H), 5.56 (s, 2 H), 4.26 (s, 2 H), 3.29 (s, 3 H).

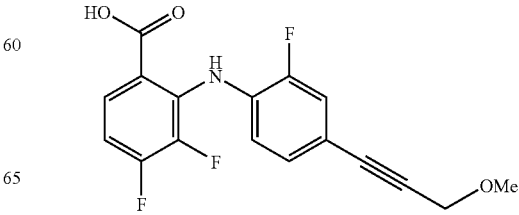

Step B: Preparation of 3,4-difluoro-2-[[2-fluoro-4-(3-methoxy-1-propynyl)phenyl]amino]benzoic acid 2,3,4-Trifluorobenzoic acid and the product of Example 25, Step A, 2-fluoro-4-(3-methoxy-1-propynyl)aniline, were reacted in the presence of LiHMDS solution in THF by the general procedure of Example 1, Step B. After workup, followed by purification by chromatography on silica gel (10% EtOAc/hexanes as eluant), 3,4-difluoro-2-[[2-fluoro-4-(3-methoxy-1-propynyl)phenyl]amino]-benzoic acid was isolated (62%) as a pale yellow solid; m.p. (EtOAc/hexanes) 221–223° C. $^1$H NMR [400 MHz, (CD$_3$)$_2$SO] δ 13.60 (br s, 1 H), 9.27 (br s, 1 H), 7.85–7.79 (m, 1H,), 7.36 (dd, J=12.0, 1.8 Hz, 1 H), 7.20 (dd, J=8.3, 1.5 Hz, 1 H), 7.18–7.11 (m, 1 H), 6.96 (td, 8.8, 5.5 Hz, 1 H), 4.31 (s, 2 H), 3.32 (s, 3 H). Anal. Calcd for C$_{17}$H$_{12}$F$_3$NO$_3$: C, 60.9; H, 3.6; N, 4.2. Found: C, 61.4; H, 3.6; N, 4.2.

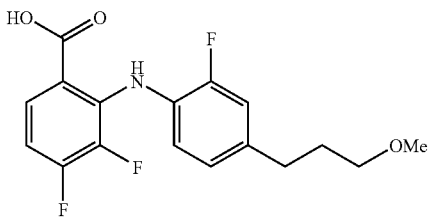

Step C: Preparation of 3,4-difluoro-2-[[2-fluoro-4-(3-methoxypropyl)phenyl]-amino]benzoic acid The product of Example 25, Step B, 3,4-difluoro-2-[[2-fluoro-4-(3-methoxy-1-propynyl)phenyl]amino]benzoic acid, was hydrogenated in absolute ethanol in the presence of 5% Pd/C as above in Example 1, Step D. The resulting crude solid was purified by filtration through a plug of silica gel (50% EtOAc/hexanes as eluant) to give 3,4-difluoro-2-[[2-fluoro-4-(3-methoxypropyl)phenyl]amino]benzoic acid as a white solid (65%); m.p. (Et$_2$O/hexanes) 125–127° C. $^1$H NMR [400 MHz, (CD$_3$)$_2$SO] δ 13.35 (br s, 1 H), 9.27 (br s, 1 H), 7.82 (ddd, J=8.3, 6.1, 1.9 Hz, 1 H), 7.08 (dd, J=12.4, 1.7 Hz, 1 H), 7.05–6.96 (m, 2 H), 6.93 (dd, J=8.2, 1.8 Hz, 1 H), 3.33 (t, J=6.4 Hz, 2 H), 3.23 (s, 3 H), 2.59 (t, J=7.7 Hz, 2 H), 1.83–1.73 (m, 2 H). Anal. Calcd for C$_{17}$H$_{16}$F$_3$NO$_3$: C, 60.2; H, 4.8; N, 4.1. Found: C, 60.2; H, 4.7; N, 4.1.

Step D: Preparation of 3,4-difluoro-2-[[2-fluoro-4-(3-methoxypropyl)phenyl]-amino]-N-(2-hydroxyethoxy)benzamide The title compound was prepared from reaction of the product of Example 25, Step C, 3,4-difluoro-2-[[2-fluoro-4-(3-methoxypropyl)phenyl]amino]benzoic acid with CDI and 2-(aminooxy)ethanol, by the general procedure of Example 1, Step E, then purified by flash column chromatography on silica gel (50% EtOAc/hexanes) to give 3,4-difluoro-2-[[2-fluoro-4-(3-methoxypropyl)phenyl]-amino]-N-(2-hydroxyethoxy)benzamide as a cream solid (69%); m.p. (Et$_2$O/hexanes) 136–137° C. $^1$H NMR [400 MHz, (CD$_3$)$_2$SO] δ 11.85 (br s, 1 H), 8.77 (br s, 1 H), 7.43–7.36 (m, 1 H), 7.15–7.00 (m, 2 H), 6.95–6.77 (m, 2 H), 4.71 (br s, 1 H), 3.85 (t, J=4.8, 2 H), 3.56 (t, J=4.8, 2 H), 3.33 (t, J=6.4 Hz, 2 H), 3.23 (s, 3 H), 2.56 (t, J=7.7 Hz, 2 H), 1.80–1.71 (m, 2 H).

EXAMPLE 26

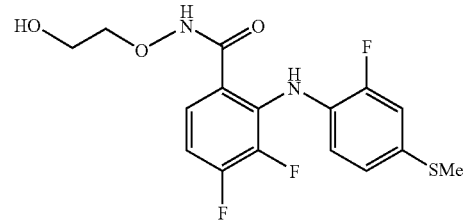

3,4-Difluoro-2-[[2-fluoro-4-(methylthio)phenyl]amino]-N-(2-hydroxyethoxy)benzamide

Step A: Preparation of 4-amino-3-fluorophenyl Thiocyanate

A solution of bromine (3.02 g, 18.9 mmol) in sodium bromide-saturated methanol (11 mL) was added dropwise to a solution of 2-fluoroaniline (2.00 g, 18.0 mmol) and potassium thiocyanate (5.25 g, 54.0 mmol) in methanol (45 mL). The mixture was stirred for 0.5 hours, at room temperature, poured into water (300 mL) and made basic with solid Na$_2$CO$_3$. This aqueous mixture was extracted with Et$_2$O (5×30 mL), then the combined Et$_2$O extracts were washed with water (2×100 mL), saturated NaCl (100 mL), and dried (Na$_2$SO$_4$). Removal of the solvent under reduced pressure afforded a pale yellow liquid which was purified by dry flash column chromatography on silica (2.5% Et$_2$O/hexanes as eluant) to give 4-amino-3-fluorophenyl thiocyanate as a white solid (1.60 g, 53%); m.p. 36–38° C. $^1$H NMR (400 MHz, CDCl$_3$) δ 7.25 (dd, J=10.5, 2.2 Hz, 1 H), 7.18 (ddd, J=8.3, 2.2, 1.0 Hz, 1 H), 6.78 (dd, J=9.0, 8.3 Hz), 4.03 (br s, 2H). Anal. Calcd for C$_7$H$_5$FN$_2$S: C, 50.0; H, 3.0; N, 16.7. Found: C, 50.2; H, 3.0; N, 16.7.

Step B: Preparation of 2-fluoro-4-methylthioaniline

A solution of the product of Example 26, Step A, 4-amino-3-fluorophenyl thiocyanate (500 mg, 2.97 mmol), in ethanol (7.5 mL) was added to a solution of sodium sulfide monohydrate (714 mg, 2.97 mmol) in water (1.5 mL) and the mixture heated at 50° C. for 2 hours. Methyl iodide (464 mg, 3.27 mmol) in ethanol (0.5 mL) was added and heating continued for a further 4 hours. The reaction mixture was then diluted with water (15 mL) and extracted with Et$_2$O (4×5 mL). The combined Et$_2$O extracts were washed with water (3×10 mL), saturated NaCl (10 mL), and dried (Na$_2$SO$_4$), followed by removal of the solvent under reduced pressure to afford a pale yellow oil. This material was purified by dry flash column chromatography on silica (5% Et₂O/hexanes as eluant) to give 2-fluoro-4-methylthioaniline as a pale yellow oil (407 mg, 87%); ¹H NMR (400 MHz, CDCl₃) δ 7.01 (dd, J=11.3, 2.1 Hz, 1 H), 6.94 (ddd, J=8.2, 2.1, 0.9 Hz, 1 H), 6.71 (dd, J=9.3, 8.2 Hz, 1 H), 3.67 (br s, 2 H), 2.42 (s, 3 H).

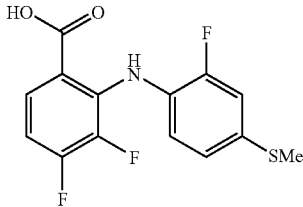

Step C: Preparation of 3,4-difluoro-2-[[2-fluoro-4-(methylthio)phenyl]amino]-benzoic acid 2,3,4-Trifluorobenzoic acid and the product of Example 26, Step B, 2-fluoro-4-methylthioaniline, were reacted in the presence of LiHMDS solution in THF by the general procedure of Example 1, Step B. After workup, this material was purified by dry flash column chromatography on silica (0.5% Et₂O in 1:1 CH₂Cl₂/hexanes as eluant) to afford 3,4-difluoro-2-[[2-fluoro-4-(methylthio)phenyl]amino]benzoic acid as a cream solid (52%); m.p. (Et₂O/hexanes) 210–220° C. ¹H NMR (400 MHz, CDCl₃) δ 13.70 (br s, 1 H), 9.24 (br s, 1 H), 7.81 (ddd, J=9.0, 6.1, 2.1 Hz, 1 H), 7.20 (dd, J=11.8, 1.9 Hz, 1 H), 7.03–6.99 (m, 3 H), 2.47 (s, 3 H). Anal. Calcd for C₁₄H₁₀F₃NO₂S.0.125 Et₂O: C, 54.0; H, 3.5; N, 4.3. Found: C, 54.2; H, 3.3; N, 4.5.

Step D: Preparation of 3,4-difluoro-2-[[2-fluoro-4-(methylthio)phenyl]amino]-N-(2-hydroxyethoxy)benzamide The title compound was prepared from reaction of the product of Example 26, Step C, 3,4-difluoro-2-[[2-fluoro-4-(methylthio)phenyl]amino]benzoic acid, with CDI and 2-(aminooxy)ethanol by the general procedure of Example 1, Step E. Then, after workup, the crude solid triturated with Et₂O and washed with pentane to afford 3,4-difluoro-2-[[2-fluoro-4-(methylthio)phenyl]amino]-N-(2-hydroxyethoxy)benzamide as a white solid (80%); m.p. (Et₂O) 108–111° C. ¹H NMR [400 MHz, (CD₃)₂SO] δ 11.80 (br s, 1 H), 8.77 (br s, 1 H), 7.40 (ddd, J=9.0, 5.8, 2.0 Hz, 1 H), 7.18 (dd, J=12.0, 2.2 Hz, 1 H), 7.13 (ddd, J=9.9, 9.0, 7.2 Hz, 1 H), 6.99 (ddd, J=8.5, 2.4, 0.8 Hz, 1 H), 6.87 (td, J=8.9, 4.5 Hz, 1 H), 4.71 (br s, 1 H), 3.86 (t, J=4.9 Hz, 2 H), 3.57 (t, J=4.9 Hz, 2 H), 2.45 (s, 3 H). Anal. Calcd for C₁₆H₁₅F₃N₂O₃S: C, 51.6; H, 4.1; N, 7.5. Found: C, 52.1; H, 4.3; N, 7.6.

EXAMPLE 27

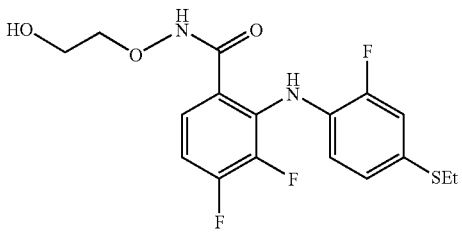

3,4-Difluoro-2-[[2-fluoro-4-(ethylthio)phenyl]amino]-N-(2-hydroxyethoxy)benzamide

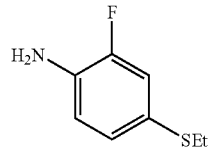

Step A: Preparation of 2-fluoro-4-ethylthioaniline

A solution of the product of Example 26, Step A, 4-amino-3-fluorophenyl thiocyanate (500 mg, 2.97 mmol), in ethanol (7 mL) was added dropwise to a solution of Na₂S.9H₂O (714 mg, 2.97 mmol) in water (1.5 mL) and the resulting mixture stirred at 50° C. for 1 hour. A solution of ethyl iodide (510 mg, 3.27 mmol) in ethanol (1 mL) was then added and the reaction stirred at 50° C. for a further 6 hours. The mixture was diluted with water (30 mL) and extracted with Et₂O (4×10 mL), then the combined Et₂O extracts washed with water (3×20 mL), saturated NaCl (20 mL) and dried (Na₂SO₄). Removal of the solvent under reduced pressure afforded a pale yellow oil which was purified by dry flash column chromatography on silica (5% Et₂O/hexanes as eluant) to afford 2-fluoro-4-ethylthioaniline as a colourless oil (470 mg, 92%). ¹H NMR (400 MHz, CDCl₃) δ 7.08 (dd, J=11.3, 2.0 Hz, 1 H), 7.01 (ddd, J=8.2, 2.0, 0.9 Hz, 1 H), 6.71 (dd, J=9.3, 8.2 Hz, 1 H), 3.81 (br s, 2 H), 2.80 (q, J=7.3 Hz, 2 H), 1.24 (t, J=7.3 Hz, 3 H).

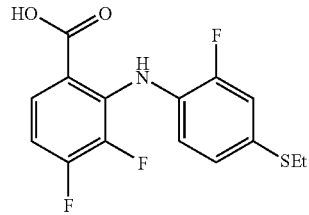

Step B: Preparation of 3,4-difluoro-2-[[2-fluoro-4-(ethylthio)phenyl]amino]-benzoic acid 2,3,4-Trifluorobenzoic acid and the product of Example 27, Step A, 2-fluoro-4-ethylthioaniline, were reacted in the presence of LiHMDS solution in THF by the general procedure of Example 1, Step B. After workup, a yellow solid was obtained which was purified by dry flash column chromatography on silica (0.5% Et₂O in 1:1 CH₂Cl₂/hexanes as eluant) to afford 3,4-difluoro-2-[[2-fluoro-4-(ethylthio)phenyl]amino]benzoic acid as a yellow solid (55%); m.p. (Et₂O) 136–139° C. ¹H NMR (400 MHz, CDCl₃) δ 13.70 (br s, 1 H), 9.24 (br s, 1 H), 7.81 (ddd, J=9.2, 6.1, 2.1 Hz, 1 H), 7.26 (dd, J=11.8, 2.0 Hz, 1 H), 7.08 (dd, J=8.3, 2.0 Hz, 1 H), 7.06 (td, J=9.7, 7.0 Hz, 1 H), 7.02 (ddd, J=9.2, 8.3, 4.7 Hz, 1 H), 2.96 (q, J=7.3 Hz, 2 H), 1.22 (t, J=7.3 Hz, 3 H). Anal. Calcd for C₁₅H₁₂F₃NO₂S: C, 55.0; H, 3.7; N, 4.3. Found: C, 55.5; H, 3.7; N, 4.3.

Step C: Preparation of 3,4-difluoro-2-[[2-fluoro-4-(ethylthio)phenyl]amino]-N-(2-hydroxyethoxy)benzamide The title compound was prepared from reaction of the product of Example 27, Step B, 3,4-difluoro-2-[[2-fluoro- 4-(ethylthio)phenyl]amino]benzoic acid with CDI and 2-(aminooxy)ethanol by the general procedure of Example 1, Step E. Then, after workup, the crude solid triturated with Et₂O and washed with pentane to afford 3,4-difluoro-2-[[2-fluoro-4-(ethylthio)phenyl]amino]-N-(2-hydroxyethoxy)benzamide as a white solid (65%); m.p. (Et₂O) 129–132° C. ¹H NMR [400 MHz, (CD₃)₂SO] δ 11.80 (br s, 1 H), 8.77 (br s, 1 H), 7.41 (ddd, J=9.0, 5.8, 2.1 Hz, 1 H), 7.23 (dd, J=11.8, 2.1 Hz, 1 H), 7.15 (ddd, J=9.9, 8.9, 7.2 Hz, 1 H), 7.04 (ddd, J=8.5, 2.1, 0.9 Hz, 1 H), 6.85 (ddd, J=9.9, 8.5, 4.2 Hz, 1 H), 4.72 (br s, 1 H), 3.85 (t, J=4.9 Hz, 2 H), 3.57 (t, J=4.9 Hz, 1 H), 2.92 (q, J=7.3 Hz, 2 H), 1.20 (t, J=7.3 Hz, 3 H). Anal. Calcd for C₁₇H₁₇F₃N₂O₃S: C, 52.8; H, 4.4; N, 7.3. Found: C, 53.0; H, 4.7; N, 7.2.

EXAMPLE 28

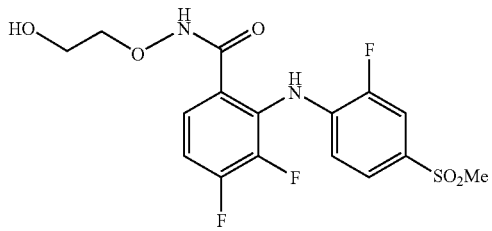

3,4-Difluoro-2-[[2-fluoro-4-(methylsulfonyl)phenyl]amino]-N-(2-hydroxyethoxy)benzamide

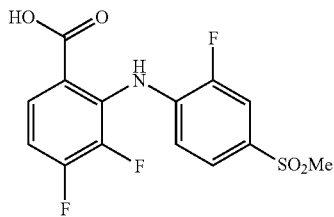

Step A: Preparation of 3,4-difluoro-2-[[2-fluoro-4-(methylsulfonyl)phenyl]-amino]benzoic acid CH₂Cl₂ (2 mL) was added to a mixture of the product of Example 26, Step C, 3,4-difluoro-2-[[2-fluoro-4-(methylthio)phenyl]amino]benzoic acid (150 mg, 0.48 mmol), and m-chloroperbenzoic acid (295 mg, 1.20 mmol). The reaction was stirred at room temperature for 4 hours, then concentrated, and the crude reaction mixture loaded directly onto a column for purification by dry flash chromatography on silica (9% Et₂O/CH₂Cl₂ as eluant). 3,4-Difluoro-2-[[2-fluoro-4-(methylsulfonyl)phenyl]amino]benzoic acid was isolated as a white solid (141 mg, 85%); m.p. (Et₂O) 220–224° C. ¹H NMR [400 MHz, (CD₃)₂SO] δ 13.60 (br s, 1 H), 9.27 (br s, 1 H), 7.84 (ddd, J=8.7, 5.9, 1.9 Hz, 1 H), 7.76 (dd, J=11.0, 2.1 Hz, 1 H), 7.60 (ddd, J=8.5, 2.1, 0.6 Hz, 1 H), 7.31 (td, J=9.3, 7.4 Hz, 1 H), 7.05 (td, J=8.5, 5.4 Hz, 1 H), 3.20 (s, 3 H). Anal. Calcd for C₁₄H₁₀F₃NO₄S: C, 46.3; H, 3.3; N, 3.9. Found: C, 46.7; H, 3.0; N, 3.8.

Step) B: Preparation of 3,4-difluoro-2-[[2-fluoro-4-(methylsulfonyl)phenyl]-amino]-N-(2-hydroxyethoxy)benzamide The title compound was prepared from reaction of the product of Example 28, Step A, 3,4-difluoro-2-[[2-fluoro-4-(methylsulfonyl)phenyl]amino]benzoic acid, with CDI and 2-(aminooxy)ethanol by the general procedure of Example 1, Step E. Then, after workup, the crude solid purified by dry flash column chromatography on silica (5% isopropanol/hexanes as eluant) to afford 3,4-difluoro-2-[[2-fluoro-4-(methylsulfonyl)phenyl]amino]-N-(2-hydroxyethoxy)benzamide as a white solid (52%); m.p. (Et₂O) 85–88° C. ¹H NMR [400 MHz, (CD₃)₂SO] δ 11.78 (br s, 1 H), 8.88 (br s, 1 H), 7.72 (dd, J=11.1, 2.1 Hz, 1 H), 7.55 (ddd, J=8.8, 2.1, 0.6 Hz, 1 H), 7.48–7.35 (m, 2 H), 6.87 (td, J=8.8, 4.0 Hz, 1 H), 4.68 (br s, 1 H), 3.81 (t, J=4.6 Hz, 2 H), 3.54 (td, J=4.9, 4.2 Hz, 2 H), 3.18 (s, 3 H). Anal. Calcd for C₁₆H₁₅F₃N₂O₅S: C, 47.5; H, 3.6; N, 6.9. Found: C, 47.3; H, 3.8; N, 6.6.

EXAMPLE 29

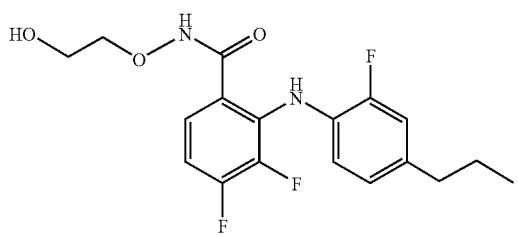

3,4-Difluoro-2-(2-fluoro-4-propylanilino)-N-(2-hydroxyethoxy)benzamide

The product of Example 6,2-(4-Allyl-2-fluoroanilino)-3,4-difluoro-N-(2-hydroxyethoxy)benzamide was dissolved in absolute EtOH and hydrogenated in the presence of 5% Pd/C by the procedure of Example 1, Step D. Purification of the resulting oil was carried out by filtration through a plug of silica gel (50% EtOAc/PE as eluant) to give 3,4-difluoro-2-(2-fluoro-4-propylanilino)-N-(2-hydroxyethoxy)benzamide as a white solid (77%); m.p. (EtOAc/hexane) 144–146° C. ¹H NMR [400 MHz, (CD₃)₂SO] δ 11.85 (br s, 1 H), 8.76 (br s, 1 H), 7.43–7.33 (m, 1H), 7.14–7.06 (m, 1 H), 7.04 (dd, J=12.5, 1.5 Hz, 1 H), 6.88 (dd, J=8.3, 1.7 Hz, 1H), 6.83 (ddd, J=8.6, 8.6, 4.2 Hz, 1 H), 4.70 (br s, 1 H), 3.86 (t, J=4.9 Hz, 2 H), 3.57 (t, J=4.9 Hz, 2 H), 2.49 (t, J=7.7 Hz, 2 H), 1.56 (sextet, J=7.4 Hz, 2 H), 0.87 (t, J=7.3 Hz, 3 H). Anal. calcd. for C₁₈H₁₉F₃N₂O₃: C, 58.7; H, 5.2; N, 7.6. Found C, 58.8; H, 5.2; N, 7.7.

EXAMPLE 30

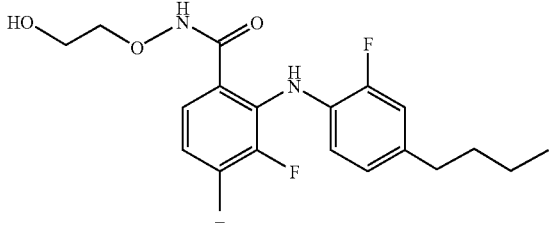

2-(4-Butyl-2-fluoroanilino)-3,4-difluoro-N-(2-hydroxyethoxy)benzamide

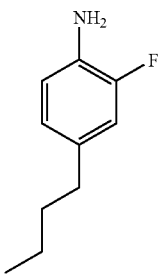

Step A: Preparation of 4-butyl-2-fluoroaniline

ZnCl₂ (5.17 g, 38.0 mmol) was weighed into a flask, which was then flame dried and flushed with N₂. Anhydrous THF (20 ml) was then added at 0° C., followed by 2.5 M ⁿBuLi (15.2 ml, 38.0 mmol). The reaction mixture was stirred at 0° C. for 15 min, after which 2-fluoro-4-iodoaniline (3.00 g, 12.7 mmol) in anhydrous THF (10 ml) and Pd(PPh₃)₄ (0.74 g, 0.64 mmol) were added sequentially. The mixture was allowed to warm to RT and stirred for a further 6 h. The mixture was poured into ice/Et₂O, the organic layer separated and the aqueous layer further extracted with Et₂O. The combined organic fractions were washed with sat. NaHCO₃, dried (Na₂SO₄) and concentrated under reduced pressure. The resulting solid was removed from the mixture by filtration and the filtrate purified by flash chromatography on silica (12.5% EtOAc/Hexane as eluant) to give the desired product (30%, 3.7 mmol). $^1$H NMR [400 MHz, CDCl₃] δ 6.80 (dd, J=12.1, 1.8 Hz, 1 H), 6.76–6.65 (m, 2 H), 3.65 (br s, 2 H), 2.49 (t, J=7.7 Hz, 2 H), 1.57–1.49 (m, 2 H), 1.32 (sextet, J=7.3 Hz, 2 H), 0.91 (t, J=7.3 Hz, 3 H). LCMS (ACPI⁺) 168 (100%).

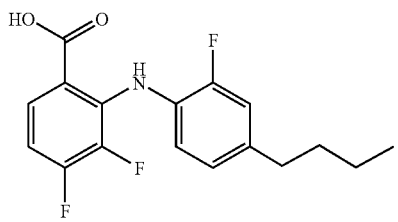

Step B: Preparation of 2-(4-butyl-2-fluoroanilino)-3,4-difluorobenzoic acid 2,3,4-Trifluorobenzoic acid and 4-butyl-2-fluoroaniline were reacted in the presence of LiHMDS solution in THF by the general procedure of Example 1, Step B, affording crude 2-(4-butyl-2-fluoroanilino)-3,4-difluorobenzoic acid after workup. The crude material was further purified by flash chromatography on silica (10% EtOAc/Hexane as eluant) to give the desired compound (40%). $^1$H NMR [400 MHz, CH₃OD] δ 7.86 (ddd, J=8.4, 5.8, 2.1 Hz, 1 H), 6.96–6.86 (m, 3 H), 6.78 (ddd, J=9.4, 9.4, 7.1 Hz, 1 H), 2.58 (t, J=7.7 Hz, 2 H), 1.63–1.55 (m, 2 H), 1.36 (sextet, J=7.4, 2H), 0.94 (t, J=7.5, 3 H). LCMS (ACPI⁺) 329 (100%).

Step C: Preparation of 2-(4-butyl-2-fluoroanilino)-3,4-difluoro-N-(2-hydroxyethoxy)benzamide The title compound was prepared from reaction of 2-(4-butyl-2-fluoroanilino)-3,4-difluorobenzoic acid with CDI and 2-(aminooxy)ethanol by the general procedure of Example 1, Step E, then purified by flash column chromatography on silica (50% EtOAc/Hexane as eluant) to give 2-(4-butyl-2-fluoroanilino)-3,4-difluoro-N-(2-hydroxyethoxy)benzamide as a white solid (68%); m.p. (EtOAc/Hexane) 163–165° C.

$^1$H NMR [400 MHz, (CD₃)₂SO] δ 11.85 (br s, 1 H), 8.74 (br s, 1 H), 7.44–7.38 (m, 1H), 7.14–7.06 (m, 1 H), 7.06–7.01 (m, 1 H), 6.88 (dd, J=8.3, 1.1 Hz, 1 H), 6.83 (ddd, J=8.4, 8.4, 4.2 Hz, 1 H), 4.73 (br s, 1 H), 3.87 (t, J=4.8 Hz, 2 H), 3.58 (t, J=4.8 Hz, 2 H), 2.52 (t, J=7.5 Hz, 2 H), 1.57–1.48 (m, 2 H), 1.29 (sextet, J=7.3 Hz, 2 H), 0.89 (t, J=7.3 Hz, 3 H). Anal. Calcd for C₁₇H₁₅F₃N₂O₃: C, 59.7; H, 5.5; N, 7.3. Found C, 59.4; H, 5.4; N, 7.4.

EXAMPLE 31

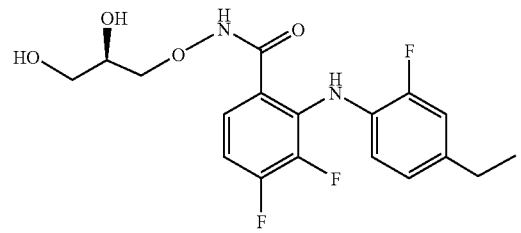

N-[(R—)2,3-Dihydroxy-propoxy]-2-(4-ethyl-2-fluoro-phenylamino)-3,4-difluoro-benzamide

Step A: Preparation of 1.2:5,6-di-O-isopropylidene-D-mannitol

To a stirring suspension of D-Mannitol (1.82 g, 10.0 mmol) in tetrahydrofuran (21 mL) and dimethylformamide (9 mL) was added p-toluenesulfonic acid monohydrate (0.02 g, 0.1 mmol,) at ambient temperature, followed by 2,2-dimethoxypropane (2.8 mL, 0.023 mol). The reaction mixture was stirred for 18 hours at room temperature, then additional 2,2-dimethoxypropane (0.3 mL, 2.4 mmol) was added. The suspension was heated to 40° C. to 45° C., and stirred for 2 hours. Sodium bicarbonate (1.8 g, 0.016 mol) was added to neutralize the acid and the mixture was stirred for 30 minutes. The excess Na₂CO₃ was filtered and washed with tetrahydrofuran (5 mL). The filtrate was concentrated. To the remaining light yellow oil was added toluene (15 mL) and the mixture was stirred at 3° C. to 5° C. until a light-yellow gelatinous solid formed. The solid was filtered and washed with hexane (2×5 mL). The product was dried in a vacuum oven for 18 hours to give 1,2:5,6-di-O-isopropylidene-D-mannitol (1.24 g, 47.3%) as an off-white solid, mp 110–113° C.

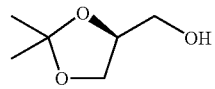

Step B: Preparation of (S)-(+)-(2,2-dimethyl-[1,3]dioxolan-4-yl)-methanol

To a solution of the product of Example 31, Step A, 1,2:5,6-di-O-isopropylidene-D-mannitol (50 g, 0.191 mol), in water (700 mL), was added solid sodium bicarbonate (20 g). The resultant solution was stirred until all the solid dissolved, and then cooled in an ice-water bath. Solid sodium periodate (81.5 g, 0.381 mol) was slowly added to the solution portionwise. Gas evolution observed. The white mixture was stirred at ambient temperature for 2 hours. Solid sodium chloride (30 g) was added, and the mixture was stirred for 15 minutes. The white solid was filtered. The filtrate was cooled in an ice-water bath. Solid sodium borohydride was added slowly. Gas bubbles evolved. The mixture was warmed to ambient temperature, and stirred overnight. The milky mixture turned to a clear solution. The aqueous solution was extracted with dichloromethane (3×). The organic solution was washed with brine, and dried over magnesium sulfate. The solvent was removed in vacuo to give (S)-(+)-(2,2-dimethyl-[1,3]dioxolan-4-yl)-methanol as a colorless oil, which was dried under high vacuum at ambient temperature overnight, 34.82 g (60%); MS (APCI+)=133 (M$^+$+1).

Step C: Preparation of (R)-2-(2,2-dimethyl-[1,3]dioxolan-4-ylmethoxy)-isoindole-1,3-dione A 3-L round-bottomed flask equipped with mechanical stirrer and additional funnel was charged with N-hydroxyphthalimide (68.0 g, 0.416 mol) and tetrahydrofuran (1.2 L) under nitrogen atmosphere. To this solution was added triphenylphosphine (109.2 g, 0.416 mol) and the product of Example 31, Step B, (S)-(2,2-dimethyl-[1,3]dioxolan-4-yl)-methanol (55.0 g, 0.416 mol). The mixture was cooled to 3° C. to 5° C. and diethyl azodicarboxylate (85.2 mL, 0.541 mol) was added dropwise, while keeping the inner temperature below 15° C. The reaction mixture was warmed to ambient temperature, and stirred for 18 hours. The tetrahydrofuran was evaporated under reduced pressure. To the remaining orange solid was added dichloromethane (0.5 L) and the mixture was stirred for 1 hour. The white solid (Ph$_3$PO) was filtered and washed with dichloromethane (0.1 L). The solvent was removed and ethanol (0.5 L) was added to the resulting solid. The mixture was stirred for 2 hours at 3° C. to 5° C. The white solid was filtered, washed with a small amount of cold EtOH, and dried in vacuum oven at 40° C. to give (R)-2-(2,2-dimethyl-[1,3]dioxolan-4-ylmethoxy)-isoindole-1,3-dione (112.5 g, 97%) as a white solid: $^1$H NMR (CDCl$_3$): δ 1.33 (s, 3 H), 1.99 (s, 3 H), 3.96 (m, 1 H), 4.15 (m, 2 H), 4.30 (m, 1 H), 4.48 (m, 1 H), 7.59 (m, 2 H), 7.84 (m, 2 H); MS (APCI+)=278 (M$^+$+1).

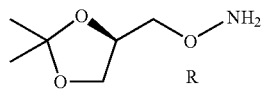

Step D: Preparation of (R)-(2,2-dimethyl-[1.3]dioxolan-4-ylmethyl)-hydroxylamine To a stirring solution of the product of Example 31, Step C, (R)-2-(2,2-dimethyl-[1,3]dioxolan-4-ylmethoxy)-isoindole-1,3-dione (74.9 g, 0.27 mol) in dichloromethane (480 mL) at 3° C. to 5° C. was added methylhydrazine (15.8 mL, 0.29 mol) dropwise. The color of the suspension turned from yellow to white. The cooling bath was removed and the mixture was stirred for 2 hours at ambient temperature. The resulting suspension was concentrated on a rotary evaporator. To the white solid was added ether (0.5 L) and the resulting mixture was stirred for 1.5 hours at ambient temperature. The white precipitate was filtered and washed with ether (0.2 L). The filtrate was concentrated on rotary evaporator to give (R)-(2,2-dimethyl-[1,3]dioxolan-4-ylmethyl)-hydroxylamine (39.0 g, 98.3%): $^1$H NMR (CDCl$_3$): δ 1.35 (s, 3 H), 1.42 (s, 3H), 3.73 (m, 3H), 4.05 (m, 1H), 4.33 (m, 1H), 5.39 (m, 2 ) H; MS (APCI+)=148.1 (M$^+$+1).

Step E: Preparation of N-((R)-2,2-Dimethyl-[1,3]dioxolan-4-ylmethoxy)-2-(4-ethyl-2-fluoro-phenylamino)-3,4-difluoro-benzamide To a stirring solution of the product of Example 1, Step D, 2-[(4-ethyl-2-fluorophenyl)amino]-3,4-difluorobenzoic acid (0.480 g, 1.626 mmol) in dichloromethane (25 mL) is added to the product of Example 31, Step D, (R)—O-(2,2-dimethyl-[1,3]dioxan-4-ylmethyl)-hydroxylamine (0.38 g, 2.57 mmol), triethylamine (0.54 mL, 3.85 mmol), and benzotriazole-1-yl-oxy-tris-pyrrolidino-phosphonium hexafluorophosphate (1.34 g, 2.57 mmol) and allowed to stir at ambient temperature for 90 minutes. The reaction mixture was concentrated in vacuo and the affording residue was partitioned between ethyl acetate and water. The organic layers were washed twice with saturated sodium carbonate solution and twice with brine. The organic layer was collected, dried over sodium sulfate, filtered and concentrated in vacuo. N-((R)-2,2-Dimethyl-[1,3]dioxolan-4-ylmethoxy)-2-(4-ethyl-2-fluoro-phenylamino)-3,4-difluoro-benzamide was isolated via silica column chromatography in 4:1 hexanes/ethyl acetate, then 3:1 hexanes/ethyl acetate affording a white foam (0.515 g, 56.7%).

Step F: Preparation of N-[(R–)2,3-dihydroxy-propoxy]-2-(4-ethyl-2-fluoro-phenylamino)-3,4-difluoro-benzamide To a stirring solution of the product of Example 31, Step E, N-((R)-2,2-dimethyl-[1,3]dioxolan-4-ylmethoxy)-2-(4-ethyl-2-fluoro-phenylamino)-3,4-difluoro-benzamide (0.515 g, 1.213 mmol) in methanol (10 mL) and water (1 mL) was added p-toluenesulfonic acid (0.115 g, 0.607 mmol). After stirring for 17 hours the reaction mixture was partitioned between ethyl acetate and water. The organic layer was washed twice saturated sodium carbonate solution and twice with brine. The organic layer was collected, dried over sodium sulfate, filtered and concentrated in vacuo to afford N-[(R)-2,3-dihydroxy-propoxy]-2-(4-ethyl-2-fluoro-phenylamino)-3,4-difluoro-benzamide (0.440 g, 94.4%) as a clear oil/foam. 1NMR (400 MHz; CD$_3$OD) δ 7.35 (1H, m), 6.84–6.95 (3H, m), 6.76–6.79 (1H, m), 3.91–3.94 (1H, m), 3.81–3.85 (2H, m), 3.53–3.55 (2H, m), 2.57 (2H, q, J=15.1, 7.6 Hz), 1.19 (3H, t, J=7.6 Hz); $^{19}$F-NMR (376 MHz; CD$_3$OD) δ −132.3, −134.8, −147.3; MS(APCI+)=385; Anal. calcd/found for C$_{18}$H$_{19}$F$_3$N$_2$O$_4$: C, 56.25/56.22; H, 4.98/4.93; N, 7.29/7.17; [α]$^{25}_D$ −5.6° (c 10.8, EtOH).

EXAMPLE 32

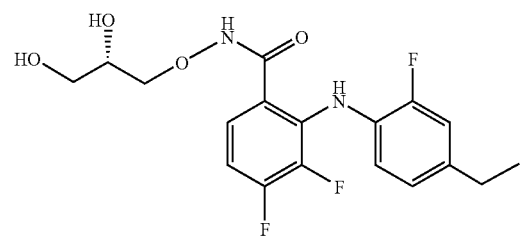

N-[(S+)2,3-Dihydroxy-propoxy]-2-(4-ethyl-2-fluoro-phenylamino)-3,4-difluoro-benzamide

Step A: Preparation of L-gulonic γ-lactone

To a solution of L-ascorbic acid in water is added Pd/C (10%). The mixture is subjected to hydrogenation in a Parr hydrogenator at 48 psi, 18° C. for about 2 to 3 days. The reaction mixture is filtered and the filtrate is concentrated in vacuo to afford L-gulonic γ-lactone, after drying at 50° C. in a vacuum oven for about 1 to 3 hours.

Step B: Preparation of 5,6-isopropylidene-L-gulonic Acid γ-lactone

The product of Example 32, Step A, L-gulonic γ-lactone is dissolved in a mixture of tetrahydrofuran and dimethylformamide. p-Toluenesulfonic acid monohydrate is added and the reaction mixture is cooled to 0° C. to 5° C. in an ice-water bath. 2,2-Dimethoxypropane is added dropwise, and the reaction mixture is stirred at ambient temperature for about 1 to 3 hours. The mixture is neutralized with solid sodium carbonate and stirred for about 1 hour. The solid is filtered and washed with tetrahydrofuran. The THF is removed under vacuo, and DMF by distillation under high vacuum. The resulting orange solid is triturated with toluene, filtered, washed with toluene, and dried in a vacuum oven at 40° C. for about 3 days, to yield 5,6-isopropylidene-L-gulonic Acid γ-lactone.

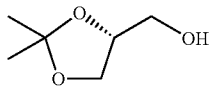

Step C: Preparation of (R)-(+)-(2,2-dimethyl-[1,3]dioxolan-4-yl)-methanol

To a stirring suspension of the product of Example 32, Step B, 5,6-O-isopropylidene-L-gulono-1,4-lactone, in water is added solid sodium periodate in small portions at 3° C. to 5° C. The pH of the mixture is adjusted to 5.5 with 1N aqueous sodium hydroxide. The suspension is stirred for 2 hours at ambient temperature, then saturated with sodium chloride and filtered. To the filtrate, at 3° C. to 5° C., is added sodium borohydride in small portions. The reaction mixture is stirred for 18 hours at ambient temperature. Acetone is added to destroy the excess of sodium borohydride, and the stirring is continued for 30 minutes. The acetone is removed under reduced pressure and the aqueous residue is extracted with dichloromethane and EtOAc. The combined organic layers are dried over magnesium sulfate, filtered, and evaporated to give (R)-(+)-(2,2-dimethyl-[1,3]dioxolan-4-yl)-methanol.

Step D: Preparation of (S)—O-(2,2-dimethyl-[1,3]dioxolan-4-ylmethyl)-hydroxylamine By the general procedure of Example 31, Step C and Step D, the product of Example 32, Step C, (R)-(+)-(2,2-dimethyl-[1,3]dioxolan-4-yl)-methanol is used to provide (S)-O-(2,2-dimethyl-[1,3]dioxolan-4-ylmethyl)-hydroxylamine.

Step E: Preparation of N-[(S+)2,3-Dihydroxy-propoxy]-2-(4-ethyl-2-fluoro-phenylamino)-3,4-difluoro-benzamide By the general procedure of Example 31, Step E and Step F, the product of Example 32, Step D, (S)-O-(2,2-dimethyl-[1,3]dioxolan-4-ylmethyl)-hydroxylamine is used to provide N-[(S+)2,3-Dihydroxy-propoxy]-2-(4-ethyl-2-fluoro-phenylamino)-3,4-difluoro-benzamide.

EXAMPLE 33

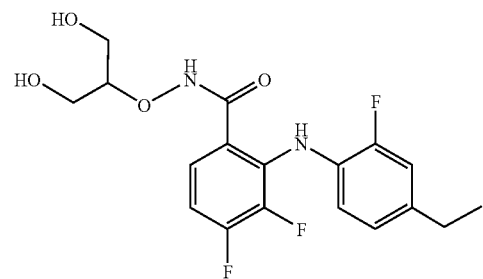

2-(4-Ethyl-2-fluoro-phenylamino)-3,4-difluoro-N-(2-hydroxy-1-hydroxymethyl-ethoxy)-benzamide

Step A: Preparation of 2-(2,2-dimethyl-[1,3]dioxan-5-yloxy)-isoindole-1,3-dione 2,2-Dimethyl-[1,3]dioxan-5-ol was prepared as described previously (Forbes, D. C. et al.; *Synthesis*, 1998; 6:879–882). $^1$H NMR (400 MHz; DMSO-d$_6$) δ 4.91 (d, 1H, J=5.1), 3.70–3.75 (m, 2 H), 3.41–3.46 (m, 3 H), 1.30 (s, 3 H), 1.24 (s, 3 H); MS (APCI+)=132.9. To a stirring solution of 2,2-dimethyl-[1,3]dioxan-5-ol (1.50 g, 11.35 mmol), N-hydroxyphthalimide (1.85 g, 11.35 mmol), and triphenylphosphine (2.98 g, 11.35 mmol) in anhydrous tetrahydrofuran (30 mL) at 0° C. was added diethyl azodicarboxylate (2.3 mL, 14.75 mmol). The resultant solution was allowed to warm to room temperature. After stirring for 3 hours, the mixture was concentrated in vacuo and charged with chloroform affording white solids. The solids were filtered off and filtrate was collected and concentrated. The residue was purified via silica column chromatography (4:1 hexanes/ethyl acetate) affording 2-(2,2-dimethyl-[1,3]dioxan-5-yloxy)-isoindole-1,3-dione as clear crystals (1.74 g, 55% over 2 steps): $^1$H NMR (400 MHz; DMSO-d$_6$) δ 7.83 (s, 4 H), 4.11–4.12 (m, 1 H), 4.04–4.09 (m, 2 H), 3.92–3.96 (m, 2 H), 1.32 (s, 3 H), 1.25 (s, 3 H); MS (APCI+)=278.0.

Step B: Preparation of O-(2,2-dimethyl-[1,3]dioxan-5-yl)-hydroxylamine

To a stirring solution of the product of Example 33, Step A, 2-(2,2-dimethyl-[1,3]dioxan-5-yloxy)-isoindole-1,3-dione (1.72 g, 6.20 mmol), in dichloromethane (15 mL) at 0° C. under nitrogen was added methylhydrazine (0.36 mL, 6.82 mmol) and allowed to warm to room temperature. After stirring for 2 hours the reaction mixture was concentrated in vacuo and charged with diethylether. The solids were filtered off and the filtrate was collected and concentrated to afford O-(2,2-dimethyl-[1,3]dioxan-5-yl)-hydroxylamine as a yellow oil (0.97 g, 100%). $^1$H NMR (400 MHz;DMSO-d$_6$) δ 5.98 (bs, 2 H), 3.84–3.87 (m, 2 H), 3.66–3.68 (m, 2 H), 3.30–3.35 (m, 1 H), 1.29 (s, 3 H), 1.22 (s, 3 H); MS (APCI+)=147.9.

Step C: Preparation of N-(2,2-dimethyl-[1,3]dioxan-5-yloxy)-2-(4-ethyl-2-fluoro-phenylamino)-3,4-difluoro-benzamide To a stirring solution of the product of Example 1, Step D, 2-[(4-ethyl-2-fluorophenyl)amino]-3,4-difluorobenzoic acid (0.480 g, 1.626 mmol) in dichloromethane (15 mL) is added the product of Example 33, Step B, O-(2,2-dimethyl-[1,3]dioxan-5-yl)-hydroxylamine (0.287 g, 1.951 mmol), triethylamine (0.41 mL, 2.927 mmol), and benzotriazole-1-yl-oxy-tris-pyrrolidino-phosphonium hexafluorophosphate (1.02 g, 1.951 mmol) and allowed to stir at ambient temperature for 75 minutes. The reaction mixture was concentrated in vacuo and the affording residue was partitioned between ethyl acetate and water. The organic layers were washed twice with saturated sodium carbonate solution and twice with brine. The organic layer was collected, dried over sodium sulfate, filtered and concentrated in vacuo. N-(2,2-Dimethyl-[1,3]dioxan-5-yloxy)-2-(4-ethyl-2-fluoro-phenylamino)-3,4-difluoro-benzamide was isolated via silica column chromatography in 4:1 hexanes/ethyl acetate affording a white foam (0.423 g, 61.4%).

Step D: 2-(4-Ethyl-2-fluoro-phenylamino)-3,4-difluoro-N-(2-hydroxy-1-hydroxymethyl-ethoxy)-benzamide To a stirring solution of the product of Example 33, Step C, N-(2,2-dimethyl-[1,3]dioxan-5-yloxy)-2-(4-ethyl-2-fluoro-phenylamino)-3,4-difluoro-benzamide (0.416 g, 0.980 mmol) in ethanol (5 mL) was added 1 molar aqueous hydrochloric acid solution (1 mL). After stirring for 1 hour at ambient temperature the reaction mixture was partitioned between ethyl acetate and water. The organic layer was washed twice with water and twice with brine. The organic layer was collected, dried over sodium sulfate, filtered and concentrated in vacuo. The affording foam was crystallized in ethyl acetate and heptane to afford 2-(4-ethyl-2-fluoro-phenylamino)-3,4-difluoro-N-(2-hydroxy-1-hydroxymethyl-ethyl-ethoxy)-benzamide (0.318 g, 84.6%) as a white crystalline solid: m.p. 91–93° C.; $^1$NMR (400 MHz; $CD_3OD$) δ 7.38 (1H, t, J=6.8 Hz), 6.85–6.96 (3H, m), 6.73–6.78 (1H, m), 3.86–3.82 (1 H), 3.64 (4H, d, J=4.9 Hz), 2.58 (2H, q, J=15.1, 7.6 Hz), 1.19 (3H, t, J=7.6 Hz); $^{19}$F-NMR (376 MHz; $CD_3OD$) δ –132.4, –134.6, –147.2; MS(APCI+)=385; Anal.calcd/found for $C_{18}H_{19}F_3N_2O_4$: C, 56.25/56.38; H, 4.98/4.81; N, 7.29/7.25.

EXAMPLE 34

Cellular Assay for Measuring MEK Inhibition

The evaluation of the compounds as MEK inhibitors is performed in an assay that measures their ability to inhibit phosphorylation of MAP kinase (ERK) in murine colon 26 (C26) carcinoma cells. Since ERK1 and ERK2 represent the only known substrates for MEK, measurement of inhibition of ERK phosphorylation in cells provides direct readout of cellular MEK inhibition by the compounds of the invention. Briefly, the assay involves treating exponentially growing C26 cells with varying concentrations of the test compound (or vehicle control) for 1 hour at 37° C. Cells are then rinsed free of compound/vehicle and lysed in a solution containing 70 mM NaCl, 50 mM glycerol phosphate, 10 mM HEPES, pH 7.4, 1% Triton X-100, 1 mM $Na_3VO_4$, 100 μM PMSF, 10 μM leupeptin, and 10 μM pepstatin. Supernatants are then subjected to gel electrophoresis and Western blotting using a primary antibody recognizing dually phosphorylated ERK1 and ERK2. To evaluate total MAPK levels, blots were subsequently 'stripped' and re-probed with a 1:1 mixture of polyclonal antibodies recognizing unphosphorylated ERK1 and ERK2.

The inhibition data generated by the above protocol is disclosed in Table 1. If several concentrations of inhibitor were tested, $IC_{50}$ values (the concentration which gives 50% inhibition) were determined graphically from the dose response curve for % inhibition. Otherwise, percent inhibitions at measured concentrations are reported.

Table I. Cellular Inhibition of ERK Phosphorylation by Compounds of the Invention

| Compound of Example No. | $IC_{50}$ (μM) |
|---|---|
| 1 | 0.0028 |
| 2 | 0.0086 |
| 3 | 0.00015 |
| 4 | 0.0026 |
| 5 | 0.0079 |
|   | 0.018000 |
| 6 | 0.0078 |
| 7 | 0.00015 |
| 8 | 0.004 |
| 9 | 0.467 |
| 10 | 0.13 |
| 11 | 0.7 |
| 12 | >3.000000 |
| 13 | >1.000000 |
| 14 | >1.000000 |
| 15 | >1.000000 |
| 16 | >1.000000 |
| 17 | >1.000000 |
| 18 | 0.0019 |
|   | 0.150000 |
| 19 | 0.028 |
|   | 0.68 |
| 20 | 0.0021 |
|   | 0.125 |
| 21 | 0.8 |
| 23 | 0.2 |
| 24 | 0.59 |
| 25 | 0.022 |
| 26 | 0.00085 |
| 27 | 0.0022 |
| 28 | 0.72 |
| 29 | 0.0041 |
| 30 | 0.19 |
| 32 | 0.002 |

EXAMPLE 35

Carrageenan-induced Footpad Edema (CFE) Rat Model

Male outbred Wistar rats (135–150 g, Charles River Labs) are dosed orally with 10 mL/kg vehicle or test compound 1 hour prior to administration of a sonicated suspension of carrageenan (1 mg/0.1 mL saline). Carrageenan is injected into the subplantar region of the right hind paw. Paw volume is determined by mercury plethysmography immediately after injection and again five hours after carrageenan injection. Percent inhibition of edema is determined, and the ID40 calculated by linear regression. Differences in swelling compared to control animals are assessed by a 1-way ANOVA, followed by Dunnett's test.

EXAMPLE 36

Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 μg type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

EXAMPLE 37

SCW-induced Monoarticular Arthritis

Arthritis is induced as described by Schwab et al., *Infection and Immunity*, 1991; 59:4436–4442 with minor modifications. Rats receive 6 μg sonicated SCW [in 10 μL Dulbecco's PBS (DPBS)] by an intraarticular injection into the right tibiotalar joint on Day 0. On Day 21, the DTH is initiated with 100 μg of SCW (250 μL) administered IV. For oral compound studies, compounds are suspended in vehicle (0.5% hydroxypropyl-methylcellulose/0.2% Tween 80), sonicated, and administered twice daily (10 mL/kg volume) beginning 1 hour prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on Day 21, and comparing them with volumes at subsequent time points such as Day 22, 23, 24, and 25. Paw volume is determined by mercury plethysmography.

EXAMPLE 38

Mouse Ear-heart Transplant Model

Fey T. A. et al. describe methods for transplanting split-heart neonatal cardiac grafts into the ear pinna of mice and rats (*J. Pharm.* and *Toxic. Meth.*, 1998; 39:9–17). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (Day 0) through Day 13 or until grafts have been rejected. Rats are dosed once, twice, or three times daily from Day 0 through Day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10- to 20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1 to 4 times a day for 10, 20, 30 or more days. The ability of a test compound to ameliorate symptoms of transplant rejection can be compared with a control compound such as cyclosporine, tacrolimus, or orally-administered lefluonomide.

EXAMPLE 39

The analgesic activity of the compounds of the present invention is assessed by a test with rats. Rats weighing from 175 to 200 g are injected with carrageenan (2% in 0.9% sodium chloride aqueous solution, 100 μL injection volume) into the footpad of one hind limb. The rats are placed on a glass plate with illumination from a halogen lamp placed directly under the injected paw. The time (in seconds) from beginning illumination until the hindlimb was withdrawn from the glass was measured and scored as Paw Withdrawal Latency (PWL). Drug substances were given by oral gavage injection 2½ hours after carrageenan injection to the footpad. PWL was measured prior to carrageenan injection, just prior to drug injection, and 1, 2 (and sometimes 3) hours after drug injection.

Carrageenan (a polysaccharide extracted from seaweed) causes a sterile inflammation when injected under the skin. Injection into the rat footpad causes little or no spontaneous pain-related behavior but induces hyperalgesia (pain-related behavioral responses of greater intensity than expected) to peripheral thermal or mechanical stimuli. This hyperalgesia is maximal 2 to 3 hours after injection. Treatment of rats with various analgesic drugs reduces hyperalgesia measured in this way and is a conventional test for detection of analgesic activity in rats. (Hargreaves K, Dubner R, Brown F, Flores C, Joris J. A new and sensitive method for measuring thermal nociception in cutaneous hyperalgesia. *Pain*, 1988; 32:77–88 and Kayser V, Guilbaud G. Local and remote modifications of nociceptive sensitivity during carrageenan-induced inflammation in the rat. *Pain*, 1987; 28:99–108). Untreated rats have a PWL of approximately 10 seconds. Carrageenan injection reduces PWL to approximately 3 seconds for at least 4 hours, indicating thermal hyperalgesia. Inhibition of the carrageenan thermal hyperalgesia response is determined by the difference between reduced PWL prior to drug and subsequent to drug treatment, and was expressed as percent inhibition of the response. Administration of MEK inhibitors dose-dependently reduced thermal hyperalgesia.

What is claimed is:

1. A method of treating arthritis in a patient in need thereof comprising administering a therapeutically effective amount of a compound of formula I

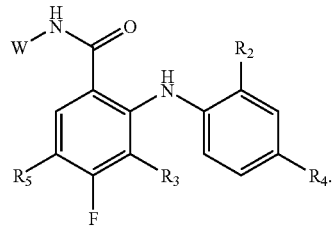

wherein
W is

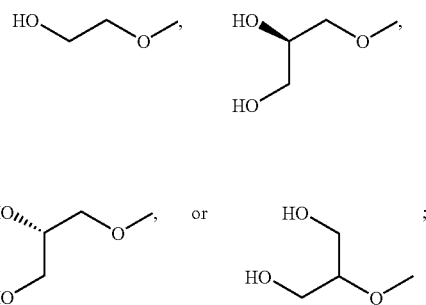

$R_2$ is hydrogen, methyl, fluorine, or chlorine;
$R_3$ is hydrogen or fluorine;
$R_4$ is $C_{1-6}$ alkyl, $C_{2-4}$ alkenyl, $C_{2-6}$ alkynyl, $C_{3-6}$ cycloalkyl, —(CH$_2$)—$C_{3-6}$ cycloalkyl, —O—($C_{1-4}$ alkyl), —S—($C_{1-2}$ alkyl), —SO$_2$CH$_3$, —SO$_2$NR$_6$R$_7$, —C≡C—(CH$_2$)$_n$NH$_2$, —C≡C(CH$_2$)$_n$OH, —C≡C—(CH$_2$)$_n$NH$_2$, —(CH$_2$)$_m$NH$_2$, —(CH$_2$)$_m$NHCH$_3$, —(CH$_2$)$_m$N(CH$_3$)$_2$, —(CH$_2$)$_m$OR$_8$, —(CH$_2$)$_q$CF$_3$, —C≡CCF$_3$, —CH=CHCF$_3$, —CH$_2$CHCF$_2$, or —CH=CF$_2$, wherein the $C_{1-6}$ alkyl and $C_{2-6}$ alkynyl are optionally substituted with between 1 and 3 substituents selected from hydroxy and alkyl;
m is 1 to 4;
n is 1 to 2;
q is 0 to 2;
$R_5$ is hydrogen or chlorine;
$R_6$ and $R_7$ are each independently hydrogen, methyl, or ethyl;
$R_8$ is independently methyl or ethyl;
or a pharmaceutically acceptable salt thereof.

2. The method of claim 1 wherein the arthritis is rheumatoid arthritis.

3. The method of claim 1 wherein the arthritis is osteoarthritis.

4. A method of treating chronic pain in a patient in need thereof comprising administering a therapeutically effective amount of a compound of formula I

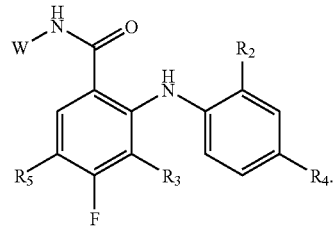

wherein
W is

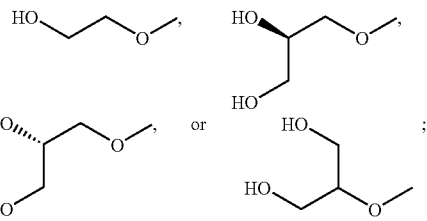

$R_2$ is hydrogen, methyl, fluorine, or chlorine;
$R_3$ is hydrogen or fluorine;
$R_4$ is $C_{1-6}$ alkyl, $C_{2-4}$ alkenyl, $C_{2-6}$ alkynyl, $C_{3-6}$ cycloalkyl, —(CH$_2$)—$C_{3-6}$ cycloalkyl, —O—($C_{1-4}$ alkyl), —S—($C_{1-2}$ alkyl), —SO$_2$CH$_3$, —SO$_2$NR$_6$R$_7$, —C≡C—(CH$_2$)$_n$NH$_2$, —C≡C(CH$_2$)$_n$OH, —C≡C—(CH$_2$)$_n$NH$_2$, —(CH$_2$)$_m$NH$_2$, —(CH$_2$)$_m$NHCH$_3$, —(CH$_2$)$_m$N(CH$_3$)$_2$, —(CH$_2$)$_m$OR$_8$, —(CH$_2$)$_q$CF$_3$, —C≡CCF$_3$, —CH=CHCF$_3$, —CH$_2$CHCF$_2$, or —CH=CF$_2$, wherein the $C_{1-6}$ alkyl and $C_{2-6}$ alkynyl are optionally substituted with between 1 and 3 substituents selected from hydroxy and alkyl;
m is 1 to 4;
n is 1 to 2;
q is 0 to 2;
$R_5$ is hydrogen or chlorine;
$R_6$ and $R_7$ are each independently hydrogen, methyl, or ethyl;
$R_8$ is independently methyl or ethyl;
or a pharmaceutically acceptable salt thereof.

5. The method of claim 4, wherein the chronic pain is selected from the group consisting of neuropathic pain, idiopathic pain, and pain associated with chronic alcoholism, vitamin deficiency, uremia, and hypothyroidism.

6. The method of claim 4, wherein the chronic pain is associated with inflammation.

7. The method of claim 4, wherein the chronic pain is associated with arthritis.

8. The method of claim 4, wherein the chronic pain is associated with post-operative pain.

9. The method of claim 5, wherein the chronic pain is the neuropathic pain.

10. The method of claim 9, wherein the neuropathic pain is associated with a condition selected from the group consisting of inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

* * * * *